(12) United States Patent
Bachmann et al.

(10) Patent No.: US 8,460,670 B2
(45) Date of Patent: Jun. 11, 2013

(54) FULLY HUMAN INFLUENZA M2 SPECIFIC ANTIBODIES

(75) Inventors: Martin F. Bachmann, Winterthur (CH); Monika Bauer, Zurich (CH); Roger Beerli, Adlikon b. Regensdorf (CH); Nicole Schmitz, Urdorf (CH)

(73) Assignee: Intercell AG, Vienna (AT)

( * ) Notice: Subject to any disclaimer, the term of this patent is extended or adjusted under 35 U.S.C. 154(b) by 54 days.

(21) Appl. No.: 13/132,658

(22) PCT Filed: Nov. 30, 2009

(86) PCT No.: PCT/EP2009/066052
§ 371 (c)(1),
(2), (4) Date: Jun. 3, 2011

(87) PCT Pub. No.: WO2010/063675
PCT Pub. Date: Jun. 10, 2010

(65) Prior Publication Data
US 2011/0268740 A1    Nov. 3, 2011

(30) Foreign Application Priority Data

Dec. 4, 2008 (EP) .................................... 08170749
Oct. 20, 2009 (EP) .................................... 09173548

(51) Int. Cl.
*A61K 39/145* (2006.01)
*C12N 5/10* (2006.01)

(52) U.S. Cl.
USPC .................... 424/147.1; 536/23.53; 435/339; 514/44 R

(58) Field of Classification Search
None
See application file for complete search history.

(56) References Cited

U.S. PATENT DOCUMENTS

| 8,003,106 B2 | 8/2011 | Mikayama et al. |
| 2003/0219442 A1 | 11/2003 | Mikayama et al. |
| 2005/0170334 A1 | 8/2005 | Mikayama et al. |

FOREIGN PATENT DOCUMENTS

| WO | WO-03/078600 A2 | 9/2003 |
| WO | WO-2006/061723 A2 | 6/2006 |
| WO | WO-2010/063675 A1 | 6/2010 |

OTHER PUBLICATIONS

Rudikoff S et al. Single amino acid substitution altering antigen-binding specificity. Proc Natl Acad Sci U S A. Mar. 1982;79(6):1979-83.*
U.S. Appl. No. 60/364,997, filed Mar. 13, 2002, Mikayama et al.
Arndt et al., Antigen binding and stability properties of non-covalently linked anti-CD22 single-chain Fv dimers. FEBS Lett. Dec. 17, 2004;578(3):257-61.
Bird et al., Single-chain antigen-binding proteins. Science. Oct. 21, 1988;242(4877):423-6.
Friguet et al., Measurements of the true affinity constant in solution of antigen-antibody complexes by enzyme-linked immunosorbent assay. J Immunol Methods. Mar. 18, 1985;77(2):305-19.
Gabbard et al., A humanized anti-M2 scFv shows protective in vitro activity against influenza. Protein Eng Des Sel. Mar. 2009;22(3):189-98. Epub Dec. 2, 2008.
Holliger et al., Engineered antibody fragments and the rise of single domains. Nat Biotechnol. Sep. 2005;23(9):1126-36.
Holliger et al., "Diabodies": small bivalent and bispecific antibody fragments. Proc Natl Acad Sci U S A. Jul. 15, 1993;90(14):6444-8.
Huston et al., Protein engineering of antibody binding sites: recovery of specific activity in an anti-digoxin single-chain Fv analogue produced in *Escherichia coli*. Proc Natl Acad Sci U S A. Aug. 1988;85(16):5879-83.
Jegerlehner et al., Influenza A vaccine based on the extracellular domain of M2: weak protection mediated via antibody-dependent NK cell activity. J Immunol. May 1, 2004;172(9):5598-605.
Jespers et al., Guiding the selection of human antibodies from phage display repertoires to a single epitope of an antigen. Biotechnology (N Y). Sep. 1994;12(9):899-903.
Kang et al., Antibody redesign by chain shuffling from random combinatorial immunoglobulin libraries. Proc Natl Acad Sci U S A. Dec. 15, 1991;88(24):11120-3.
Lazar et al., Engineered antibody Fc variants with enhanced effector function. Proc Natl Acad Sci U S A. Mar. 14, 2006;103(11):4005-10.
Lefranc, IMGT, the international ImMunoGeneTics database. Nucleic Acids Res. Jan. 1, 2003;31(1):307-10.
Liu et al., Monoclonal antibodies recognizing EVETPIRN epitope of influenza A virus M2 protein could protect m

Reference sequence (top):
`TQSPDSLAVSLGERATINCKSS` `QSVLYTSNNKNY`(CDR1) `LGWYQQKPGQPPNLLIY` `WAS`(CDR2) `TRESGVPDRFSGSGSGTDFTLTINSVQAEDVAVYY` `CQQYFMTPITF`(CDR3) `GQGTRLEIK`

| Clone | Framework 1 mutations | CDR1 | FR2 | CDR2 | FR3 | CDR3 | FR4 |
|-------|----------------------|------|-----|------|-----|------|-----|
| D005 | . | . | . | . | . | . | . |
| F004 | . | N.. | . | . | . | . | . |
| F005 | . | . | I. | . | . | . | K.. |
| F015 | A..P | L.S | . | . | . | . | KV. |
| F020 | . | .S.E | .A..K | . | . | . | K.. |
| F023 | . | . | .A..K | . | . | . | KVD |
| F025 | . | . | .A | . | . | . | . |
| F027 | A | L.S | .A..K | . | . | . | . |
| F037 | . | . | . | . | . | . | . |
| F039 | . | . | . | . | . | . | K.. |
| F040 | . | .S.E | .A | . | . | . | . |
| F044 | . | . | . | . | . | . | . |
| F045 | . | . | . | . | . | . | . |
| F046 | . | . | . | . | . | . | K.. |
| F048 | . | .N. | . | . | . | . | . |
| F052 | A.. | L.S | .A..K | . | .E. | . | K.. |
| F054 | . | . | . | . | . | . | . |
| F057 | . | .S.E | .A | . | . | . | K.. |
| F062 | . | . | . | . | .N. | . | K.. |
| F065 | . | .S.E | .A | . | . | . | K.K |
| F066 | . | . | . | . | .N. | . | . |
| F071 | . | . | . | . | . | . | K.. |
| F075 | .H. | .S | . | . | . | V. | . |
| F076 | . | . | . | . | . | . | K.. |
| F077 | A.. | L.S | .A..K | . | . | . | . |
| F084 | . | .N. | . | . | . | . | K.. |
| F087 | . | . | . | . | . | . | . |

Figure 2

| | | CDR1 | | CDR2 | | CDR3 | |
|---|---|---|---|---|---|---|---|
| D005 | SGGALVQPGRSLRLSCRTSG | LNFGDYP | INWVRQAPGKGLEWVGF | IKSKSYG | VTTEFAASVEGRFTISRDDSRGTAYLQMNSLKTEDTAVYYC | TSSSGFLYFDY | WGQGTLVTVSS |

Variants (D013, D019, D033, D037, E005, E006, E007, E011, E012, E021, E023, E028, E029, E030, E031, E033, E034, E035, E036, E040, E043, E044, E048, E049, E051, F003) shown as dots with point substitutions:

- E007: W in framework 1
- E012: S in CDR3
- E023: G in CDR2 region
- E031: N in framework between CDR2 and CDR3
- E034: N in CDR3
- E035: H in CDR3
- E044: P in CDR1 region, P in CDR2

Figure 2 continued

|  | CDR1 | CDR2 | CDR3 |
|---|---|---|---|
| D005 | SGGALVQPGRSLRLSCRTSGLNFGDYPINWVRQAPGKGLEWVGFIKSKSYGVTTEFAASVEGRFTISRDDSRGIAYLQMNSLKTEDTAVYYCTSSSGFLYYFDYWGQGTLVTVSS |
| F004 | ................................................................................................................ |
| F005 | ................................................................................................................ |
| F015 | ................................................................................................................ |
| F020 | ................................................................................................................ |
| F023 | ................................................................................................................ |
| F025 | ..............................P.......................................R...............................H........ |
| F027 | ...............................................L................................................................ |
| F037 | ................................................................................................................ |
| F039 | ........G......................................................................................................... |
| F040 | ................................................................................................................ |
| F044 | ................................................................................................................ |
| F045 | ................................................................................................................ |
| F046 | ................................................................................................................ |
| F048 | ................................................................................................................ |
| F052 | ................................................................................................................ |
| F054 | ................................................................................................................ |
| F057 | ................................................................................................................ |
| F062 | ................................................................................................................ |
| F065 | ................................................................................................................ |
| F066 | ................................................................................................................ |
| F071 | ................................................................................................................ |
| F075 | ...........................................................................A....................H............... |
| F076 | ......................................................................................................S......... |
| F077 | ..............................................................................................................P.. |
| F084 | ................................................................................................................ |
| F087 | ..............................P................................................................................. |

FULLY HUMAN INFLUENZA M2 SPECIFIC ANTIBODIES

RELATED APPLICATION

This application is a national stage filing under 35 U.S.C. §371 of international application PCT/EP2009/066052, filed Nov. 30, 2009, which was published under PCT Article 21(2) in English.

FIELD OF THE INVENTION

The present invention relates to human antibodies, preferably to fully human antibodies, which are specifically binding to influenza M2e antigen. The invention further relates to individual light- and/or heavy chains of such antibodies, to nucleic acids encoding said antibodies or their light- and/or heavy chain, and to expression vectors for the expression of said antibodies. Furthermore, the invention relates to the use of said antibodies in the treatment and/or prevention of influenza A virus infection, preferably in humans.

RELATED ART

Influenza A virus still is a major cause of disease in humans, accounting for three to five million cases of severe illness and 250,000-500,000 deaths each year. Efficient influenza A vaccines are available, which act by inducing neutralizing antibodies against hemagglutinin (HA). Since HA undergoes continuous change due to mutations (antigenic drift), new antigenic variants of influenza A arise every year requiring constant update of the vaccines. Effective vaccination is further complicated by the occasional re-assortment of the segmented viral genome leading to the replacement of HA or neuraminidase (NA) from one subtype by another subtype, a process called antigenic shift. Passive immunization with monoclonal antibodies (mAbs) targeting HA is very efficient, however, suffers the same disadvantages as the current vaccines due to antigenic shift and drift.

An ideal target for active and passive immunization strategies would therefore be a conserved viral protein. The matrix protein 2 (M2) fits the bill and has received considerable attention as a potential target against influenza infection over the past decades (Zebedee S L, Lamb R A: Influenza A virus M2 protein: monoclonal antibody restriction of virus growth and detection of M2 in virions. J Virol 1988, 62:2762-2772). M2 is a tetrameric ion channel which is involved in virus uncoating in the endosome and in virus maturation in the trans-Golgi network. Its 23 amino acid extracellular domain has remained remarkably conserved in human influenza A virus isolates over the last hundred years, at least in part due to the fact that the M2 protein is co-transcribed with the matrix protein 1 (M1). Whereas M2 is abundantly expressed on infected cells, only very few M2 molecules are present in Influenza A virus membranes. In accordance with these observations M2 specific antibodies were shown to protect by the elimination of infected cells by ADCC rather than by preventing infection through neutralization of the virus (Jegerlehner A, Schmitz N, Storni T, Bachmann M F: Influenza A vaccine based on the extracellular domain of M2: weak protection mediated via antibody-dependent NK cell activity. J. Immunol. 2004, 172:5598-5605).

Passive immunization with monoclonal antibodies has several advantages over vaccination. In particular, it allows treating people which poorly respond to vaccines, such as the elderly, young children or immune compromised individuals. In addition, passive immunization is the treatment option of choice in situations where rapid protection is crucial, such as for post-exposure treatment or prophylaxis for the acutely exposed. A number of M2 ectodomain (M2e)-specific mAbs have been reported to protect mice from a lethal challenge in a prophylactic setting. While these mAbs include fully human antibodies derived from transchromosomic mice (Wang R et al., Antiviral Res. 2008, 80:168-177; WO2006/061723A2; and WO03/078600A2), no natural human M2e-specific antibodies have been reported to date. However, for application in human subjects, natural human antibodies are the preferred choice. In contrast to humanized and fully human antibodies derived from phage display or transchromosomic mice, natural human antibodies combine the advantage of minimal immunogenicity with the smallest possible off-target reactivity and toxicity. Furthermore, human derived antibodies have the advantage of having gone through the affinity maturation process, resulting in high affinity antibodies.

SUMMARY OF THE INVENTION

A library-based screening led to the identification, isolation and cloning of 53 human scFv which showed high affinity to the extracellular domain of the influenza A M2 protein. Fully human monoclonal IgG1 antibodies have been generated from representative scFv clones. Human, and in particular fully human antibodies, are advantageous because they show less severe side effects when administered to a human subject. Without being bound to any theory this is because human, and in particular fully human, antibodies are typically and preferably not recognized by the human immune system. It has surprisingly been found that the selected antibody clones show different combinations of identical and/or highly similar CDR sequences in their light chain variable regions (LCVR) and in their heavy chain variable regions (HCVR). Based on the particular combination of CDRs, different types of LCVRs and HCVRs can be distinguished (cf. Tables 1 and 2). However, the LCVRs and HCVRs of all clones are highly similar as can be deduced from the sequence information which is provided in Tables 1 and 2. It was therefore concluded that the antibodies of the invention are clonally related. Table 3 provides an overview of the different combinations of LCVR and HCVR types as defined by their CDRs which were found in the selected clones. The table also indicates the abundance of each of these combinations among the 53 clones. Further surprisingly it has been found that the antibodies of the invention show a very high affinity towards influenza M2e antigen, and in particular towards the extracellular domain of the influenza A M2 protein. The dissociation constants (Kd) between the antibodies and RNAse-influenza A M2e antigen conjugate was found to be in the low picomolar range. An epitope mapping revealed that the minimal epitope which is recognized by antibody clone D005 is comprised in the amino acid sequence LLTEVETP (SEQ ID NO:93). This epitope is comprised by the M2 protein of most known influenza A strains. Consequently, it has been found, that the antibodies of the invention show a similarly high affinity to different variants of the extracellular domain of influenza A M2 protein which are derived from different strains of influenza A virus. It has also been demonstrated that the antibodies of the invention are specifically binding to cells which are expressing recombinant influenza A M2 protein on their surface. Moreover, antibodies of the invention were found to exhibit a preferential binding to cell-associated influenza A M2 protein. Furthermore it was found that antibodies of the invention are capable of specifically binding influenza A M2 protein in the context of influenza A virus particles. Most importantly, it has been demonstrated in a mouse model for influenza A virus infection that the antibodies of the invention are highly effective in the treatment and/or prevention of influenza A virus infection. Contrary to other influenza A M2 specific human antibodies which are known in the art, the antibodies of the invention have therapeutic activity when administered as a single dose on day one or day two after infection. The antibodies disclosed herein are therefore useful as a medicament against influenza A virus infection in a therapeutic as well as in a prophylactic setting.

TABLE 1

CDRs of the LCVRs of fully human M2 specific monoclonal antibodies. Nine types of LCVRs can be distinguished based on the combination of their CDR sequences (1A to 3B). Based on sequence similarities in the LC CDRs 3 groups of LCVRs can be distinguished: 1A to 1E, 2A to 2B, and 3A to 3B).

| Type | Clones | LC CDR1 | LC CDR2 | LC CDR 3 |
|---|---|---|---|---|
| 1A | D005 and 31 others | qsvlytsnnkny (SEQ ID NO: 1) | was (SEQ ID NO: 7) | qqyfmtpit (SEQ ID NO: 8) |
| 1B | F048, F084 | qsvlntsnnkny (SEQ ID NO: 2) | was (SEQ ID NO: 7) | qqyfmtpit (SEQ ID NO: 8) |
| 1C | E011 | qsvlhtsnnkny (SEQ ID NO: 3) | was (SEQ ID NO: 7) | qqyfmtpit (SEQ ID NO: 8) |
| 1D | E036 | qsvlytsnnkny (SEQ ID NO: 1) | was (SEQ ID NO: 7) | qqyfmapit (SEQ ID NO: 9) |
| 1E | F076 | qsvlytsnnkny (SEQ ID NO: 1) | was (SEQ ID NO: 7) | qqyfvtpit (SEQ ID NO: 10) |
| 2A | E040 and 10 others | qsvlyssnneny (SEQ ID NO: 4) | was (SEQ ID NO: 7) | qqyfmtpit (SEQ ID NO: 8) |
| 2B | E043 | qsvlyssnnedy (SEQ ID NO: 5) | was (SEQ ID NO: 7) | qqyfmtpit (SEQ ID NO: 8) |
| 3A | F052, F015, F077 | qsllyssnnkny (SEQ ID NO: 6) | was (SEQ ID NO: 7) | qqyfmtpit (SEQ ID NO: 8) |
| 3B | F027 | qsllyssnnkny (SEQ ID NO: 1) | was (SEQ ID NO: 7) | qqyfmtpia (SEQ ID NO: 11) |

TABLE 2

CDRs of the HCVRs of fully human M2 specific monoclonal antibodies. Six types of HCVRs can be distinguished based on the combination of their CDR sequences.

| Type | Clones | HC CDR1 | HC CDR2 | HC CDR 3 |
|---|---|---|---|---|
| 1A | D005 and 45 others | glnfgdyp (SEQ ID NO: 12) | iksksygvtt (SEQ ID NO: 13) | tsssgflyyfdy (SEQ ID NO: 15) |
| 1B | E031, F023, F057 | glnfgdyp (SEQ ID NO: 12) | iksksygvtt (SEQ ID NO: 13) | tsssgflyyfdh (SEQ ID NO: 16) |
| 1C | E005 | glnfgdyp (SEQ ID NO: 12) | iksksygvtt (SEQ ID NO: 13) | tssssflyyfdy (SEQ ID NO: 17) |
| 1D | E034 | glnfgdyp (SEQ ID NO: 12) | iksksygvtt (SEQ ID NO: 13) | tsnsgflyyfdy (SEQ ID NO: 18) |
| 1E | E044 | glnfgdyp (SEQ ID NO: 12) | ikskpygvtt (SEQ ID NO: 14) | tsssgflyyfdy (SEQ ID NO: 15) |
| 1F | F071 | glnfgdyp (SEQ ID NO: 12) | iksksygvtt (SEQ ID NO: 13) | tsssgfsyyfdy (SEQ ID NO: 19) |

TABLE 3

Combination of LCVRs and HCVRs as occurring in 53 independent clones of fully human M2 specific monoclonal antibodies. Clones D005, E040 and F052 (highlighted in bold) represent three of most abundant combinations of LCVR and HCVR and were thus chosen as representative clones for further analysis.

| Combinations of CDR types (LC VR-HC VR) | Clones | Number of Clones |
|---|---|---|
| 1A-1A | D005, D013, D019, D033, D037, E007, E012, E021, E028, E029, E033, E035, E049, E051, F004, F005, F025, F037, F039, F040, F045, F046, F054, F065, F075, F087 | 26 |
| 1A-1B | E031, F023, F057 | 3 |
| 1A-1D | E034 | 1 |
| 1A-1E | E044 | 1 |
| 1A-1F | F071 | 1 |
| 1B-1A | F048, F084 | 2 |
| 1C-1A | E011 | 1 |
| 1D-1A | E036 | 1 |
| 1E-1A | F076 | 1 |
| 2A-1A | E006, E023, E030, E040, E048, F003, F020, F044, F062, F066 | 10 |
| 2A-1C | E005 | 1 |
| 2B-1A | E043 | 1 |
| 3A-1A | F015, F052, F077 | 3 |
| 3B-1A | F027 | 1 |

In one aspect, the invention relates to a monoclonal antibody, preferably to an isolated monoclonal antibody, wherein said monoclonal antibody is specifically binding influenza M2e antigen, and wherein said monoclonal antibody is a human monoclonal antibody, preferably a fully human monoclonal antibody, wherein preferably the EC50 value and/or the dissociation constant (Kd) of said monoclonal antibody and said influenza M2e antigen is at most 1000 nM, preferably at most 100 nM, more preferably at most 10 nM, still more preferably at most 1 nM, still more preferably at most 100 pM, still more preferably at most 10 pM, and most preferably at most 1 pM.

In a preferred embodiment, (i) said monoclonal antibody comprises at least one LCVR, wherein said LCVR comprises: (a) one LC CDR1, wherein said LC CDR1 consists of the peptide of any one of SEQ ID NOs 1, 2, 3, 4, 5, and 6; (b) one LC CDR2, wherein said LC CDR2 consists of the peptide of SEQ ID NO:7; (c) one LC CDR3, wherein said LC CDR3 consists of the peptide of any one of SEQ ID NOs 8, 9, 10, and 11; and/or (ii) said monoclonal antibody comprises at least one HCVR, wherein said HCVR comprises: (a) one HC CDR1, wherein said HC CDR1 consists of the peptide of SEQ ID NO:12; (b) one HC CDR2, wherein said HC CDR2 consists of the peptide of any one of SEQ ID NOs 13 and 14; and (c) one HC CDR3, wherein said HC CDR3 consists of the peptide of any one of SEQ ID NOs 15, 16, 17, 18, and 19.

In a further aspect the invention relates to an isolated monoclonal antibody, wherein said monoclonal antibody is specifically binding influenza M2e antigen, and wherein preferably said monoclonal antibody is a human monoclonal antibody, most preferably a fully human monoclonal antibody, and wherein said antibody comprises at least one antigen binding site, wherein said antigen binding site comprises: (a) one LCVR, wherein said LCVR comprises: (i) one LC CDR1, wherein said LC CDR1 consists of the peptide of any one of SEQ ID NOs 1, 2, 3, 4, 5, and 6; (ii) one LC CDR2, wherein said LC CDR2 consists of the peptide of SEQ ID NO:7; and (iii) one LC CDR3, wherein said LC CDR3 consists of the peptide of any one of SEQ ID NOs 8, 9, 10, and 11; and (b) one HCVR, wherein said HCVR comprises: (i) one HC CDR1, wherein said HC CDR1 consists of the peptide of SEQ ID NO:12; (ii) one HC CDR2, wherein said HC CDR2 consists of the peptide of any one of SEQ ID NOs 13 and 14; and (iii) one HC CDR3, wherein said HC CDR3 consists of the peptide of any one of SEQ ID NOs 15, 16, 17, 18, and 19.

A further aspect of the invention is a LCVR of a monoclonal antibody, wherein said monoclonal antibody is a human monoclonal antibody, most preferably a fully human monoclonal antibody, and wherein said monoclonal antibody is specifically binding influenza M2e antigen, and wherein said LCVR comprises: (a) one LC CDR1, wherein said LC CDR1 consists of the peptide of any one of SEQ ID NOs 1, 2, 3, 4, 5, and 6; (b) one LC CDR2, wherein said LC CDR2 consists of the peptide of SEQ ID NO:7; (c) one LC CDR3, wherein said LC CDR3 consists of the peptide of any one of SEQ ID NOs 8, 9, 10, and 11.

A further aspect of the invention is a HCVR of a monoclonal antibody, wherein said monoclonal antibody is a human monoclonal antibody, preferably a fully human monoclonal antibody, and wherein said monoclonal antibody is specifically binding influenza M2e antigen, and wherein said HCVR comprises: one HC CDR1, wherein said HC CDR1 consists of the peptide of SEQ ID NO:12; (b) one HC CDR2, wherein said HC CDR2 consists of the peptide of any one of SEQ ID NOs 13 and 14; and (c) one HC CDR3, wherein said HC CDR3 consists of the peptide of any one of SEQ ID NOs 15, 16, 17, 18, and 19.

In a further aspect, the invention relates a nucleic acid molecule encoding a HCVR or a LCVR of the invention, a monoclonal antibody of the invention or an individual chain thereof.

In a further aspect, the invention relates to an expression vector for the recombinant expression of an antibody of the invention.

In a further aspect, the invention relates to a host cell comprising at least one nucleic acid molecule or at least one expression vector of the invention.

In a further aspect, the invention relates to a pharmaceutical composition comprising at least one monoclonal antibody of the invention.

In a further aspect, the invention relates to a method of passive immunization, preferably against influenza A virus, said method comprising administering to a subject an effective amount of the monoclonal antibody of the invention or an effective amount of the pharmaceutical composition of the invention, wherein preferably said monoclonal antibody is an IgG1.

In a further aspect, the invention relates to a method of treating and/or preventing influenza A virus infection, said method comprising administering to a subject an effective amount of the monoclonal antibody of the invention or an effective amount of the pharmaceutical composition of the invention, wherein preferably said subject is a human, and wherein further preferably said monoclonal antibody is an IgG1.

In a further aspect, the invention relates to a monoclonal antibody of the invention or to the pharmaceutical composition of the invention, for use in passive immunization, preferably against influenza A virus, preferably in a human, and wherein further preferably said monoclonal antibody is an IgG1.

In a further aspect, the invention relates to the use of the monoclonal antibody of the invention in the manufacture of a medicament for the treatment and/or prophylaxis of influenza A virus infection, preferably in a human, and wherein further preferably said monoclonal antibody is an IgG1.

DESCRIPTION OF THE FIGURES

FIG. 1. Alignment of LCVR sequences (amino acids 5 to 113) of M2-specific human antibodies. Identical amino acids are shown as dots. LC CDRs 1-3 are boxed.

FIG. 2. Alignment of HCVR sequences (amino acids 7 to 121) of M2-specific human antibodies (the same antibodies as in FIG. 1). Identical amino acids are shown as dots. HC CDRs 1-3 are boxed.

DETAILED DESCRIPTION OF THE INVENTION

Figure 3:
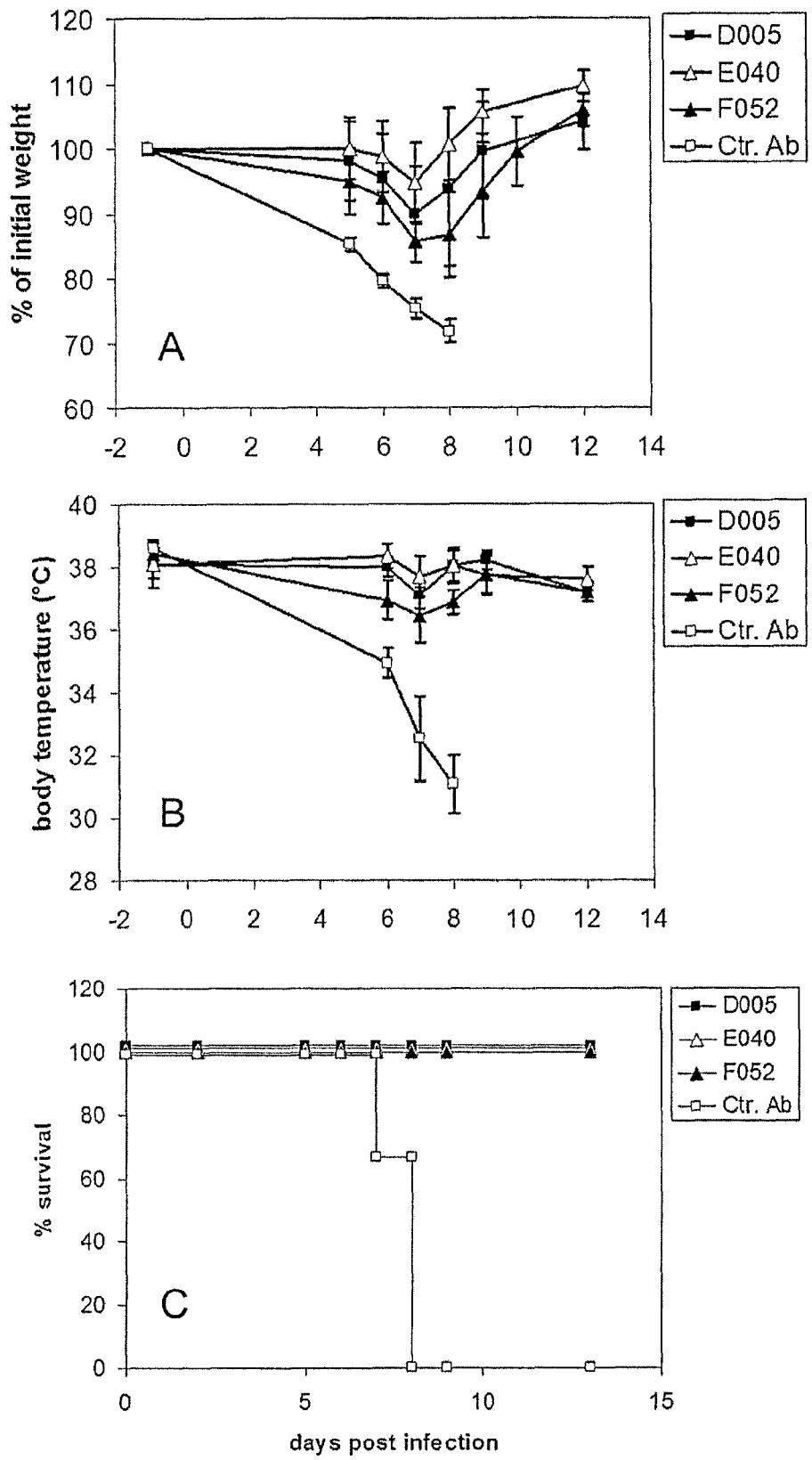
FIG. 3. Effect of M2-specific antibodies on Influenza-induced morbidity and mortality. Mice were treated with 500 µg of the indicated scFv-msFcγ2c antibody on day -2, infected with Influenza A virus PR8 on day 0, and weight (A), body temperature (B) and survival (C) were monitored on the indicated days.

"Antibody": As used herein, the term "antibody" refers to a molecule, preferably a protein, which is capable of specifically binding an antigen, typically and preferably by binding an epitope or antigenic determinant of said antigen, or a hapten. Preferably, the term antibody refers to an antigen or hapten binding molecule comprising at least one variable region, wherein preferably said molecule comprises least one HCVR and/or at least one LCVR. Further preferably, the term antibody refers to an antigen or hapten binding molecule comprising at least one, preferably exactly two antigen binding sites, wherein each of said antigen binding site(s) is formed by one HCVR and one LCVR. Furthermore, the term antibody refers to whole antibodies, preferably of the IgG, IgA, IgE, IgM, or IgD class, more preferably of the IgG class, most preferably IgG1, IgG2, IgG3, and IgG4, and to antigen binding fragments thereof. In a preferred embodiment said whole antibodies comprise either a kappa or a lambda light chain. The term "antibody" also refers to antigen or hapten binding antibody fragments, preferably to proteolytic fragments and their recombinant analogues. most preferably to Fab, Fab' and F(ab')2, and Fv. The term antibody further encompasses a protein comprising at least one, preferably two variable regions, wherein further preferably said protein comprises exactly one HCVR and exactly one LCVR. In a preferred embodiment the term antibody refers to a single chain antibody, preferably to scFv. Thus, preferred antibodies are single chain antibodies, preferably scFvs, disulfide-linked Fvs (sdFv) and fragments comprising either a light chain variable region (LCVR) or a heavy chain variable region (HCVR). In the context of the invention the term "antibody" preferably refers to recombinant antibodies, including recombinant proteins consisting of a single polypeptide, wherein said polypeptide comprises at least one, preferably exactly one, variable region. In the context of the invention recombinant antibodies may further comprise functional elements, such as, for example, a linker region, a signal peptide or hydrophobic leader sequence, a detection tag and/or a purification tag (e.g. Fc).

"recognizing": An antibody is said to be "recognizing" an epitope when said antibody is specifically binding an antigen comprising said epitope in a position which is available for interaction with said antibody, and when said antibody does not specifically bind an otherwise identical antigen which does not comprise said epitope, or wherein said epitope is located in a position which is not available for interaction with said antibody. Similarly, an antigen binding site is said to be recognizing an epitope, when an antibody comprising said antigen binding site is recognizing said epitope, wherein typically and preferably said antibody does not comprise a second antigen binding site having a different structure.

"Fv": The term Fv refers to the smallest proteolytic fragment of an antibody capable of binding an antigen or hapten and to recombinant analogues of said fragment.

"single chain antibody": A single chain antibody is an antibody consisting of a single polypeptide. Preferred single chain antibodies consist of a polypeptide comprising at least one, preferably exactly one VR, wherein preferably said VR is a HCVR. More preferred single chain antibodies consist of a polypeptide comprising a at least one, preferably exactly one, HCVR and at least one, preferably exactly one, LCVR. Still more preferred single chain antibodies comprise exactly one HCVR and exactly one LCVR. Typically and preferably said HCVR and said LCVR are forming an antigen binding site. Most preferred single chain antibodies are scFv, wherein said scFv consist of a single polypeptide comprising exactly one HCVR and exactly one LCVR, wherein said HCVR and said LCVR are linked to each other by a linker region, wherein preferably said linker region consists of at least 15, preferably of 15 to 20 amino acids (Bird et al. (1988) Science, 242 (4877):423-426). Further preferred single chain antibodies are scFv, wherein said scFv are encoded by a coding region, wherein said coding region, in 5' to 3' direction, comprises in the following order: (1) a light chain variable region (LCVR) consisting of light chain framework (LC FR) 1, complementary determining region (LC CDR) 1, LC FR2, LC CDR 2, LC FR3, LC CDR3 and LC FR4 from a κ or λ light chain; (2) a flexible linker (L), and (3) a heavy chain variable region (HCVR) consisting of framework (HC FR) 1, complementary determining region (HC CDR) 1, HC FR2, HC CDR2, HC FR3, HC CDR3 and HC FR4. Alternatively, single chain antibodies are scFv, wherein said scFv are encoded by a coding region, wherein said coding region, in 5' to 3' direction, comprises in the following order: (1) a heavy chain variable region (HCVR) consisting of framework (HC FR) 1, complementary determining region (HC CDR) 1, HC FR2, HC CDR2, HC FR3, HC CDR3 and HC FR4; (2) a flexible linker (L), and (3) a light chain variable region (LCVR) consisting of light chain framework (LC FR) 1, complementary determining region (LC CDR) 1, LC FR2, LC CDR2, LC FR3, LC DR3 and LC FR4 from a κ or λ light chain.

"diabody": The term "diabody" refers to an antibody comprising two polypeptide chains, preferably two identical polypeptide chains, wherein each polypeptide chain comprises a HCVR and a LCVR, wherein said HCVR and said LCVR are linked to each other by a linker region, wherein preferably said linker region comprises at most 10 amino acids (Huston et al. (1988), PNAS 85(16):587958-83; Holliger et al. (1993), PNAS 90(14):6444-6448, Hollinger & Hudson, 2005, Nature Biotechnology 23(9):1126-1136; Arndt et al. (2004) FEBS Letters 578(3):257-261). Preferred linker regions of diabodies comprise 0, 1, 2, 3, 4, 5, 6, 7, 8, 9, or 10 amino acids.

"human antibody": As used herein, the term "human antibody" refers to an antibody, preferably a recombinant antibody, essentially having the amino acid sequence of a human immunoglobulin, or a fragment thereof, and includes antibodies isolated from human immunoglobulin libraries. In the context of the invention "human antibodies" may comprise a limited number of amino acid exchanges as compared to the sequence of a native human antibody. Such amino acid exchanges can, for example, be caused by cloning procedures. However, the number of such amino acid exchanges in human antibodies of the invention is preferably minimized. Preferably, the amino acid sequence of human antibodies is at least 85%, preferably 90%, more preferably 95%, even more preferably at least 96%, still more preferably 97%, again still more preferably 98%, again still more preferably 99% and most preferably 100% identical to that of native human antibodies. More preferably, the amino acid sequence of human antibodies is at least 85%, preferably 90%, more preferably 95%, even more preferably at least 96%, still more preferably 97%, again still more preferably 98%, again still more preferably 99% and most preferably 100% identical to that of native human antibodies which are specifically binding to the antigen or hapten of interest. Most preferably, the amino acid sequence of human antibodies is at least 85%, preferably 90%, more preferably 95%, even more preferably at least 96%, still more preferably 97%, again still more preferably 98%, again still more preferably 99% and most preferably 100% identical to that of native human antibodies which are specifically binding influenza M2e antigen, wherein preferably said influenza M2e antigen is selected from any one of SEQ ID NOs 48 to 52, and wherein most preferably said influenza M2e antigen is SEQ ID NO:48.

Preferred recombinant human antibodies differ from native human antibodies in at most 20, 15, 10, 9, 8, 7, 6, 5, 4, 3, 2, or 1 amino acid. Very preferably, differences in the amino acid sequence of recombinant human antibodies and native human antibodies are eliminated my means of molecular cloning, and thus, most preferably, the amino acid sequence of a recombinant human antibodies and native human antibodies are identical. Such antibodies are also referred to as "fully human antibodies". An illustrative example how a fully human antibody may be obtained from a human antibody selected from a human antibody library is provided in Example 8. Typically and preferably, fully human antibodies are not immunogenic in humans.

Preferred human antibodies comprise (a) least one, preferably one, HCVR, (b) at least one, preferably one, HCCR, (c) at least one, preferably one, LCVR, and (d) at least one, preferably one, LCCR, wherein said at least one HCVR, and/or said at least one HCCR, and/or said at least one LCVR, and/or said at least one LCCR are at least 85%, preferably 90%, more preferably 95%, still more preferably at least 96%, again still more preferably 97%, again still more preferably 98%, again still more preferably 99%, and most preferably 100% identical to the respective native human regions.

It is well established that the constant regions of immunoglobulins, including human immunoglobulins, exist in various allotypes, i.e. that the amino acid sequence of said constant regions may differ to a certain extend between individuals of a population. Allotypes of the constant regions of human immunoglobulins are very well studied and the sequence information is readily available to the artisan from various sources, including the Immuno Genetics Information System. It is to be understood that different allotypes of the constant regions of one immunoglobulin are interchangeable for the purpose of the invention. For example, the human gamma 1 heavy chain of a monoclonal antibody of the invention may comprise any existing allotype of a human gamma 1 HCCR.

"monoclonal antibody": As used herein, the term "monoclonal antibody" refers to an antibody population comprising only one single antibody species, i.e. antibodies having an identical amino acid sequence.

"constant region (CR)": The term "constant region" refers to a light chain constant region (LCCR) or a heavy chain constant region (HCCR) of an antibody. Typically and preferably, said CR comprises one to four immunoglobulin domains characterized by disulfide stabilized loop structures. Preferred CRs are CRs of immunoglobulins, preferably of human immunoglobulins, wherein further preferably said immunoglobulins, preferably said human immunoglobulins are selected from the group consisting of IgG1, IgG2, IgG3, IgG4, IgA, IgE, IgM, and IgD. Very preferred CRs are human CRs comprising or consisting of an amino acid sequence available from public databases, including, for example the Immunogenetic Information System.

light chain constant region (LCCR): The LCCR, more specifically the kappa LCCR or the lambda LCCR, typically represents the C-terminal half of a native kappa or lambda light chain of an native antibody. A LCCR typically comprises about 110 amino acids representing one immunoglobulin domain.

heavy chain constant region (HCCR): The constant region of a heavy chain comprises about three quarters or more of the heavy chain of an antibody and is situated at its C-terminus. Typically, the HCCR comprises either three or four immunoglobulin domains. Preferred HCCRs are selected from gamma HCCR, alpha HCCR, epsilon HCCR, my HCCR, and delta HCCR. Very preferred are gamma HCCR, wherein preferably said gamma HCCR is selected from gamma 1 HCCR, gamma 2 HCCR, gamma 3 HCCR, and gamma 4 HCCR, wherein most preferably said gamma HCCR is a gamma 1 HCCR.

"variable region (VR)": Refers to the variable region or variable domain of an antibody, more specifically to the heavy chain variable region (HCVR) or to the light chain variable region (LCVR). Typically and preferably, a VR comprises a single immunoglobulin domain. Preferred VRs are VRs of immunoglobulins, preferably of human immunoglobulins, wherein further preferably said immunoglobulins, preferably said human immunoglobulins, are selected from the group consisting of IgG1, IgG2, IgG3, IgG4, IgA, IgE, IgM, and IgD. VRs of various species are known in the art. Preferred VRs are human VRs, wherein the framework of said human VRs exhibit at least 80%, preferably at least 85%, more preferably 90%, again more preferably at least 95%, most preferably at least 99% sequence identity with the framework of any known human VR sequence. Preferred VRs are human VRs, wherein the framework of said human VRs exhibit at least 80%, preferably at least 85%, more preferably 90%, again more preferably at least 95%, most preferably at least 99% sequence identity with the framework of any human VR sequence available from public databases, most preferably with any human VR sequence available from the Immunogenetics Information System.

Each VR comprises so called complementarity determining regions (CDRs) which are determining the binding characteristics of the antibody and which are embedded in the so called framework. Typically and preferably, VRs comprise three CDRs, preferably CDR1, CDR2, and CDR3, which are embedded into the framework (FR 1-4). Thus, in a preferred embodiment, a VR comprises the following elements in the following order from the N- to the C-terminus: FR1-CDR1-FR2-CDR2-FR3-CDR3-FR4.

Generally VRs comprise or preferably consist of a polypeptide, wherein said polypeptide is a product of a member of a family of V-gene segments in combination with further gene segments as, for example, D and J gene segments (HCVR) or J gene segments (LCDR).

"light chain variable region (LCVR)": Light chain variable regions are encoded by rearranged nucleic acid molecules and are either a kappa LCVR or a lambda LCVR. Human kappa LCVRs comprise a polypeptide, wherein said polypeptide is a product of a member of family 1 to 7 of human kappa V-gene segments. In the context of the invention preferred kappa LCVRs are human kappa LCVRs, preferably human kappa LCVRs which are encoded by a DNA which can be amplified from human B cells using a primer combination of any one of the oligonucleotides disclosed as SEQ ID NO:49 to 52 of WO2008/055795A1 with any one oligonucleotide disclosed as SEQ ID NO:53 to 56 of WO2008/055795A1, and further preferably, PCR conditions described in Example 3 or of WO2008/055795A1.

Human lambda LCVRs comprise a polypeptide, wherein said polypeptide is a product of a member of family 1 to 11 of human lambda V-gene segments. In the context of the invention preferred lambda LCVRs are human lambda LCVRs, preferably human lambda LCVRs which are encoded by a DNA which can be amplified from human B cells using a primer combination of any one of SEQ ID NO:57 to 65 of WO2008/055795A1 with any one of SEQ ID NO:66 to 68 of WO2008/055795A1, and further preferably, PCR conditions described in Example 3 of WO2008/055795A1.

Typically and preferably, LCVRs comprise three LC CDRs, preferably LC CDR1, LC CDR2, and LC CDR3, which are embedded into the light chain framework (LC FR 1-4). Thus, in a preferred embodiment, a LCVR comprises the following elements in the following order from the N- to the C-terminus: LC FR1-LC CDR1-LC FR2-LC CDR2-LC FR3-LC CDR3-LC FR4.

"heavy chain variable region (HCVR)": Heavy chain variable regions are encoded by rearranged nucleic acid molecules. Human HCVRs comprise a polypeptide, wherein said polypeptide is a product of a member of family 1 to 7 of human lambda V-gene segments. In the context of the invention preferred HCVRs are human HCVRs, preferably human HCVRs which are encoded by a DNA which can be amplified from human B cells using a primer combination of any one of SEQ ID NO:42 to 47 of WO2008/055795A1 with SEQ ID NO:48 of WO2008/055795A1 and, further preferably, PCR conditions described in Example 3 of WO2008/055795A1.

Typically and preferably, HCVRs comprise three HC CDRs, preferably HC CDR1, HC CDR2, and HC CDR3, which are embedded into the heavy chain framework (HC FR 1-4). Thus, in a preferred embodiment, a HCVR comprises the following elements in the following order from the N- to the C-terminus: HC FR1-HC CDR1-HC FR2-HC CDR2-HC FR3-HC CDR3-HC FR4.

"CDR": The complementarity determining region (CDR) 1, 2 and 3 of the HCVR and of the LCVR, respectively, of an antibody can be identified by methods generally known in the art. For the purpose of this application, CDR and FR boundaries are defined as set forth by Scavinger et al. 1999 (Exp Clin Immunogenet., Vol. 16 pp. 234-240), or by Lefranc et al. 2003 (Developmental and Comparative Immunology Vol. 27 pp. 55-77).

"antigen": As used herein, the term "antigen" refers to a molecule which is bound by an antibody. An antigen is recognized by the immune system and/or by a humoral immune response and can have one or more epitopes, preferably B-cell epitopes, or antigenic determinants.

"extracellular domain of the influenza A virus M2 protein": As used herein, the term "extracellular domain of the influenza A virus M2 protein" refers to the N-terminal extracellular domain of the M2 protein of influenza A virus, or to any consecutive stretch of at least 3, 4, 5, 6, 7, 8, 9, 10, 11, 12, 13, 14, 15, 16, 17, 18, 19, 20, 21, 22, or 23, amino acids thereof. Preferably, extracellular domain of the influenza A virus M2 protein refers to amino acid residues 2 to 24 of the influenza A virus M2 protein, or to any consecutive stretch of at least of at least 3, 4, 5, 6, 7, 8, 9, 10, 11, 12, 13, 14, 15, 16, 17, 18, 19, 20, 21, or 22 amino acids thereof. In a more preferred embodiment the extracellular domain of the influenza A virus M2 protein comprises or consists of a peptide selected from any one of SEQ ID NOs 48 to 83 and 90 to 92, or to any consecutive stretch of at least of at least 3, 4, 5, 6, 7, 8, 9, 10, 11, 12, 13, 14, 15, 16, 17, 18, 19, 20, 21, or 22 amino acids thereof. In a very preferred embodiment the extracellular domain of the influenza A virus M2 protein comprises or consists of a peptide selected from any one of SEQ ID NOs 48 to 50. Most preferably, the extracellular domain of the influenza A virus M2 protein is the M2e consensus sequence (SEQ ID NO:48).

TABLE 4

Variants of the extracellular domain of influenza A virus M2 protein.
Sequences are shown without the N-terminal Methionine.

| Influenza A M2e variant | aa Sequence | SEQ ID NO |
|---|---|---|
| aa 2-24 of SEQ ID NO: 84 (PR8) | SLLTEVETPIRNEWGCRCNGSSD | 51 |
| M2-T: | SLLTEVETPTRNEWGCRCNDSSD | 52 |
| M2e consensus | SLLTEVETPIRNEWGCRCNDSSD | 48 |
| M2e-short | SLLTEVETPIRNEWGC | 49 |
| M2-KE: | SLLTEVETPTKNEWECRCNDSSD | 53 |
| M2-K: A/Wisconsin/3523/88(H1N1) | SLLTEVETPIRNEWGCKCNDSSD | 54 |
| M2-E: | SLLTEVETPIRNEWECRCNDSSD | 55 |
| M2-GE: | SLLTEVETPIRNGWECRCNDSSD | 56 |
| M2-S: | SLLTEVETPIRSEWGCRCNDSSD | 57 |
| M2-FP: | SFLPEVETPIRNEWGCRCNDSSD | 58 |
| M2-DSSN: | SLLTEVETPIRNEWGCRCNDSSN | 59 |
| M2-K: | SLLTEVETPIRKEWGCRCNDSSD | 61 |
| M2-F: | FLLTEVETPIRNEWGCRCNDSSD | 62 |
| M2-EG: A/NewYork/687/1995/(H3N2) | SLLTEVETPIRNEWECRCNGSSD | 63 |
| M2-PS: | SLPTEVETPIRSEWGCRCNDSSD | 64 |
| M2-P: | SLLPEVETPIRNEWGCRCNDSSD | 65 |
| M2-PG: | SLLPEVETPIRNGWGCRCNDSSD | 66 |
| M2-TGE: A/DK/ST/5048/2001 (H3N8) | SLLTEVETPTRNGWECRCNDSSD | 67 |
| M2-FG: A/X-31 (H3N2) | SFLTEVETPIRNEWGCRCNGSSD | 68 |
| M2-EYS: | SLLTEVETPIRNEWEYRCSDSSD | 69 |
| M2-LTGS: A/HK/156/97 (H9N2) | SLLTEVETLTRNGWGCRCSDSSD | 70 |
| M2-LTKGS: A/HK/542/97 (H5N1) | SLLTEVETLTKNGWGCRCSDSSD | 71 |
| M2-HTES: | SLLTEVETHTRNEWECRCNDSSD | 72 |
| M2-TES: A/VN/1203/2004 (H5N1) M2e-VN | SLLTEVETPTRNEWECRCSDSSD | 50 |
| M2-TGEK: A/Neth/33/03 (H7N1) | SLLTEVETPTRNGWECKCNDSSD | 73 |
| M2-FLTGEKS: | SFLTEVETLTRNGWECRCSDSSD | 74 |
| M2-LTGEKS: A/HK/1074/99 (H9N2) | SLLTEVETLTRNGWECKCSDSSD | 75 |
| M2-DLTGS: A/HK/485/97/(H5N1) | SLLTEVDTLTRNGWGCRCSDSSD | 76 |
| M2-TGS: A/chicken/SH/F/98/(H9N2) | SLLTEVETPTRNGWGCRCSDSSD | 77 |
| M2-KTGEKS: A/Quail/AR/16309-7/94 (H7N3NSA) | SLLTEVKTPTRNGWECKCSDSSD | 78 |
| M2-TDGEKS: A/Chick/Pen/13552-1/98(H7N2NSB) | SLLTEVETPTRDGWECKCSDSSD | 79 |
| M2-HTGEKS: A/Chick/CA/1002a/00 (H6N2) | SLLTEVETHTRNGWECKCSDSSD | 80 |
| M2-P: A/swine/Quebec/192/81/(H1N1) | SLPTEVETPIRNEWGCRCNDSSD | 81 |
| M2-SG: A/swine/Tenn/25/77/(H1N1) | SLLTEVETPIRSEWGCRCNDSGD | 82 |
| M2-KGENS: A/Turkey/VA/158512/02 (H7N2) | SLLTEVETPIRKGWECNCSDSSD | 83 |

TABLE 4 -continued

Variants of the extracellular domain of influenza A virus M2 protein.
Sequences are shown without the N-terminal Methionine.

| Influenza A M2e variant | aa Sequence | SEQ ID NO |
|---|---|---|
| M2TGEKS: A/Canada/rv504/2004 (H7N3) | SLLTEVETPTRNGWECKCSDSSD | 90 |
| M2GHTGKS: A/chicken/HongKong/SF1/03 (H9N2) | SLLTGVETHTRNGWGCKCSDSSD | 91 |
| M2PHTGS: A/chicken/HongKong/YU427/03 (H9N2) | SLLPEVETHTRNGWGCRCSDSSD | 92 |

"influenza M2e antigen": As used herein the expression "influenza M2e antigen" refers to an antigen comprising at least one epitope of the extracellular domain of the influenza A virus M2 protein. In a preferred embodiment, the term influenza M2e antigen refers to an antigen comprising at least one epitope of any one of the peptides of SEQ ID NOs 48 to 83 and 90 to 92. More preferably, the term influenza M2e antigen refers to an antigen comprising or consisting of the extracellular domain of the influenza A M2 protein. Still more preferably, the term influenza M2e antigen refers to an antigen comprising or consisting of the peptide of any one of SEQ ID NOs 48 to 83 and 90 to 92, or to any consecutive stretch of at least of at least 3, 4, 5, 6, 7, 8, 9, 10, 11, 12, 13, 14, 15, 16, 17, 18, 19, 20, 21, or 22 amino acids thereof. In a very preferred embodiment, the influenza M2e antigen comprises or preferably consists of the peptide of any one of SEQ ID NOs 48 to 50. Most preferably, said influenza M2e antigen comprises or preferably consists of the M2e consensus sequence (SEQ ID NO:48).

The term "influenza M2e antigen" also includes conjugates, fusion or coupling products comprising at least one epitope of the extracellular domain of the influenza A virus M2 protein. This includes conjugates of the extracellular domain of the influenza A virus M2 protein with a carrier, wherein preferably said carrier is RNAse A. In particular, the term "influenza M2e antigen" also includes virus-like particles, preferably virus like particles of RNA bacteriophages, wherein an extracellular domain of the influenza A virus M2 protein is coupled to said virus like particle, preferably to said virus-like particle of a RNA bacteriophage. Preferred virus-like particles are virus-like particles of RNA bacteriophages Qβ or AP205, most preferably of RNA bacteriophage Qβ. A very preferred influenza M2e antigen is a virus-like particle of RNA bacteriophage Qβ, wherein the peptide of SEQ ID NO:48 is coupled to said virus-like particle, wherein preferably said peptide is coupled to said virus-like particle by means of a covalent non-peptide bond. The term influenza M2e antigen also includes fusion proteins comprising the extracellular domain of the influenza A virus M2 protein or at least one epitope thereof. In particular, the term influenza M2e antigen includes fusion proteins comprising a peptide of any one of SEQ ID NOs 48 to 83 and 90 to 92. Preferred fusion proteins are chimeric proteins, wherein said chimeric proteins comprise an extracellular domain of a first influenza A virus M2 protein and the transmembrane- and intercellular domain of a second influenza A virus M2 protein. A very preferred chimeric protein is the protein of SEQ ID NO:85.

Furthermore, the term influenza M2e antigen includes virus particles or virus-like particles comprising the extracellular domain of the influenza A virus M2 protein or at least one epitope thereof. Thus, influenza M2e antigen also refers to influenza virus particles or influenza virus-like particles, preferably to influenza A virus particles or influenza A virus-like particles.

In a preferred embodiment, the term influenza M2e antigen refers to cells, preferably to eukaryotic cells, comprising the extracellular domain of the influenza A virus M2 protein on their cell surface. This includes cells which are infected by influenza virus, preferably by influenza A virus. This also includes stably transformed or transfected cells expressing a recombinant protein, wherein said protein comprises the extracellular domain of the influenza A virus M2 protein or at least one epitope thereof, and wherein preferably said recombinant protein comprises a domain which allows the integration of said recombinant protein into the cell membrane. Preferred recombinant proteins in this context are influenza A M2 proteins or chimeric proteins, wherein said chimeric proteins comprise an extracellular domain of a first influenza A virus M2 protein and the transmembrane- and intercellular domain of a second influenza A virus M2 protein. In a preferred embodiment said recombinant protein is the protein of any one of SEQ ID NOs 84 or 85, preferably SEQ ID NO:84, wherein further preferably the N-terminal methionine residue of said recombinant proteins is cleaved off.

In a further preferred embodiment influenza M2e antigen refers to a eukaryotic cell, preferably to a L929 cell or to a 293T cell, wherein said cell is expressing a recombinant protein, wherein said protein comprises the extracellular domain of the influenza A virus M2 protein or at least one epitope thereof, and wherein preferably said recombinant protein comprises a domain which allows the integration of said recombinant protein into the cell membrane. Preferred recombinant proteins in this context are influenza A M2 proteins or chimeric proteins, wherein said chimeric proteins comprise an extracellular domain of a first influenza A virus M2 protein and the transmembrane- and intercellular domain of a second influenza A virus M2 protein. In a preferred embodiment said recombinant protein is the protein of any one of SEQ ID NOs 84 or 85, wherein further preferably the N-terminal methionine residue of said recombinant proteins is cleaved off.

"specifically binding": The specificity of an antibody relates to the antibody's capability of specifically binding an antigen. The specificity of this interaction between the antibody and the antigen (affinity) is characterized by a binding constant or, inversely, by a dissociation constant (Kd). It is to be understood that the apparent affinity of an antibody to an antigen depends on the structure of the antibody and of the antigen, and on the actual assay conditions. The apparent affinity of an antibody to an antigen in a multivalent interaction may be significantly higher than in a monovalent interaction due to avidity. Thus, affinity is preferably determined under conditions favoring monovalent interactions. Kd can be determined by methods known in the art. Preferably, Kd of a given combination of antibody and antigen is determined by Friguet ELISA essentially as described (Friguet B. et al., 1985, J. Immunol. Meth. 77, 305-319), wherein a constant amount of purified antibody, for example scFv or Fab fragment, is contacted with a serial dilution of a known concentration of antigen.

Very preferably, Kd of an antibody and an antigen in solution is determined by Friguet ELISA, wherein preferably said antibody is an scFv antibody, most preferably a scFv-msFcγ2c fusion, and wherein further preferably said antigen is an influenza M2e antigen, and wherein still more preferably said influenza M2e antigen comprises or consists of the peptide of any one of SEQ ID NOs 48 to 83 and 90 to 92, most preferably of the peptide of SEQ ID NO:48. In one embodiment, said influenza M2e antigen is a conjugate of RNAse-A and of the peptide of SEQ ID NO:48. In a preferred embodiment said Friguet-ELISA is performed under conditions essentially as described in Example 11 herein. In a very preferred embodiment said Friguet-ELISA is performed under conditions essentially as described in Example 11, wherein said influenza M2e antigen is in solution, and wherein said influenza M2e antigen is SEQ ID NO:48. The affinity of a given combination of antibody and antigen may also be determined by ELISA, wherein a constant amount of immobilized antigen is contacted with a serial dilution of a known concentration of a purified antibody, preferably a scFv or Fab fragment. The affinity is then determined as the concentration of the antibody where half-maximal binding is observed (EC50). Very preferably, EC50 of an antibody and an immobilized antigen is determined by ELISA, wherein preferably said antibody is an scFv antibody, most preferably a scFv-msFcγ2c fusion, and wherein further preferably said antigen is an influenza M2e antigen, wherein preferably said influenza M2e antigen comprises or preferably consists of the peptide of any one of SEQ ID NOs 48 to 83, most preferably of the peptide of SEQ ID NO:48. Most preferably, said influenza M2e antigen is a conjugate of RNAse-A and of the peptide of SEQ ID NO:48. In a very preferred embodiment said ELISA is performed as described in the first paragraph of Example 4 herein. Alternatively, Kd of an interaction of an antibody and an antigen is determined by Biacore analysis as the ratio of on rate ($k_{on}$) and off rate ($k_{off}$). Kd may also be determined by equilibrium dialysis.

Lower values of Kd indicate a more specific binding of the antibody to the antigen than higher values. In the context of the application, an antibody is considered to be "specifically binding an antigen", when the dissociation constant (Kd) as determined by Friguet ELISA as described above is at most 10 nM ($<=10^{-8}$ M), preferably at most 1 nM ($<=10^{-9}$ M), more preferably at most 100 ($<=10^{-10}$ M), still more preferably at most 10 pM ($<=_{10}{-11}$ M) most preferably at most 1 pM ($<=10^{-12}$ M). Very preferred are antibodies capable of binding an antigen with a Kd of less than 20 pM, wherein further preferably said Kd is determined in solution. In the context of the application, an antibody is further considered to be "specifically binding an antigen", when the EC50, preferably determined as described above is at most 1000 nM ($<=10^{-6}$ M), preferably at most 100 nM ($<=10^{-7}$ M), more preferably at most 10 nM ($<=10^{-8}$ M), still more preferably at most 1 nM ($<=10^{-9}$M), still more preferably at most 100 pM ($<=10^{-10}$ M), still more preferably at most 10 pM ($<=10^{-11}$ M) and most preferably at most 1 pM ($<=10^{-12}$ M). Very preferred are antibodies capable of binding an antigen with a EC50 of less than 100 pM, wherein further preferably said EC50 is determined with immobilized antigen. In this context, Kd and/or EC50 values are referred to as being in the "low picomolar range" when these values are below 100 pM.

The affinity of an antibody to influenza M2e antigen may also be determined in an experimental set-up, wherein said influenza M2e antigen is a cell, typically and preferably a living cell, and wherein said cell comprises the extracellular domain of the influenza A virus M2 protein or an epitope thereof on the cell surface. The affinity of an antibody to a cell is preferably determined by FACS technology, preferably in an experimental set-up essentially as disclosed in Examples 5 and 9 herein. It is to be understood that the EC50 values for a specific combination of antibody and cells are comparable only within the same experimental set-up relative to a control antibody. An antibody is regarded as specifically binding an influenza M2e antigen, wherein said influenza M2e antigen is a cell, when the EC50 value for the interaction between a control antibody and said influenza M2e antigen is at least $10^3$-fold, preferably at least $10^4$-fold, more preferably at least $10^5$-fold, and most preferably at least $10^6$-fold higher than the EC50 value for the interaction between said antibody and said influenza M2e antigen.

"effective amount": A therapeutically effective amount of a monoclonal antibody of the invention or of a pharmaceutical composition of the invention generally refers to an amount necessary to achieve, at dosages and periods of time necessary, the desired therapeutic result, wherein preferably said result is preventing, reducing or ameliorating infection with influenza virus, preferably with influenza A virus. With respect to a therapeutic treatment of a human, an "effective amount" typically refers to an amount of 1 mg to 1000 mg, preferably 10 mg to 500 mg, more preferably 10 mg to 300 mg, still more preferably 50 mg to 200 mg, and most preferably about 100 mg of said monoclonal antibody.

"Tag": The term tag, preferably a purification or detection tag, refers to a polypeptide segment that can be attached to a second polypeptide to provide for purification or detection of the second polypeptide or provides sites for attachment of the second polypeptide to a substrate. In principle, any peptide or protein for which an antibody or other specific binding agent is available can be used as an affinity tag. Tags include haemagglutinin tag, myc tag, poly-histidine tag, protein A, glutathione S transferase, Glu-Glu affinity tag, substance P, FLAG peptide, streptavidin binding peptide, or other antigenic epitope or binding domain (mostly taken from U.S. Ser. No. 06686168).

A library-based screening method for the identification, isolation and cloning of scFv specifically binding an antigen of interest is disclosed in WO2008/055795A1. In particular, said method allows for the identification, isolation and cloning of human scFv and for the subsequent generation of fully human antibodies, including Fab fragments and whole IgG. Applying said technology, human monoclonal antibodies specifically binding influenza M2e antigen have been identified and cloned.

In one aspect, the invention provides a monoclonal antibody, preferably an isolated monoclonal antibody, specifically binding influenza M2e antigen, wherein said monoclonal antibody is a human monoclonal antibody, preferably a fully human monoclonal antibody. In a preferred embodiment said monoclonal antibody is a recombinant monoclonal antibody.

In a preferred embodiment said human monoclonal antibody, preferably said fully human monoclonal antibody, is not recognized by the human immune system.

The specificity of an antibody is mainly determined by the amino acid sequence of the complementarity determining regions (CDRs) in the heavy chain variable regions (HCVR) of said antibody and/or by the CDRs in the light chain variable regions said antibody (LCVR). The invention discloses CDRs of HCVRs (HC CDRs) and CDRs of the LCVRs (LC CDRs) of monoclonal antibodies, wherein said monoclonal antibodies are capable of specifically binding influenza A M2, and wherein typically and preferably said HCVRs and said LCVRs are forming an antigen binding site.

It has surprisingly been found that the monoclonal antibodies of the invention which are capable of specifically binding influenza M2e antigen share identical or closely related HC CDRs and/or LC CDRs in different combinations, wherein the closely related HC CDRs and/or LC CDRs differ in at most a few amino acid residues (cf. Tables 1-3). It is therefore concluded that all antibodies of Tables 1-3 are clonally related.

Thus, in one embodiment said monoclonal antibody comprises (i) at least one, preferably exactly one, LCVR, wherein said LCVR comprises: (a) one LC CDR1, wherein said LC CDR1 consists of the peptide of any one of SEQ ID NOs 1, 2, 3, 4, 5, and 6, and wherein preferably said LC CDR1 is located at CDR1 position within the framework of said LCVR; (b) one LC CDR2, wherein said LC CDR2 consists of the peptide of SEQ ID NO:7, and wherein preferably said LC CDR2 is located at CDR2 position within the framework of said LCVR; (c) one LC CDR3, wherein said LC CDR3 consists of the peptide of any one of SEQ ID NOs 8, 9, 10, and 11, and wherein preferably said LC CDR3 is located at CDR3 position within the framework of said LCVR; and/or said monoclonal comprises (ii) at least one, preferably exactly one HCVR, wherein said HCVR comprises: (a) one HC CDR1, wherein said HC CDR1 consists of the peptide of SEQ ID NO:12, and wherein preferably said HC CDR1 is located at CDR1 position within the framework of said HCVR; (b) one HC CDR2, wherein said HC CDR2 consists of the peptide of any one of SEQ ID NOs 13 and 14, and wherein preferably said HC CDR2 is located at CDR2 position within the framework of said HCVR; and (c) one HC CDR3, wherein said HC CDR3 consists of the peptide of any one of SEQ ID NOs 15, 16, 17, 18, and 19, and wherein preferably said HC CDR3 is located at CDR3 position within the framework of said HCVR.

In a further embodiment said monoclonal antibody comprises (i) at least one, preferably exactly one, LCVR, wherein said LCVR comprises: (a) one LC CDR1, wherein said LC CDR1 consists of the peptide of any one of SEQ ID NOs 1, 2, 3, 4, 5, and 6; (b) one LC CDR2, wherein said LC CDR2 consists of the peptide of SEQ ID NO:7; (c) one LC CDR3, wherein said LC CDR3 consists of the peptide of any one of SEQ ID NOs 8, 9, 10, and 11; and wherein said monoclonal comprises (ii) at least one, preferably exactly one HCVR, wherein said HCVR comprises: (a) one HC CDR1, wherein said HC CDR1 consists of the peptide of SEQ ID NO:12; (b) one HC CDR2, wherein said HC CDR2 consists of the peptide of any one of SEQ ID NOs 13 and 14; and (c) one HC CDR3, wherein said HC CDR3 consists of the peptide of any one of SEQ ID NOs 15, 16, 17, 18, and 19.

Typically and preferably, said monoclonal antibody comprises exactly one LCVR and exactly one HCVR, which are preferably forming an antigen binding site. In case of an antibody in the IgG format, said monoclonal antibody comprises exactly two LCVR and exactly two HCVR. However, the antibody of the invention may also comprise or alternatively consist of only one LCVR or of only one HCVR. Thus, in a further preferred embodiment said monoclonal antibody comprises or alternatively consists of at least one, preferably exactly one, LCVR, wherein said LCVR comprises: (a) one LC CDR1, wherein said LC CDR1 consists of the peptide of any one of SEQ ID NOs 1, 2, 3, 4, 5, and 6; (b) one LC CDR2, wherein said LC CDR2 consists of the peptide of SEQ ID NO:7; (c) one LC CDR3, wherein said LC CDR3 consists of the peptide of any one of SEQ ID NOs 8, 9, 10, and 11.

In a further preferred embodiment said monoclonal antibody comprises or alternatively consists of at least one, preferably exactly one HCVR, wherein said HCVR comprises: (a) one HC CDR1, wherein said HC CDR1 consists of the peptide of SEQ ID NO:12; (b) one HC CDR2, wherein said HC CDR2 consists of the peptide of any one of SEQ ID NOs 13 and 14; and (c) one HC CDR3, wherein said HC CDR3 consists of the peptide of any one of SEQ ID NOs 15, 16, 17, 18, and 19.

Typically and preferably the antibodies of the invention comprise at least on antigen binding site comprising one LCVR and one HCVR, wherein said antigen binding site recognizes an epitope of influenza A M2e antigen. One aspect of the invention therefore is an isolated monoclonal antibody, wherein said monoclonal antibody is specifically binding influenza M2e antigen, and wherein preferably said monoclonal antibody is a human monoclonal antibody, more preferably a fully human monoclonal antibody, and wherein said antibody comprises at least one antigen binding site, wherein said antigen binding site comprises: (a) one LCVR, wherein said LCVR comprises: (i) one LC CDR1, wherein said LC CDR1 consists of the peptide of any one of SEQ ID NOs 1, 2, 3, 4, 5, and 6; (ii) one LC CDR2, wherein said LC CDR2 consists of the peptide of SEQ ID NO:7; and (iii) one LC CDR3, wherein said LC CDR3 consists of the peptide of any one of SEQ ID NOs 8, 9, 10, and 11; and (b) one HCVR, wherein said HCVR comprises: (i) one HC CDR1, wherein said HC CDR1 consists of the peptide of SEQ ID NO:12; (ii) one HC CDR2, wherein said HC CDR2 consists of the peptide of any one of SEQ ID NOs 13 and 14; and (iii) one HC CDR3, wherein said HC CDR3 consists of the peptide of any one of SEQ ID NOs 15, 16, 17, 18, and 19.

Based on sequence similarities between the amino acid sequences of LC CDR1 and LC CDR3 three closely relates groups of antibodies can be distinguished (cf. Table 1). Thus, in one embodiment said LCVR comprises: (a) one LC CDR1, wherein said LC CDR1 consists of the peptide of any one of SEQ ID NOs 1, 2, and 3; (b) one LC CDR2, wherein said LC CDR2 consists of the peptide of SEQ ID NO:7; (c) one LC CDR3, wherein said LC CDR3 consists of the peptide of any one of SEQ ID NOs 8, 9 and 10; and wherein preferably said HCVR comprises: (a) one HC CDR1, wherein said HC CDR1 consists of the peptide of SEQ ID NO:12; (b) one HC CDR2, wherein said HC CDR2 consists of the peptide of any one of SEQ ID NOs 13 and 14; and (c) one HC CDR3, wherein said HC CDR3 consists of the peptide of any one of SEQ ID NOs 15, 16, 17, 18, and 19.

In a further embodiment LCVR comprises: (a) one LC CDR1, wherein said LC CDR1 consists of the peptide of any one of SEQ ID NOs 4 and 5; (b) one LC CDR2, wherein said LC CDR2 consists of the peptide of SEQ ID NO:7; (c) one LC CDR3, wherein said LC CDR3 consists of the peptide of SEQ ID NO:8; and wherein preferably said HCVR comprises: (a) one HC CDR1, wherein said HC CDR1 consists of the peptide of SEQ ID NO:12; (b) one HC CDR2, wherein said HC CDR2 consists of the peptide of any one of SEQ ID NOs 13 and 14; and (c) one HC CDR3, wherein said HC CDR3 consists of the peptide of any one of SEQ ID NOs 15, 16, 17, 18, and 19.

In a further embodiment, said LCVR comprises: (a) one LC CDR1, wherein said LC CDR1 consists of the peptide of any one of SEQ ID NOs 1 and 6; (b) one LC CDR2, wherein said LC CDR2 consists of the peptide of SEQ ID NO:7; (c) one LC CDR3, wherein said LC CDR3 consists of the peptide of SEQ ID NO:8 and 11; and wherein preferably said HCVR comprises: (a) one HC CDR1, wherein said HC CDR1 consists of the peptide of SEQ ID NO:12; (b) one HC CDR2, wherein said HC CDR2 consists of the peptide of any one of SEQ ID NOs 13 and 14; and (c) one HC CDR3, wherein said HC CDR3 consists of the peptide of any one of SEQ ID NOs 15, 16, 17, 18, and 19.

Among the antibodies of the invention nine different types of LCVRs were identified comprising different combinations of LC CDR sequences (cf. Table 1). Thus, in a preferred embodiment said LCVR is selected from: (a) a LCVR, wherein (i) said LC CDR1 consists of the peptide of SEQ ID NO:1, (ii) said LC CDR2 consists of the peptide of SEQ ID NO:7, and (iii) said LC CDR3 consists of the peptide of SEQ ID NO:8; (b) a LCVR, wherein (i) said LC CDR1 consists of the peptide of SEQ ID NO:2, (ii) said LC CDR2 consists of the peptide of SEQ ID NO:7, and (iii) said LC CDR3 consists of the peptide of SEQ ID NO:8; (c) a LCVR, wherein (i) said LC CDR1 consists of the peptide of SEQ ID NO:3, (ii) said LC CDR2 consists of the peptide of SEQ ID NO:7, and (iii) said LC CDR3 consists of the peptide of SEQ ID NO:8; (d) a LCVR, wherein (i) said LC CDR1 consists of the peptide of SEQ ID NO:1, (ii) said LC CDR2 consists of the peptide of SEQ ID NO:7, and (iii) said LC CDR3 consists of the peptide of SEQ ID NO:9; (e) a LCVR, wherein (i) said LC CDR1 consists of the peptide of SEQ ID NO:1, (ii) said LC CDR2 consists of the peptide of SEQ ID NO:7, and (iii) said LC CDR3 consists of the peptide of SEQ ID NO:10; (f) a LCVR, wherein (i) said LC CDR1 consists of the peptide of SEQ ID NO:4, (ii) said LC CDR2 consists of the peptide of SEQ ID NO:7, and (iii) said LC CDR3 consists of the peptide of SEQ ID NO:8; (g) a LCVR, wherein (i) said LC CDR1 consists of the peptide of SEQ ID NO:5, (ii) said LC CDR2 consists of the peptide of SEQ ID NO:7, and (iii) said LC CDR3 consists of the peptide of SEQ ID NO:8; (h) a LCVR, wherein (i) said LC CDR1 consists of the peptide of SEQ ID NO:6, (ii) said LC CDR2 consists of the peptide of SEQ ID NO:7, and (iii) said LC CDR3 consists of the peptide of SEQ ID NO:8; and (i) a LCVR, wherein (i) said LC CDR1 consists of the peptide of SEQ ID NO:1, (ii) said LC CDR2 consists of the peptide of SEQ ID NO:7, and (iii) said LC CDR3 consists of the peptide of SEQ ID NO:11.

Among the antibodies of the invention the most abundant combinations of LC CDRs are types 1A, 1A and 3A (cf. Table 1). Thus, in a preferred embodiment said LCVR is selected from: (a) a LCVR, wherein (i) said LC CDR1 consists of the peptide of SEQ ID NO:1, (ii) said LC CDR2 consists of the peptide of SEQ ID NO:7, and (iii) said LC CDR3 consists of the peptide of SEQ ID NO:8; (b) a LCVR, wherein (i) said LC CDR1 consists of the peptide of SEQ ID NO:4, (ii) said LC CDR2 consists of the peptide of SEQ ID NO:7, and (iii) said LC CDR3 consists of the peptide of SEQ ID NO:8; and (c) a LCVR, wherein (i) said LC CDR1 consists of the peptide of SEQ ID NO:6, (ii) said LC CDR2 consists of the peptide of SEQ ID NO:7, and (iii) said LC CDR3 consists of the peptide of SEQ ID NO:8. In a very preferred embodiment, said LCVR is selected from: (a) a LCVR, wherein (i) said LC CDR1 consists of the peptide of SEQ ID NO:1, (ii) said LC CDR2 consists of the peptide of SEQ ID NO:7, and (iii) said LC CDR3 consists of the peptide of SEQ ID NO:8.

Antibodies obtained from library screening may differ from fully human antibodies in certain amino acid positions of the VRs due to cloning artifacts, wherein typically these positions are located near the N- and/or C-terminus of the variable region. Preferably, these artifacts are removed from the antibody in order to obtain fully human antibodies. For example, in order to obtain fully human LCVRs, position 1 to 4 of the LCVRs is replaced by SEQ ID NO:24. Thus, in a preferred embodiment position 1 to 4 of said LCVR consists of SEQ ID NO:24.

Figure 1:
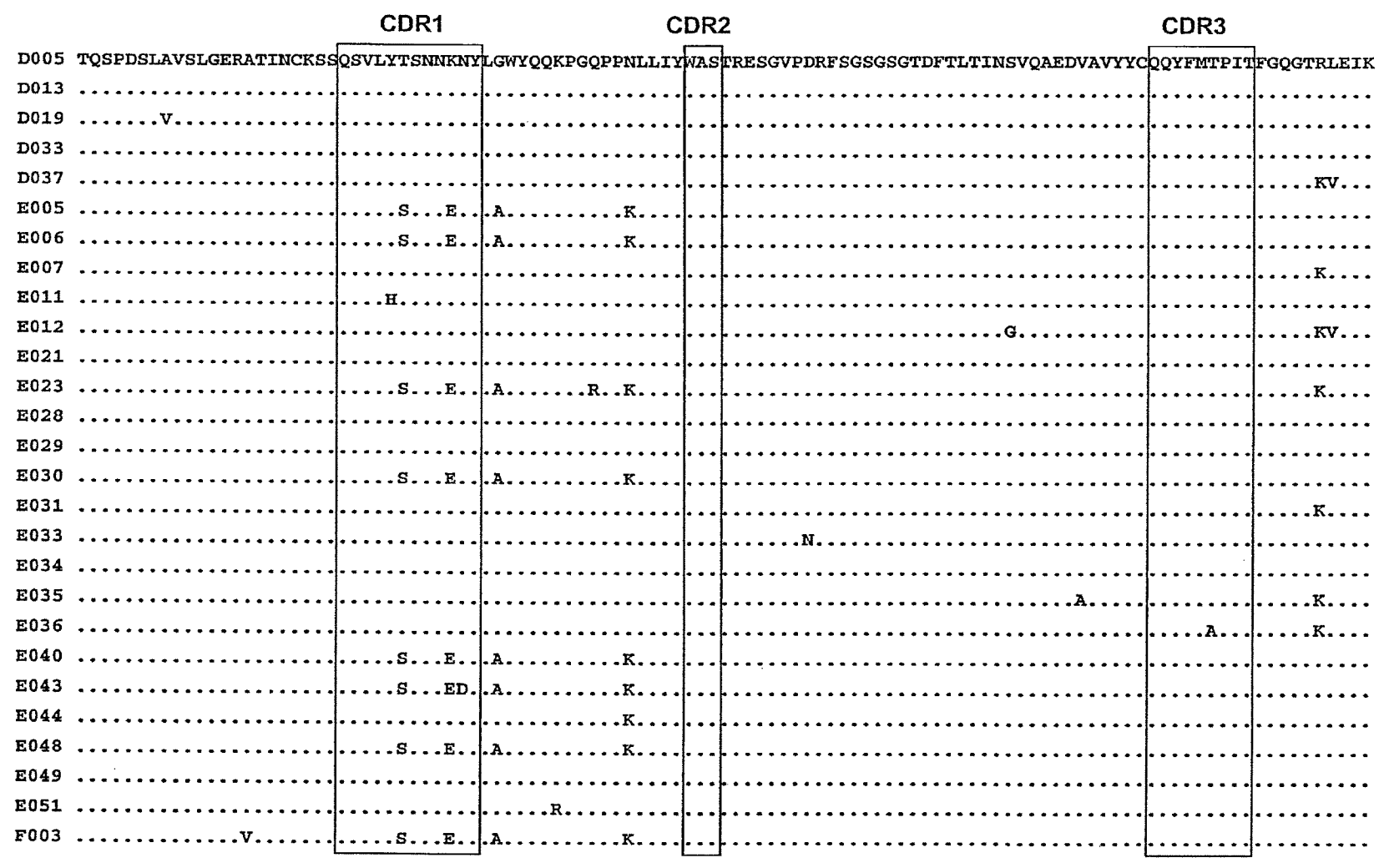

In a preferred embodiment said LCVR comprises or preferably consists of any one of the amino acid sequences depicted in FIG. 1. In a further preferred embodiment position 5 to 113 of said LCVR consists of the peptide of any one of SEQ ID NOs 20, 21 and 22, wherein preferably position 1 to 4 of said LCVR consists of the peptide of SEQ ID NO:24.

In a further preferred embodiment position 5 to 113 of said LCVR consists of a peptide, wherein said peptide is encoded by the nucleic acid sequence of any one of SEQ ID NOs 86, 87, and 88, wherein preferably position 1 to 4 of said LCVR consists of the peptide of SEQ ID NO:24.

Furthermore, among the antibodies of the invention six different types of HCVRs were identified comprising different combinations of HC CDR sequences (cf. Table 2). Thus, in a preferred embodiment said HCVR is selected from: (a) a HCVR, wherein (i) said HC CDR1 consists of the peptide of SEQ ID NO:12, (ii) said HC CDR2 consists of the peptide of SEQ ID NO:13, and (iii) said HC CDR3 consists of the peptide of SEQ ID NO:15; (b) a HCVR, wherein (i) said HC CDR1 consists of the peptide of SEQ ID NO:12, (ii) said HC CDR2 consists of the peptide of SEQ ID NO:13, and (iii) said HC CDR3 consists of the peptide of SEQ ID NO:16; (c) a HCVR, wherein (i) said HC CDR1 consists of the peptide of SEQ ID NO:12, (ii) said HC CDR2 consists of the peptide of SEQ ID NO:13, and (iii) said HC CDR3 consists of the peptide of SEQ ID NO:17; (d) a HCVR, wherein (i) said HC CDR1 consists of the peptide of SEQ ID NO:12, (ii) said HC CDR2 consists of the peptide of SEQ ID NO:13, and (iii) said HC CDR3 consists of the peptide of SEQ ID NO:18; (e) a HCVR, wherein (i) said HC CDR1 consists of the peptide of SEQ ID NO:12, (ii) said HC CDR2 consists of the peptide of SEQ ID NO:14, and (iii) said HC CDR3 consists of the peptide of SEQ ID NO:15; and (f) a HCVR, wherein (i) said HC CDR1 consists of the peptide of SEQ ID NO:12, (ii) said HC CDR2 consists of the peptide of SEQ ID NO:13, and (iii) said HC CDR3 consists of the peptide of SEQ ID NO:19.

Among the antibodies of the invention the most abundant combination of HC CDRs is type 1A (cf. Table 2). Thus, in a preferred embodiment said HCVR is selected from: (a) a HCVR, wherein (i) said HC CDR1 consists of the peptide of SEQ ID NO:12, (ii) said HC CDR2 consists of the peptide of SEQ ID NO:13, and (iii) said HC CDR3 consists of the peptide of SEQ ID NO:15;

In order to remove cloning artifacts and to obtain fully human HCVRs, typically and preferably position 1 to 6 of the HCVRs is replaced by SEQ ID NO:25. Thus, in a preferred embodiment position 1 to 6 of said HCVR consists of SEQ ID NO:25.

In a preferred embodiment said HCVR comprises or preferably consists of any one of the amino acid sequences depicted in FIG. 2. In a further preferred embodiment position 7 to 121 of said HCVR consists of the peptide of SEQ ID NO:23, wherein preferably position 1 to 6 of said HCVR consists of the peptide of SEQ ID NO:25. In a further preferred embodiment position 7 to 121 of said HCVR consists of a peptide, wherein said peptide is encoded by the nucleic acid sequence of SEQ ID NO:89, wherein preferably position 1 to 6 of said HCVR consists of the peptide of SEQ ID NO:25.

Among the antibodies of the invention fourteen different combinations of LC CDRs and HC CDRs were identified (cf. Table 2). Thus in one embodiment said monoclonal antibody comprises at least one, preferably exactly one antigen binding site, wherein the combination of LC CDRs and HC CDRs is selected from any one of the combinations of Table 3. Preferably said combination is chosen from one of the most abundant combinations 1A-1A, 1A-1B, 2A-1A, and 3A-1A.

In a very preferred embodiment said LC CDR1 consists of the peptide of any one of SEQ ID NOs 1, 4 and 6, said LC CDR2 consists of the peptide of SEQ ID NO:7, said LC CDR3 consists of the peptide of SEQ ID NO:8, said HC CDR1 consists of the peptide of SEQ ID NO:12, said HC CDR2 consists of the peptide of SEQ ID NO:13, and said HC CDR3 consists of the peptide of any one of SEQ ID NOs 15 and 16.

In a very preferred embodiment said LC CDR1 consists of the peptide of SEQ ID NO:1, said LC CDR2 consists of the peptide of SEQ ID NO:7, said LC CDR3 consists of the peptide of SEQ ID NO:8, said HC CDR1 consists of the peptide of SEQ ID NO:12, said HC CDR2 consists of the peptide of SEQ ID NO:13, and said HC CDR3 consists of the peptide of SEQ ID NO:15.

In a very preferred embodiment said LC CDR1 consists of the peptide of SEQ ID NO:1, said LC CDR2 consists of the peptide of SEQ ID NO:7, said LC CDR3 consists of the peptide of SEQ ID NO:8, said HC CDR1 consists of the peptide of SEQ ID NO:12, said HC CDR2 consists of the peptide of SEQ ID NO:13, and said HC CDR3 consists of the peptide of SEQ ID NO:16.

In a very preferred embodiment said LC CDR1 consists of the peptide of SEQ ID NO:4, said LC CDR2 consists of the peptide of SEQ ID NO:7, said LC CDR3 consists of the peptide of SEQ ID NO:8, said HC CDR1 consists of the peptide of SEQ ID NO:12, said HC CDR2 consists of the peptide of SEQ ID NO:13, and said HC CDR3 consists of the peptide of SEQ ID NO:15.

In a very preferred embodiment said LC CDR1 consists of the peptide of SEQ ID NO:6, said LC CDR2 consists of the peptide of SEQ ID NO:7, said LC CDR3 consists of the peptide of SEQ ID NO:8, said HC CDR1 consists of the peptide of SEQ ID NO:12, said HC CDR2 consists of the peptide of SEQ ID NO:13, and said HC CDR3 consists of the peptide of SEQ ID NO:15.

In a preferred embodiment said LCVR comprises a peptide, wherein said peptide consists of any one of the amino acid sequences depicted in FIG. 1; and said HCVR comprises a peptide, wherein said peptide consists of any one of the amino acid sequences depicted in FIG. 2.

In a very preferred embodiment LCVR comprises a peptide, wherein said peptide consists of any one of the amino acid sequences depicted in FIG. 1; and said HCVR comprises a peptide, wherein said peptide consists the amino acid sequence depicted in FIG. 2, wherein said amino acid sequence depicted in FIG. 2 has the same designator as the amino acid sequence depicted in FIG. 1. The designator is a character followed by three digits (e.g. D005).

In a preferred embodiment said antigen binding site comprises one LCVR and one HCVR, (a) wherein position 5 to 113 of said LCVR consists of the peptide of any one of SEQ ID NOs 20, 21 and 22, and (b) wherein position 7 to 121 of said HCVR consists of the peptide of SEQ ID NO:23, and wherein preferably position 1 to 4 of said LCVR consists of the peptide of SEQ ID NO:24, and/or wherein further preferably position 1 to 6 of said HCVR consists of the peptide of SEQ ID NO:25.

In a preferred embodiment said antigen binding site comprises one LCVR and one HCVR, (a) wherein position 5 to 113 of said LCVR consists of the peptide of SEQ ID NO:20, and (b) wherein position 7 to 121 of said HCVR consists of the peptide of SEQ ID NO:23, and wherein preferably position 1 to 4 of said LCVR consists of the peptide of SEQ ID NO:24, and/or wherein further preferably position 1 to 6 of said HCVR consists of the peptide of SEQ ID NO:25.

In a preferred embodiment said antigen binding site comprises one LCVR and one HCVR, (a) wherein position 5 to 113 of said LCVR consists of the peptide of SEQ ID NO:21, and (b) wherein position 7 to 121 of said HCVR consists of the peptide of SEQ ID NO:23, and wherein preferably position 1 to 4 of said LCVR consists of the peptide of SEQ ID NO:24, and/or wherein further preferably position 1 to 6 of said HCVR consists of the peptide of SEQ ID NO:25.

In a preferred embodiment said antigen binding site comprises one LCVR and one HCVR, (a) wherein position 5 to 113 of said LCVR consists of the peptide of SEQ ID NO:22, and (b) wherein position 7 to 121 of said HCVR consists of the peptide of SEQ ID NO:23, and wherein preferably position 1 to 4 of said LCVR consists of the peptide of SEQ ID NO:24, and/or wherein further preferably position 1 to 6 of said HCVR consists of the peptide of SEQ ID NO:25.

In a further preferred embodiment said antigen binding site comprises one LCVR and one HCVR, (a) wherein position 5 to 113 of said LCVR consists of a peptide, wherein said peptide is encoded by the nucleic acid sequence of any one of SEQ ID NOs 86, 87 and 88, and (b) wherein position 7 to 121 of said HCVR consists of a peptide, wherein said peptide is encoded by the nucleic acid sequence of SEQ ID NO:89, and wherein preferably position 1 to 4 of said LCVR consists of the peptide of SEQ ID NO:24, and/or wherein further preferably position 1 to 6 of said HCVR consists of the peptide of SEQ ID NO:25.

In a further preferred embodiment position 5 to 113 of said LCVR is at least 80%, preferably 85%, more preferably 90%, again more preferably 95%, even more preferably at least 96%, still more preferably 97%, again still more preferably 98%, again still more preferably 99% and most preferably 100% identical to the peptide of any one of SEQ ID NOs 20, 21, and 22, preferably to the peptide of SEQ ID NO:24; and position 7 to 121 of said HCVR is at least 80%, preferably 85%, more preferably 90%, again more preferably 95%, even more preferably at least 96%, still more preferably 97%, again still more preferably 98%, again still more preferably 99% and most preferably 100% identical to the peptide of SEQ ID NO:23.

In a further preferred embodiment said LCVR is at least 80%, preferably 85%, more preferably 90%, again more preferably 95%, even more preferably at least 96%, still more preferably 97%, again still more preferably 98%, again still more preferably 99% and most preferably 100% identical to any one of the amino acid sequences depicted in FIG. 1; and said HCVR is at least 80%, preferably 85%, more preferably 90%, again more preferably 95%, even more preferably at least 96%, still more preferably 97%, again still more preferably 98%, again still more preferably 99% and most preferably 100% identical to any one of the amino acid sequences depicted in FIG. 2.

In a further preferred embodiment said LCVR is at least 95%, preferably at least 96%, more preferably 97%, still more preferably 98%, still more preferably 99%, and most preferably 100% identical to any one of the amino acid sequences depicted in FIG. 1 ; and wherein said HCVR is at least 95%, preferably at least 96%, more preferably 97%, still more preferably 98%, still more preferably 99%, and most preferably 100% identical to any one of the amino acid sequences depicted in FIG. 2.

In a further preferred embodiment the differences in the amino acid sequences referred to above are located outside of the CDR positions of said LCVR and/or of said HCVR. Whether the amino acid sequence of a peptide or polypeptide has an amino acid sequence that is at least 80%, 85%, 90%, 95%, 97% or 99% identical to another, can be determined conventionally using known computer programs such the Bestfit program.

A monoclonal antibody of the invention can be recombinantly produced in any naturally occurring or synthetic format. The following embodiments thus explicitly refer to all aspects and embodiments of the invention. In one embodiment said monoclonal antibody is a recombinant antibody. In a preferred embodiment the monoclonal antibody of the invention is an antibody selected from the group consisting of: (a) single chain antibody, preferably scFv; (b) Fab fragment; (c) F(ab')2 fragment; (d) scFv-Fc fusion; (e) IgG1; (f) IgG2; (g) IgG3; (h) IgG4; (i) IgA; (j) IgE; (k) IgM; (l) IgD; and (m) diabody. In a preferred embodiment said monoclonal antibody comprises or preferably consists of exactly one LCVR and/or of exactly one HCVR.

In a further preferred embodiment said monoclonal antibody is a single chain antibody, wherein preferably said single chain antibody is an scFv. In a further preferred embodiment said single chain antibody comprises or preferably consists of a peptide, wherein said peptide is encoded by the nucleic acid sequence of any one of SEQ ID NOs 38 to 40. In a further preferred embodiment said single chain antibody is an Fc-fusion, preferably a Fcγ2c fusion, wherein further preferably said Fcγ2c fusion comprises or preferably consists of the a peptide, wherein said peptide is encoded by any one of SEQ ID NOs 42, 44, and 46. In a further preferred embodiment said single chain antibody comprises the peptide of any one of SEQ ID NOs 43, 45, and 47.

In a further preferred embodiment said monoclonal antibody is an IgG, preferably a human IgG. In a further preferred embodiment said monoclonal antibody is a IgG1, preferably a human IgG1. In a further preferred embodiment said monoclonal antibody comprises at least one, preferably exactly two, kappa LC(s), wherein preferably said kappa LC(s) comprise(s) or more preferably consist(s) of a peptide, wherein said peptide is at least 80%, preferably 85%, more preferably 90%, again more preferably 95%, even more preferably at least 96%, still more preferably 97%, again still more preferably 98%, again still more preferably 99% and most preferably 100% identical to any one of SEQ ID NOs 26 to 28. In a further preferred embodiment said monoclonal antibody is a human IgG1, wherein said human IgG1 comprises at least one, preferably exactly two, kappa LC(s), wherein said kappa LC(s) comprise(s) or preferably consist(s) of the peptide of any one of SEQ ID NOs 26 to 28.

In a further preferred embodiment said monoclonal antibody comprises at least one, preferably exactly two, gamma 1 HC(s), wherein preferably said gamma 1 HC(s) comprise(s) or more preferably consist(s) of a peptide, wherein said peptide is at least 80%, preferably 85%, more preferably 90%, again more preferably 95%, even more preferably at least 96%, still more preferably 97%, again still more preferably 98%, again still more preferably 99% and most preferably 100% identical to SEQ ID NO:29. In a further preferred embodiment said gamma 1 HC(s) comprise(s) or preferably consist(s) of the peptide of SEQ ID NO:29.

In a very preferred embodiment said monoclonal antibody is a human IgG1, wherein said human IgG1 comprises at least one, preferably exactly two, kappa LC(s), wherein said kappa LC(s) comprise(s) or more preferably consist(s) of a peptide of any one of SEQ ID NOs 26 to 28, and wherein said monoclonal antibody comprises at least one, preferably exactly two, gamma 1 HC(s), wherein said gamma 1 HC(s) comprise(s) or more preferably consist(s) of the of SEQ ID NO:29.

In a very preferred embodiment said monoclonal antibody is a human IgG1, wherein said human IgG1 comprises at least one, preferably exactly two, kappa LC(s), wherein said kappa LC(s) comprise(s) or more preferably consist(s) of the peptide of SEQ ID NO:26, and wherein said monoclonal antibody comprises at least one, preferably exactly two, gamma 1 HC(s), wherein said gamma 1 HC(s) comprise(s) or more preferably consist(s) of the of SEQ ID NO:29.

In a very preferred embodiment said monoclonal antibody is a human IgG1, wherein said human IgG1 comprises at least one, preferably exactly two, kappa LC(s), wherein said kappa LC(s) comprise(s) or more preferably consist(s) of the peptide of SEQ ID NO:27, and wherein said monoclonal antibody comprises at least one, preferably exactly two, gamma 1 HC(s), wherein said gamma 1 HC(s) comprise(s) or more preferably consist(s) of the of SEQ ID NO:29.

In a very preferred embodiment said monoclonal antibody is a human IgG1, wherein said human IgG1 comprises at least one, preferably exactly two, kappa LC(s), wherein said kappa LC(s) comprise(s) or more preferably consist(s) of the peptide of SEQ ID NO:28, and wherein said monoclonal antibody comprises at least one, preferably exactly two, gamma 1 HC(s), wherein said gamma 1 HC(s) comprise(s) or more preferably consist(s) of the of SEQ ID NO:29.

Preferably, the monoclonal antibody of the invention is an IgG1, preferably a human IgG1, most preferably a fully human IgG1. Thus, in a preferred embodiment said monoclonal antibody comprises two, preferably exactly two, of said gamma 1 HCs, wherein further preferably said two, preferably said exactly two of said gamma 1 HCs are identical.

In a further preferred embodiment said monoclonal antibody comprises two, preferably exactly two LCs, wherein preferably said LCs are selected from (a) lambda LC; and (b) kappa LC, most preferably kappa LC; wherein still further preferably said two, preferably said exactly two of said LCs are identical.

In a preferred embodiment said monoclonal antibody, preferably said isolated monoclonal antibody, is specifically binding influenza M2e antigen, wherein said influenza M2e antigen comprises or consists of at least one epitope of the extracellular domain of the influenza A M2 protein. In a further preferred embodiment said influenza M2e antigen comprises or consists of the extracellular domain of the influenza A M2 protein, preferably of amino acids 2 to 24 of the influenza A M2 protein. In a further preferred embodiment, said influenza M2e antigen comprises or preferably consists of the peptide of any one of SEQ ID NOs 48 to 83 and 90 to 92, wherein preferably said influenza M2e antigen comprises or preferably consists of the peptide of any one of SEQ ID NOs 48 to 50, and wherein most preferably said influenza M2e antigen comprises or preferably consists of the peptide of SEQ ID NO:48.

In a further preferred embodiment, said influenza M2e antigen comprises or consists of at least one epitope of SEQ ID NO:48, preferably said influenza M2e antigen comprises or consists of an epitope comprised by the amino acid sequence of SEQ ID NO:93.

In a further preferred embodiment said monoclonal antibody is specifically binding influenza M2e antigen, wherein the EC50 value and/or the dissociation constant (Kd) of said monoclonal antibody and said influenza M2e antigen is at most 1000 nM ($<=10^{-6}$ M), preferably at most 100 nM ($<=10^{-7}$ M), more preferably at most 10 nM ($<=10^{-8}$ M), still more preferably at most 1 nM ($<=10^{-9}$ M), still more preferably at most 100 pM (<=$10^{-10}$ M), still more preferably at most 10 pM (<=$10^{-11}$ M), and most preferably at most 1 pM (<=$10^{-12}$ M), wherein preferably said influenza M2e antigen is the extracellular domain of influenza A M2 protein, wherein preferably said influenza M2e antigen is the peptide of any one of SEQ ID NOs 48 to 83, more preferably of any one of SEQ ID NOs 48 to 50, and most preferably of SEQ ID NO:48, and wherein still further preferably said Kd is determined by Friguet-ELISA, most preferably under conditions essentially as described in Example 11, and/or wherein said EC50 value is determined by ELISA, preferably under conditions essentially as described in the first paragraph of Example 4 herein.

In a further preferred embodiment said monoclonal antibody is specifically binding influenza M2e antigen, wherein the dissociation constant (Kd) of said monoclonal antibody and said influenza M2e antigen is at most 100 nM, preferably at most 10 nM, more preferably at most 6 nM and most preferably at most 5 nM, wherein preferably said influenza M2e antigen is SEQ ID NO:48, most preferably in solution, and wherein still further preferably said Kd is determined by Friguet-ELISA, most preferably under conditions essentially as described in Example 11.

In a further preferred embodiment said monoclonal antibody is specifically binding influenza M2e antigen, the dissociation constant (Kd) of said monoclonal antibody and said influenza M2e antigen is 1 to 100 nM, preferably 1 to 10 nM, more preferably 1 to 6 nM, still more preferably 3 to 6 nM, and most preferably 4 to 5 nM, wherein further preferably said influenza M2e antigen is SEQ ID NO:48, most preferably in solution, and wherein still further preferably said Kd is determined by Friguet-ELISA, most preferably under conditions essentially as described in Example 11.

In a further preferred embodiment said monoclonal antibody is specifically binding influenza M2e antigen, wherein the dissociation constant (Kd) of said monoclonal antibody and said influenza M2e antigen is 0.01 pM to 1000 nM, preferably 0.1 pM to 100 nM, more preferably 0.1 pM to 10 nM, still more preferably 0.1 pM to 1 nM, still more preferably 0.1 pM to 100 pM, still more preferably 0.1 pM to 50 pM, still more preferably 0.1 pM to 20 pM, still more preferably 0.1 pM to 15 pM, still more preferably 1 pM to 15 pM, and most preferably 1 pM to 10 pM, wherein preferably said influenza M2e antigen is an RNAse conjugate of the extracellular domain of influenza A M2 protein, most preferably in solution, wherein further preferably said influenza M2e antigen comprises the peptide of any one of SEQ ID NOs 48 to 83 and 90 to 92, more preferably of any one of SEQ ID NOs 48 to 50, and most preferably of SEQ ID NO:48, and wherein still further preferably said Kd is determined by Friguet-ELISA, most preferably under conditions essentially as described in Example 11.

In a further preferred embodiment the said monoclonal antibody is specifically binding influenza M2e antigen, wherein said influenza M2e antigen is a cell comprising at least one epitope of the extracellular domain of influenza A M2 protein on its cell surface.

In a further preferred embodiment the said monoclonal antibody is specifically binding influenza M2e antigen, wherein said influenza M2e antigen is a cell comprising the extracellular domain of influenza A M2 protein on its cell surface.

In a further preferred embodiment said monoclonal antibody is specifically binding influenza M2e antigen, wherein the dissociation constant (Kd) of said monoclonal antibody and said influenza M2e antigen is 1 to 100 nM, preferably 1 to 10 nM, more preferably 1 to 6 nM, still more preferably 3 to 6 nM, and most preferably 4 to 5 nM, and wherein preferably said influenza M2e antigen is SEQ ID NO:48, most preferably in solution, and wherein still further preferably said Kd is determined by Friguet-ELISA, most preferably under conditions essentially as described in Example 11, and wherein further preferably said LC CDR1 consists of the peptide of any one of SEQ ID NOs 1, 4 and 6, said LC CDR2 consists of the peptide of SEQ ID NO:7, said LC CDR3 consists of the peptide of SEQ ID NO:8, said HC CDR1 consists of the peptide of SEQ ID NO:12, said HC CDR2 consists of the peptide of SEQ ID NO:13, and said HC CDR3 consists of the peptide of SEQ ID NO:15.

In a further preferred embodiment said monoclonal antibody is specifically binding influenza M2e antigen, wherein the dissociation constant (Kd) of said monoclonal antibody and said influenza M2e antigen is 1 to 100 nM, preferably 1 to 10 nM, more preferably 1 to 6 nM, still more preferably 3 to 6 nM, and most preferably 4 to 5 nM, and wherein preferably said influenza M2e antigen is SEQ ID NO:48, most preferably in solution, and wherein still further preferably said Kd is determined by Friguet-ELISA, most preferably under conditions essentially as described in Example 11, and wherein further preferably said LC CDR1 consists of the peptide of SEQ ID NO:1, said LC CDR2 consists of the peptide of SEQ ID NO:7, said LC CDR3 consists of the peptide of SEQ ID NO:8, said HC CDR1 consists of the peptide of SEQ ID NO:12, said HC CDR2 consists of the peptide of SEQ ID NO:13, and said HC CDR3 consists of the peptide of SEQ ID NO:15.

In a further preferred embodiment said monoclonal antibody is specifically binding influenza M2e antigen, wherein the dissociation constant (Kd) of said monoclonal antibody and said influenza M2e antigen is 1 to 100 nM, preferably 1 to 10 nM, more preferably 1 to 6 nM, still more preferably 3 to 6 nM, and most preferably 4 to 5 nM, and wherein preferably said influenza M2e antigen is SEQ ID NO:48, most preferably in solution, and wherein still further preferably said Kd is determined by Friguet-ELISA, most preferably under conditions essentially as described in Example 11, and wherein position 5 to 113 of said LCVR consists of the peptide of any one of SEQ ID NOs 20, 21 and 22.

In a further preferred embodiment said monoclonal antibody is specifically binding influenza M2e antigen, wherein the dissociation constant (Kd) of said monoclonal antibody and said influenza M2e antigen is 1 to 100 nM, preferably 1 to 10 nM, more preferably 1 to 6 nM, still more preferably 3 to 6 nM, and most preferably 4 to 5 nM and wherein preferably said influenza M2e antigen is SEQ ID NO:48, most preferably in solution, and wherein still further preferably said Kd is determined by Friguet-ELISA, most preferably under conditions essentially as described in Example 11, and wherein position 7 to 121 of said HCVR consists of the peptide of SEQ ID NO:23.

In a further preferred embodiment said monoclonal antibody is specifically binding influenza M2e antigen, wherein the dissociation constant (Kd) of said monoclonal antibody and said influenza M2e antigen is 1 to 100 nM, preferably 1 to 10 nM, more preferably 1 to 6 nM, still more preferably 3 to 6 nM, and most preferably 4 to 5 nM, and wherein preferably said influenza M2e antigen is SEQ ID NO:48, most preferably in solution, and wherein still further preferably said Kd is determined by Friguet-ELISA, most preferably under conditions essentially as described in Example 11, and wherein position 5 to 113 of said LCVR consists of the peptide of any one of SEQ ID NOs 20, 21 and 22, and wherein position 7 to 121 of said HCVR consists of the peptide of SEQ ID NO:23.

In a further preferred embodiment said monoclonal antibody is specifically binding influenza M2e antigen, wherein the dissociation constant (Kd) of said monoclonal antibody and said influenza M2e antigen is 1 to 100 nM, preferably 1 to 10 nM, more preferably 1 to 6 nM, still more preferably 3 to 6 nM, and most preferably 4 to 5, and wherein preferably said influenza M2e antigen is SEQ ID NO:48, most preferably in solution, and wherein still further preferably said Kd is determined by Friguet-ELISA, most preferably under conditions essentially as described in Example 11, and wherein position 5 to 113 of said LCVR consists of the peptide of SEQ ID NO:20, and wherein position 7 to 121 of said HCVR consists of the peptide of SEQ ID NO:23.

In a further preferred embodiment said monoclonal antibody is specifically binding influenza M2e antigen, wherein the dissociation constant (Kd) of said monoclonal antibody and said influenza M2e antigen is 1 to 100 nM, preferably 1 to 10 nM, more preferably 1 to 6 nM, still more preferably 3 to 6 nM, and most preferably 4 to 5, and wherein preferably said influenza M2e antigen is SEQ ID NO:48, most preferably in solution, and wherein still further preferably said Kd is determined by Friguet-ELISA, most preferably under conditions essentially as described in Example 11, and wherein said monoclonal antibody is a human IgG, preferably a human IgG1, wherein preferably said human IgG1 comprises at least one, preferably exactly two, kappa LC(s), wherein said kappa LC(s) comprise(s) or more preferably consist(s) of a peptide of any one of SEQ ID NOs 26 to 28, preferably SEQ ID NO:20, and wherein said monoclonal antibody comprises at least one, preferably exactly two, gamma 1 HC(s), wherein said gamma 1 HC(s) comprise(s) or more preferably consist(s) of the of SEQ ID NO:29.

An epitope mapping revealed that the minimal epitope which is recognized by an antibody of the invention is comprised in the amino acid sequence LLTEVETP (SEQ ID NO:93) of the M2e consensus sequence (SEQ ID NO:48). It has been shown that an antibody of the invention is capable of recognizing variants of this epitope occurring in M2e of other influenza A genotypes (see FIG. 8A).

In a further preferred embodiment said at least one antigen binding site recognizes an epitope comprised by the amino acid sequence LLTEVETP (SEQ ID NO:93), and wherein further preferably said LC CDR1 consists of the peptide of SEQ ID NO:1, said LC CDR2 consists of the peptide of SEQ ID NO:7, said LC CDR3 consists of the peptide of SEQ ID NO:8, said HC CDR1 consists of the peptide of SEQ ID NO:12, said HC CDR2 consists of the peptide of SEQ ID NO:13, and said HC CDR3 consists of the peptide of SEQ ID NO:15.

In a further preferred embodiment said at least one antigen binding site recognizes an epitope comprised by the amino acid sequence LLTEVETP (SEQ ID NO:93), and wherein position 5 to 113 of said LCVR consists of the peptide of SEQ ID NO:20, and wherein position 7 to 121 of said HCVR consists of the peptide of SEQ ID NO:23.

In a further preferred embodiment said at least one antigen binding site recognizes an epitope comprised by the amino acid sequence LLTEVETP (SEQ ID NO:93), and wherein said monoclonal antibody is a human IgG, preferably a human IgG1, wherein preferably said human IgG1 comprises at least one, preferably exactly two, kappa LC(s), wherein said kappa LC(s) comprise(s) or more preferably consist(s) of the peptide of SEQ ID NO:26, and wherein said monoclonal antibody comprises at least one, preferably exactly two, gamma 1 HC(s), wherein said gamma 1 HC(s) comprise(s) or more preferably consist(s) of the of SEQ ID NO:29.

In a further preferred embodiment said at least one antigen binding site recognizes an epitope comprised by the amino acid sequence LLTEVETP (SEQ ID NO:93), and wherein further preferably said LC CDR1 consists of the peptide of SEQ ID NO:4, said LC CDR2 consists of the peptide of SEQ ID NO:7, said LC CDR3 consists of the peptide of SEQ ID NO:8, said HC CDR1 consists of the peptide of SEQ ID NO:12, said HC CDR2 consists of the peptide of SEQ ID NO:13, and said HC CDR3 consists of the peptide of SEQ ID NO:15.

In a further preferred embodiment said at least one antigen binding site recognizes an epitope comprised by the amino acid sequence LLTEVETP (SEQ ID NO:93), and wherein position 5 to 113 of said LCVR consists of the peptide of SEQ ID NO:21, and wherein position 7 to 121 of said HCVR consists of the peptide of SEQ ID NO:23.

In a further preferred embodiment said at least one antigen binding site recognizes an epitope comprised by the amino acid sequence LLTEVETP (SEQ ID NO:93), and wherein said monoclonal antibody is a human IgG, preferably a human IgG1, wherein preferably said human IgG1 comprises at least one, preferably exactly two, kappa LC(s), wherein said kappa LC(s) comprise(s) or more preferably consist(s) of the peptide of SEQ ID NO:27, and wherein said monoclonal antibody comprises at least one, preferably exactly two, gamma 1 HC(s), wherein said gamma 1 HC(s) comprise(s) or more preferably consist(s) of the of SEQ ID NO:29.

In a further preferred embodiment said at least one antigen binding site recognizes an epitope comprised by the amino acid sequence LLTEVETP (SEQ ID NO:93), and wherein further preferably said LC CDR1 consists of the peptide of SEQ ID NO:6, said LC CDR2 consists of the peptide of SEQ ID NO:7, said LC CDR3 consists of the peptide of SEQ ID NO:8, said HC CDR1 consists of the peptide of SEQ ID NO:12, said HC CDR2 consists of the peptide of SEQ ID NO:13, and said HC CDR3 consists of the peptide of SEQ ID NO:15.

In a further preferred embodiment said at least one antigen binding site recognizes an epitope comprised by the amino acid sequence LLTEVETP (SEQ ID NO:93), and wherein position 5 to 113 of said LCVR consists of the peptide of SEQ ID NO:22, and wherein position 7 to 121 of said HCVR consists of the peptide of SEQ ID NO:23.

In a further preferred embodiment said at least one antigen binding site recognizes an epitope comprised by the amino acid sequence LLTEVETP (SEQ ID NO:93), and wherein said monoclonal antibody is a human IgG, preferably a human IgG1, wherein preferably said human IgG1 comprises at least one, preferably exactly two, kappa LC(s), wherein said kappa LC(s) comprise(s) or more preferably consist(s) of the peptide of SEQ ID NO:28, and wherein said monoclonal antibody comprises at least one, preferably exactly two, gamma 1 HC(s), wherein said gamma 1 HC(s) comprise(s) or more preferably consist(s) of the of SEQ ID NO:29.

It is to be understood that it is well within the skill of the artisan to use a HCVR of a first antibody specifically binding influenza M2e antigen, to select a corresponding LCVR from a suitable source, and to create a second antibody, wherein said second antibody comprises said HCVR of said first antibody and the selected LCVR, and wherein said second antibody is capable of binding influenza A Me2 antigen with about the same specificity as said first antibody ("chain shuffling"). It is furthermore apparent for the artisan that in an analogous manner the LCVR of a first antibody can be used to select a corresponding HCVR from a suitable source. Suitable sources for the amplification of LCVRs and/or HCVRs are, for example, cDNA from naive human B cells, cDNA from B cells of a human subject immunized with an influenza M2e antigen, and fully synthetic libraries, such as Morphosys' HuCAL library. These methods are described in detail in Kang A S et al. (Proc Natl Acad Sci USA 88, 11120-11123, 1991), Marks J D et al. (Biotechnology (N Y) 10, 779-783, 1992), and Jespers et al. (Biotechnology (N Y) 12, 899-903, 1994).

Thus, a further aspect of the invention is a LCVR of a monoclonal antibody, wherein said monoclonal antibody is a human monoclonal antibody, most preferably a fully human monoclonal antibody, and wherein said monoclonal antibody is specifically binding influenza M2e antigen, and wherein said LCVR comprises: (a) one LC CDR1, wherein said LC CDR1 consists of the peptide of any one of SEQ ID NOs 1, 2, 3, 4, 5, and 6; (b) one LC CDR2, wherein said LC CDR2 consists of the peptide of SEQ ID NO:7; (c) one LC CDR3, wherein said LC CDR3 consists of the peptide of any one of SEQ ID NOs 8, 9, 10, and 11.

In a preferred embodiment said LCVR is selected from: (a) a LCVR, wherein (i) said LC CDR1 consists of the peptide of SEQ ID NO:1, (ii) said LC CDR2 consists of the peptide of SEQ ID NO:7, and (iii) said LC CDR3 consists of the peptide of SEQ ID NO:8; (b) a LCVR, wherein (i) said LC CDR1 consists of the peptide of SEQ ID NO:2, (ii) said LC CDR2 consists of the peptide of SEQ ID NO:7, and (iii) said LC CDR3 consists of the peptide of SEQ ID NO:8; (c) a LCVR, wherein (i) said LC CDR1 consists of the peptide of SEQ ID NO:3, (ii) said LC CDR2 consists of the peptide of SEQ ID NO:7, and (iii) said LC CDR3 consists of the peptide of SEQ ID NO:8; (d) a LCVR, wherein (i) said LC CDR1 consists of the peptide of SEQ ID NO:1, (ii) said LC CDR2 consists of the peptide of SEQ ID NO:7, and (iii) said LC CDR3 consists of the peptide of SEQ ID NO:9; (e) a LCVR, wherein (i) said LC CDR1 consists of the peptide of SEQ ID NO:1, (ii) said LC CDR2 consists of the peptide of SEQ ID NO:7, and (iii) said LC CDR3 consists of the peptide of SEQ ID NO:10; (f) a LCVR, wherein (i) said LC CDR1 consists of the peptide of SEQ ID NO:4, (ii) said LC CDR2 consists of the peptide of SEQ ID NO:7, and (iii) said LC CDR3 consists of the peptide of SEQ ID NO:8; (g) a LCVR, wherein (i) said LC CDR1 consists of the peptide of SEQ ID NO:5, (ii) said LC CDR2 consists of the peptide of SEQ ID NO:7, and (iii) said LC CDR3 consists of the peptide of SEQ ID NO:8; (h) a LCVR, wherein (i) said LC CDR1 consists of the peptide of SEQ ID NO:6, (ii) said LC CDR2 consists of the peptide of SEQ ID NO:7, and (iii) said LC CDR3 consists of the peptide of SEQ ID NO:8; and (i) a LCVR, wherein (i) said LC CDR1 consists of the peptide of SEQ ID NO:1, (ii) said LC CDR2 consists of the peptide of SEQ ID NO:7, and (iii) said LC CDR3 consists of the peptide of SEQ ID NO:11.

In a very preferred embodiment position 5 to 113 of said LCVR consists of the peptide of any one of SEQ ID NOs 20, 21 and 22, most preferably SEQ ID NO:20, wherein preferably position 1 to 4 of said LCVR consists of the peptide of SEQ ID NO:24.

A further aspect of the invention is a HCVR of a monoclonal antibody, wherein said monoclonal antibody is a human monoclonal antibody, preferably a fully human monoclonal antibody, and wherein said monoclonal antibody is specifically binding influenza M2e antigen, and wherein said HCVR comprises: one HC CDR1, wherein said HC CDR1 consists of the peptide of SEQ ID NO:12; (b) one HC CDR2, wherein said HC CDR2 consists of the peptide of any one of SEQ ID NOs 13 and 14; and (c) one HC CDR3, wherein said HC CDR3 consists of the peptide of any one of SEQ ID NOs 15, 16, 17, 18, and 19.

In a further preferred embodiment, said HCVR comprises: one HC CDR1, wherein said HC CDR1 consists of the peptide of SEQ ID NO:12; (b) one HC CDR2, wherein said HC CDR2 consists of the peptide of any one of SEQ ID NO:13; and (c) one HC CDR3, wherein said HC CDR3 consists of the peptide of SEQ ID NO:15. In a preferred embodiment position 7 to 121 of said HCVR consists of the peptide of SEQ ID NO:23, wherein preferably position 1 to 6 of said HCVR consists of the peptide of SEQ ID NO:25.

All aspects of the invention, and hereby in particular the pharmaceutical compositions, methods and uses, which are disclosed in the following, relate to any one of the monoclonal antibodies disclosed herein. However, embodiments which relate to the antibody clones D005, E040 and F052 are preferred, and hereby in particular clone D005. Especially preferred are therefore embodiments, wherein said monoclonal antibody comprises at least one antigen binding site, wherein said antigen binding site comprises: (a) one LCVR, wherein said LCVR comprises: (i) one LC CDR1, wherein said LC CDR1 consists of the peptide of any one of SEQ ID NOs 1, 4, and 6, preferably SEQ ID NO:1; (ii) one LC CDR2, wherein said LC CDR2 consists of the peptide of SEQ ID NO:7; and (iii) one LC CDR3, wherein said LC CDR3 consists of the peptide of SEQ ID NO:8; and (b) one HCVR, wherein said HCVR comprises: (i) one HC CDR1, wherein said HC CDR1 consists of the peptide of SEQ ID NO:12; (ii) one HC CDR2, wherein said HC CDR2 consists of the peptide of SEQ ID NO:13; and (iii) one HC CDR3, wherein said HC CDR3 consists of the peptide of SEQ ID NO:15. Still more preferred are embodiments, wherein position 5 to 113 of said LCVR consists of the peptide of any one of SEQ ID NOs 20, 21 and 22, preferably of SEQ ID NO:20, and wherein position 7 to 121 of said HCVR consists of the peptide of SEQ ID NO:23. Still more preferred are embodiments, wherein said monoclonal antibody is an IgG1, and wherein said monoclonal antibody comprises at least one light chain, and wherein said monoclonal antibody further comprises at least one heavy chain, wherein said light chain comprises or preferably consists of the amino acid sequence of any one of SEQ ID NOs 26, 27, and 28, preferably of SEQ ID NO:26, and wherein said heavy chain comprises or preferably consists of the amino acid of SEQ ID NO:29.

In a further aspect, the invention relates a nucleic acid molecule encoding a HCVR or a LCVR of the invention, a monoclonal antibody of the invention or an individual chain thereof. In a preferred embodiment said nucleic acid molecule is encoding a peptide selected from (a) a LCVR of the invention, wherein preferably said LCVR comprises or preferably consists of any one of the peptides depicted in FIG. 1; (b) a LCVR, wherein said LCVR comprises or preferably consists of the peptide of any one of SEQ ID NOs 20, 21, and 22; (c) a HCVR of the invention, wherein preferably said HCVR comprises or preferably consists of any one of the peptides depicted in FIG. 2; (d) a HCVR, wherein said HCVR comprises or preferably consists of the peptide of SEQ ID NO:23; (e) a single chain antibody of the invention, wherein preferably said single chain antibody comprises or preferably consists of the peptide of any one of SEQ ID NOs 43, 45 and 47; (f) a kappa LC of the invention, wherein preferably said kappa LC comprises or preferably consists of the peptide of any one of SEQ ID NOs 26, 27, and 28; (g) a gamma 1 HC of the invention, wherein preferably said gamma 1 HC comprises or preferably consists of the peptide of SEQ ID NO:29; and (h) a monoclonal antibody of the invention.

In a further preferred embodiment said nucleic acid molecule comprises or preferably consists of the nucleotide sequence of any one of SEQ ID NOs 86 to 89. In a further preferred embodiment said nucleic acid molecule comprises the nucleotide sequence of any one of SEQ ID NOs 86 to 88, and wherein said nucleic acid molecule further comprises the nucleotide sequence of SEQ ID NO:89.

In a further preferred embodiment said nucleic acid molecule comprises or preferably consists of the nucleotide sequence of any one of SEQ ID NOs 30, 32, 34, and 36. In a further preferred embodiment said nucleic acid molecule comprises the nucleotide sequence of any one of SEQ ID NOs 32, 34, and 36, and wherein said nucleic acid molecule further comprises the nucleotide sequence of SEQ ID NO:30.

In a further preferred embodiment said nucleic acid molecule comprises or preferably consists of the nucleotide sequence of any one of SEQ ID NOs 38, 39, and 40.

In a further preferred embodiment said nucleic acid molecule comprises or preferably consists of the nucleotide sequence of SEQ ID NO:41.

In a further preferred embodiment said nucleic acid molecule comprises or preferably consists of the nucleotide sequence of any one of SEQ ID NOs 42, 44, and 46. In a further preferred embodiment said nucleic acid molecule comprises or preferably consists of the nucleotide sequence of any one of SEQ ID NOs 42, 44, and 46.

In a further aspect, the invention relates to an expression vector for the recombinant expression of an antibody of the invention. In a preferred embodiment, said expression vector comprises at least one nucleic acid molecule of the invention. Expression vectors suitable for the expression of the monoclonal antibodies of the invention are disclosed, for example, in WO2008/055795A1. In a preferred embodiment said expression vector comprises the nucleotide sequence of any one of SEQ ID NOs 86 to 89. In a further preferred embodiment said expression vector comprises the nucleotide sequence of any one of SEQ ID NOs 86 to 88, wherein preferably said expression vector further comprises the nucleotide sequence of SEQ ID NO:89. In a further preferred embodiment said expression vector comprises the nucleotide sequence of SEQ ID NO:41.

In a further aspect, the invention relates to a host cell comprising at least one nucleic acid molecule or at least one expression vector of the invention, wherein preferably said host cell is a bacteria cell or an eukaryotic cell. In a preferred embodiment said host cell is a eukaryotic cell selected from (a) yeast cell, (b) insect cell; and (c) mammalian cell, wherein preferably said mammalian cell is selected from HEK-293T cell, CHO cell, and COS cell. Very preferably, said mammalian cells is a HEK-293T cell.

In a further aspect, the invention relates to the monoclonal antibody of the invention for use as a pharmaceutical.

The monoclonal antibody of the invention can be incorporated into compositions suitable for administration to a subject. Thus, in a further aspect, the invention relates to a pharmaceutical composition comprising at least one monoclonal antibody of the invention, wherein preferably said pharmaceutical composition further comprises a pharmaceutically acceptable carrier, diluent or excipient. Pharmaceutically acceptable carriers, diluents and excipients are disclosed, for example, in Remington, The Science and Practice of Pharmacy, 19$^{th}$ edition, Gennaro (ed.), Mack publishing Co., Easton, Pa., 1995. Pharmaceutical compositions of the invention are administered in a single dose or in multiple doses.

In a preferred embodiment said pharmaceutical composition further comprises at least one further antibody, wherein preferably said at least one further antibody is specifically binding an influenza antigen, preferably an influenza M2e antigen.

In a further preferred embodiment said pharmaceutical composition further comprises at least one further antibody, wherein preferably said at least one further antibody is specifically binding an influenza antigen, wherein said influenza antigen is an antigen of influenza A virus HA protein or an antigen of influenza A virus NA protein.

The monoclonal antibodies of the invention may be used in passive immunization, preferably of humans, and further preferably against influenza A virus. The monoclonal antibodies of the invention are therefore useful in the treatment and/or prophylaxis of influenza A infection. In a further aspect, the invention relates to a method of passive immunization, preferably against influenza A virus, said method comprising administering to a subject an effective amount of the monoclonal antibody of the invention or an effective amount of the pharmaceutical composition of the invention.

The monoclonal antibody and/or the pharmaceutical composition of the invention are preferably administered to a subject, preferably to a human, using standard administration techniques, preferably selected from oral administration, intravenous administration, intraperitoneal administration, subcutaneous administration, pulmonary administration, transdermal administration, intramuscular administration, intranasal administration, buccal administration, sublingual administration, and suppository administration.

In a further aspect, the invention relates to a method of treating influenza A virus infection, said method comprising administering to a subject an effective amount of the monoclonal antibody of the invention or an effective amount of the pharmaceutical composition of the invention, wherein preferably said subject is a human, and wherein further preferably said subject suffers from influenza A virus infection.

In a further aspect, the invention relates to a method of preventing influenza A virus infection, said method comprising administering to a subject an effective amount of the monoclonal antibody of the invention or an effective amount of the pharmaceutical composition of the invention, wherein preferably said subject is a human, and wherein further preferably said subject is not infected with influenza A virus.

In a further aspect, the invention relates to the monoclonal antibody of the invention or to the pharmaceutical composition of the invention, for use in passive immunization, preferably against influenza A virus, preferably in a human, wherein further preferably said monoclonal antibody is to be administered to said human.

In a further aspect, the invention relates to the monoclonal antibody of the invention or to the pharmaceutical composition of the invention, for use in a method of treatment and/or prophylaxis of influenza A virus infection, preferably in a human.

In a further aspect, the invention relates to the use of the monoclonal antibody of the invention in the manufacture of a medicament for passive immunization, preferably against influenza A virus.

In a further aspect, the invention relates to a monoclonal antibody of the invention for use in passive immunization, preferably against influenza A virus.

In a further aspect, the invention relates to the use of the monoclonal antibody of the invention in the manufacture of a medicament for the treatment and/or prophylaxis of influenza A virus infection, preferably in a human.

In a further aspect, the invention relates to a monoclonal antibody of the invention for use in a method of treating or preventing influenza A virus infection, preferably in a human.

A further aspect of the invention is the use of an antibody of the invention in a method of quantitative and/or qualitative detection of influenza A virus M2 protein, preferably in a blood sample and most preferably by ELISA.

It is to be understood that the all aspects of the invention relate to any monoclonal antibody which is disclosed herein.

EXAMPLE 1

Identification of M2-Specific Single-Chain Antibodies by Mammalian Cell Display

Peripheral blood mononuclear cells (PBMC) were isolated from 10 ml of heparinized blood of an individual with high M2-titers using the BD Vacutainer™ CPT™ Tube method (BD Biosciences, Franklin Lakes, N.J.). PBMC were pre-incubated with Alexa 647 nm-labeled Qβ (5.5 µg/ml) and human gamma globulin (11 µg/mL; Jackson ImmunoResearch) and then stained with: (1) an M2 extracellular domain consensus peptide (M2e; SEQ ID NO:48, cf. Table 7) coupled to Qβ (2.4 µg/ml) in combination with a Alexa 488 nm-labeled Qβ -specific mouse mAb (2 µg/ml), as well as a M2-specific mouse mAb (0.5 µg/ml) in combination with FITC-labeled donkey anti-mouse IgG antibody (1 µg/ml; Jackson ImmunoResearch); (2) PE-labeled mouse anti-human IgM (diluted 1:50; BD Biosciences/Pharmingen), mouse anti-human IgD (diluted 1:100; BD Biosciences/Pharmingen), mouse anti-human CD14 (diluted 1:50; BD Biosciences/Pharmingen), and mouse anti-human CD3 (diluted 1:50; BD Biosciences/Pharmingen) antibodies; and (3) PE-TexasRed-labeled mouse anti-human CD19 antibody (diluted 1:50; Caltag Laboratories). After staining, cells were washed and filtered, and 334 M2e-specific B cells (FL1-positive, FL2-negative, FL3-positive, FL4-negative) were sorted on a FACSVantage® SE flow cytometer (Becton Dickinson).

Antigen-specific B cells were used for the construction of a Sindbis-based scFv cell surface display library essentially as described (see WO 1999/025876 A1 for Sindbis-based screening in general and WO 2008/055795 A1 for its application in antibody screening, the entirety of which is incorporated herein by reference). Cells displaying M2e-specific scFv antibodies were isolated using M2e coupled to RNase A (5 µg/ml) in combination with an RNase-specific rabbit polyclonal antibody (2.5 µg/ml; Abcam) and a FITC-labeled donkey anti-rabbit IgG antibody (1.5 µg/ml; Jackson ImmunoResearch) or using Qβ-M2e (1 µg/ml) in combination with a M2-specific mouse mAb (0.5 µg/ml) and FITC-labeled donkey anti-mouse IgG antibody (1 µg/ml; Jackson ImmunoResearch). Each cell was sorted into a well of a 24-well plate containing 50% confluent BHK feeder cells. Upon virus spread (2 days post sorting), the infected cells were tested by FACS analysis for M2e-binding to identify virus clones encoding M2e-specific scFv antibodies.

EXAMPLE 2

Gene Rescue, ELISA Screening and Sequencing of M2-Specific Antibodies

The supernatants of BHK cells encoding putative M2e-specific antibodies, each containing a monoclonal recombinant Sindbis virus, were subjected to RT-PCR as described (see WO 2008/055795 A1). The resulting PCR products, each comprising a scFv coding region, were digested with the restriction endonuclease SfiI and cloned into the expression vector pCEP-SP-Sfi-Fc (disclosed as SEQ ID NO:37 in WO 2008/055795 A1), allowing for expression of scFv proteins fused to a C-terminal human Fc-γ1 domain under the control of a CMV promoter.

For ELISA analysis, each of the clones was transfected into HEK-293T cells in a 24-well plate format, using Lipofectamine 2000 (Invitrogen) according to the manufacturer's recommendations. 2-3 days post transfection, supernatants containing transiently expressed scFv-Fc fusion proteins were harvested. To check for M2e-specific binding, ELISA plates were coated with M2e-conjugated RNAse A at a concentration of 4 µg/ml in phosphate-buffered saline (PBS) over night at 4° C. In parallel, scFv-Fc expression levels were monitored in by sandwich ELISA. For this, an identical set of plates was coated with Fcγ-specific, goat anti-human F(ab')2 antibody (Jackson ImmunoResearch Laboratories 109-006-098) at a concentration of 2.5 µg/ml. The plates were then washed with wash buffer (PBS/0.05% Tween) and blocked for 2 h at room temperature with 3% BSA in wash buffer. The plates were then washed again and incubated with 3-fold serial dilutions of the cell culture supernatants, starting at a dilution of 1/10. All dilutions were done in wash buffer. Plates were incubated at room temperature for 2 h and then extensively washed with wash buffer. Bound scFv-Fc fusion proteins were then detected by a 1 h incubation with a HRPO-labeled, Fcγ-specific, goat anti-human IgG antibody (Jackson ImmunoResearch Laboratories 109-035-098). After extensive washing with wash buffer, plates were developed with OPD solution (1 OPD tablet, 25 ml OPD buffer and 8 µl 30% $H_2O_2$) for 5 to 10 min and the reaction was stopped with 5% $H_2SO_4$ solution. Plates were then read at OD 450 nm on an ELISA reader (Biorad Benchmark).

In total, 53 ELISA-positive clones encoding M2e-specific scFv antibodies, each binding with an EC50 in the range of 2 to 10 ng/ml (approximately 18 to 90 pM), were sequenced as described (see WO 2008/055795 A1). All antibody sequences were very similar and obviously clonally related, with heavy chain variable regions comprising VH3 family sequences and light chain variable regions comprising VK4 family sequences. The amino acid sequences of the light chains of all 53 clones are depicted in FIG. 1. The amino acid sequences of the heavy chains of the same clones are depicted in FIG. 2. An overview about the CDR sequences, including references to the SEQ ID NOs, of the light and heavy chains of these antibodies is provided in Tables 1 and 2. The combinations of LCVRs and HCVRs observed in the clones, and the frequency of each of these combinations, are disclosed in Table 3.

The clones D005, E040 and F052 represent three of most abundant combinations of LCVR and HCVR (1A-1A, 2A-1A, and 3A-1A, cf. Table 3) and were thus chosen as representative clones for further analysis.

EXAMPLE 3

Expression and Purification of M2-Specific scFv-msFcγ2c Fusion Proteins

To investigate the effect of M2e-specific human antibodies on Influenza A infection in a mouse model, clones D005, E040 and F052 were expressed and purified as scFv-mouse Fc-γ2c (msFcγ2c) fusion proteins. The nucleotide sequences encoding the D005, E040 and F052 scFv-mouse Fc-γ2c (msFcγ2c) fusion proteins correspond to SEQ ID NOs:42, 44 and 46, respectively. The amino acid sequences of the D005, E040 and F052 scFv-mouse Fc-γ2c (msFcγ2c) fusion proteins correspond to SEQ ID NOs: 43, 45 and 47, respectively. The corresponding scFv coding regions were excised from the pCEP-SP-Sfi-Fc expression vectors with the restriction endonuclease SfiI and the resulting fragments were cloned into the expression vector pCEP-SP-Sfi-msFcγ2c (SEQ ID NO:41). The Sfi-digested fragments of monoclonal antibodies D005, E042, and F052 correspond to SEQ ID NOs 38, 39 and 40, respectively. These Sfi-fragments encode the entire scFv fragment of the corresponding antibody, including the linker sequence, but do not include the Fc domain.

Large-scale expression of scFv-msFcγ2c fusion proteins was done in HEK-293T cells. One day before transfection, $10^7$ 293T cells were plated onto a 14 cm tissue culture plate for each protein to be expressed. Cells were then transfected with the respective scFv-msFcγ2c fusion construct using Lipofectamine Plus (Invitrogen) according to the manufacturer's recommendations, incubated one day, and replated on three 14 cm dishes in the presence of 1 µg/ml puromycin. After three days of selection, puromycin-resistant cells were transferred to six 14 cm plates and grown to confluency. Finally, cells were transferred to a poly-L-lysine coated roller bottle. After 1-2 days medium was replaced by serum-free medium and supernatants containing the respective scFv-msFcγ2c fusion protein was collected every 3 days and filtered through a 0.22 µm Millex GV sterile filter (Millipore).

For each of the scFv-msFcγ2c fusion proteins, the consecutive harvests were pooled and applied to a protein A-sepharose column. The column was washed with 10 column volumes of phosphate-buffered saline (PBS), and bound protein eluted with 0.1 M Glycine pH 3.6. 1 ml fractions were collected in tubes containing 0.1 ml of 1 M Tris pH 7.5 for neutralization. Protein-containing fractions were analyzed by SDS-PAGE and pooled. The buffer was exchanged with PBS by dialysis using 10,000 MWCO Slide-A-Lyzer dialysis cassettes (Pierce). The purified proteins in PBS were then filtered through 0.22 µm Millex GV sterile filters (Millipore) and aliquotted. Working stocks were kept at 4° C., whereas aliquots for long-term storage were flash-frozen in liquid nitrogen and kept -80° C.

EXAMPLE 4

ELISA Analysis of scFv-msFcγ2c Fusion Protein Binding to M2-Derived Peptides

To confirm binding of scFv-msFcγ2c fusion proteins to M2e, an ELISA analysis was carried out with purified scFv-D005-msFcγ2c, scFv-E040-msFcγ2c and scFv-F052-msFcγ2c. Thus, ELISA plates were coated with M2e (SEQ ID NO:48) conjugated to RNAse A at a concentration of 4 µg/ml in phosphate-buffered saline (PBS), one hour at 37° C. The plates were then washed with wash buffer (PBS/0.05% Tween) and blocked for 1 h at 37° C. with 3% BSA in wash buffer. The plates were then washed again and incubated with serial dilutions of purified scFv-D005-msFcγ2c, scFv-E040-msFcγ2c and scFv-F052-msFcγ2c. Plates were incubated at room temperature for 1.5 h at 37° C. and then extensively washed with wash buffer. Bound scFv-Fc fusion proteins were then detected by a 1 h incubation at room temperature with a HRPO-labeled, Fcγ-specific, goat anti-mouse IgG antibody (Jackson ImmunoResearch Laboratories 115-035-071). After extensive washing with wash buffer, plates were developed with OPD solution (1 OPD tablet, 25 ml OPD buffer and 8 µl 30% $H_2O_2$) for 10 min and the reaction was stopped with 5% $H_2SO_4$ solution. Plates were then read at OD 450 nm on an ELISA reader (Biorad Benchmark). The antibodies scFv-D005-msFcγ2c, scFv-E040-msFcγ2c and scFv-F052-msFcγ2c were found to bind immobilized M2e with a high apparent affinity. The apparent affinity of the same antibodies towards immobilized M2e-short (SEQ ID NO:49) and M2e-VN (SEQ ID NO:50) was determined using the same experimental set-up. The apparent affinities for each combination of antibody and antigen are provided in Table 5. These values correspond well with the ones obtained with unpurified culture supernatants (described in Example 2).

TABLE 5

Apparent affinities of scFv-D005-msFcγ2c, scFv-E040-msFcγ2c and scFv-F052-msFcγ2c towards different versions of influenza M2 extracellular domain.

| Antibody | M2e | M2e-short | M2e-VN |
| --- | --- | --- | --- |
| D005 | 81.5 pM | 80.9 pM | 51.5 pM |
| E040 | 88.3 pM | 90.2 pM | 46.4 pM |
| F052 | 50.6 pM | 62.8 pM | 45.9 pM |

To further investigate binding of the scFv-msFcγ2c fusion proteins to different M2-derived peptides, also a competition ELISA was carried out. Thus, ELISA plates were coated with M2e conjugated to RNAse A at a concentration of 4 µg/ml in phosphate-buffered saline (PBS), over night at 4° C. The plates were then washed with wash buffer (PBS/0.05% Tween) and blocked for 2 h at 37° C. with 3% BSA in wash buffer. The plates were then washed again and incubated with purified scFv-D005-msFcγ2c, scFv-E040-msFcγ2c and scFv-F052-msFcγ2c at a concentration of 100 ng/ml in the absence or presence of increasing concentrations of M2e, an M2 extracellular domain peptide derived from H5N1 Influenza A VN1203 (M2e-VN; SEQ ID NO:50), or a shortened M2e peptide (M2e-short; SEQ ID NO:49) (Table 7). Plates were incubated at room temperature for 2 h and then extensively washed with wash buffer. Bound scFv-Fc fusion proteins were then detected by a 1 h incubation with a HRPO-labeled, Fcγ-specific, goat anti-mouse IgG antibody (Jackson ImmunoResearch Laboratories 115-035-071). After extensive washing with wash buffer, plates were developed with OPD solution and read on an ELISA reader as described above. Binding of each of the antibodies to immobilized M2e was inhibited by all three peptides to a similar extent, indicating that all three peptides were recognized equally well (Table 6).

TABLE 6

Inhibition of scFv-msFcγ2c binding to immobilized M2e by soluble M2 peptides. EC50 values (µM) of inhibition of binding are shown.

| scFv-msFcγ2c | M2e | M2e-VN | M2e-short |
| --- | --- | --- | --- |
| D005 | 18.8 | 32.5 | 27.5 |
| E040 | 21.3 | 43.2 | 35.5 |
| F052 | 22.0 | 50.8 | 46.8 |

TABLE 7

M2 variants used in this study.

| M2e variant | Abbreviation | Subtype | SEQ ID NO | M2 Sequence[2] |
|---|---|---|---|---|
| Consensus[1] | M2e | n/a | 48 | SLLTEVETPIRNEWGCRCNDSSD |
| Short | M2e-short | n/a | 49 | SLLTEVETPIRNEWGC |
| A/VN/1203/04 | M2e-VN | H5N1 | 50 | SLLTEVETPTRNEWEECRCSDSSD |
| A/PR/8/34 | M2-PR | H1N1 | 84 | SLLTEVETPIRNEWGCRCNGSSD PLTIAANIIGILHLTLWILDRLF FKCIYRRFKYGLKGGPSTEGVPK SMREEYRKEQQSAVDADDGHFVS IELE |
| A/VN/1203/04 | M2-VN/PR | H5N1 | 85 | SLLTEVETPTRNEWEECRCSDSSD PLTIAANIIGILHLTLWILDRLF FKCIYRRFKYGLKGGPSTEGVPK SMREEYRKEQQSAVDADDGHFVS IELE |

[1] M2e consensus sequence derived from H1, H2, and H3 subtypes of human Influenza A viruses.
[2] Variations from M2 consensus sequence are shown in bold (Tompkins et al. 2007, Emerging Infectious Diseases Vol. 13, No. 3, pp. 426-435, cf. Table therein).
All sequences are shown without the N-terminal Methionine, which is removed upon expression in vivo.

EXAMPLE 5

Binding of M2-Specific scFv-msFcγ2c Fusion Proteins to M2-Expressing L929 Cells The ability of the recombinant antibodies to recognize native M2 was assessed by analyzing their reactivity with L929-M2#E9 cells, a clone of L929 cells expressing full-length M2 derived from mouse-adapted H1N1 Influenza A PR8 (M2-PR; SEQ ID NO:84) (Table 7). Thus, L929-M2#E9 cells were brought to a single-cell suspension and incubated with 2-fold serial dilutions of, respectively, scFv-D005-msFcγ2c, scFv-E040-msFcγ2c or scFv-F052-msFcγ2c in FACS® buffer (phosphate-buffered saline containing 1% FCS). After a 1 h incubation on ice, cells were washed in FACS® buffer and bound antibodies detected by a half hour incubation on ice with Cy5-labeled goat anti-mouse antibody (Jackson Immuno, Cat No 115-176-071) in FACS buffer. After a final wash, the fluorescence intensity of the stained cells was analyzed by flow cytometry using a FACScalibur® (Becton Dickinson). The antibodies scFv-D005-msFcγ2c, scFv-E040-msFcγ2c and scFv-F052-msFcγ2c were found to bind native, cell surface-expressed M2-PR with a high affinity, with an EC50 of 0.68, 0.73 and 0.46 nM, respectively.

EXAMPLE 6

Protective Effect of M2-Specific scFv-msFcγ2c Fusion Proteins in a Mouse Model of Influenza A Infection The efficacy anti-M2 scFv-msFcγ2c antibodies in a prophylactic setting was tested in a mouse model of Influenza A infection. This model reflects most of the immunological and histological aspects of Influenza infection in humans and is therefore routinely used to assess the efficacy of anti-viral agents. Thus, six week old female C57BL/6 mice were injected intraperitoneally with 500 μg of scFv-D005-msFcγ2c, scFv-E040-msFcγ2c, scFv-F052-msFcγ2c or mouse IgG in PBS (6 mice per group). One day later, mice were bled in order to verify the presence of the antibodies in the blood by ELISA. Antibodies were readily detectable in the sera of all mice, except for one mouse receiving clone D005, which was subsequently removed from the analysis (not shown). Another day later (day 0), mice were infected intranasally with a lethal dose of mouse-adapted Influenza A virus PR8 (4×LD50) followed by monitoring of weight-loss and fever (temperature drop) for 12 days. Control mice treated with mouse IgG developed severe signs of morbidity, characterized by dramatic temperature drop and weight loss, within 5 to 6 days and invariably died on days 7 or 8 (FIG. 3C). In contrast, animals treated with M2-specific antibodies were almost completely protected from any signs of morbidity, developed hardly any signs of fever and lost weight only temporarily (FIG. 3A and B).

Figure 4:
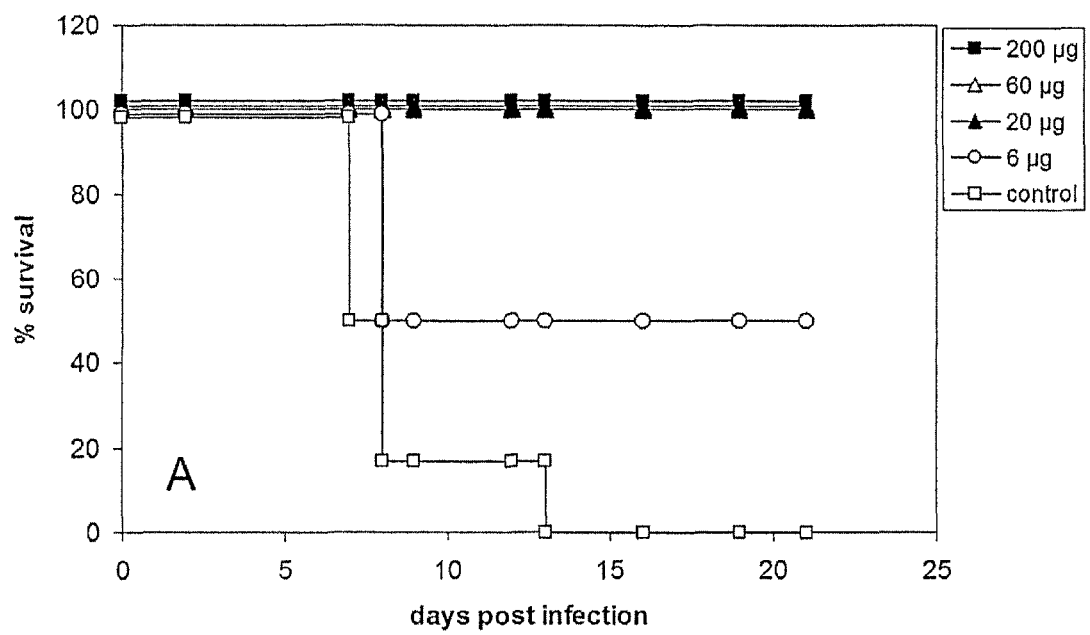
FIG. 4. Effect of scFv-D005-msFcγ2c on survival of Influenza-infected mice. (A) Dose titration. Mice were treated with the indicated amounts of antibody on day -2, infected with Influenza A virus PR8 on day 0, and survival was monitored for 21 days. (B) Therapeutic application of antibody. Mice were infected with Influenza A virus PR8 on day 0, treated with 200 µg of the antibody on the indicated days, and survival was monitored for 21 days. Control, mouse IgG on day -2.
Figure 4:
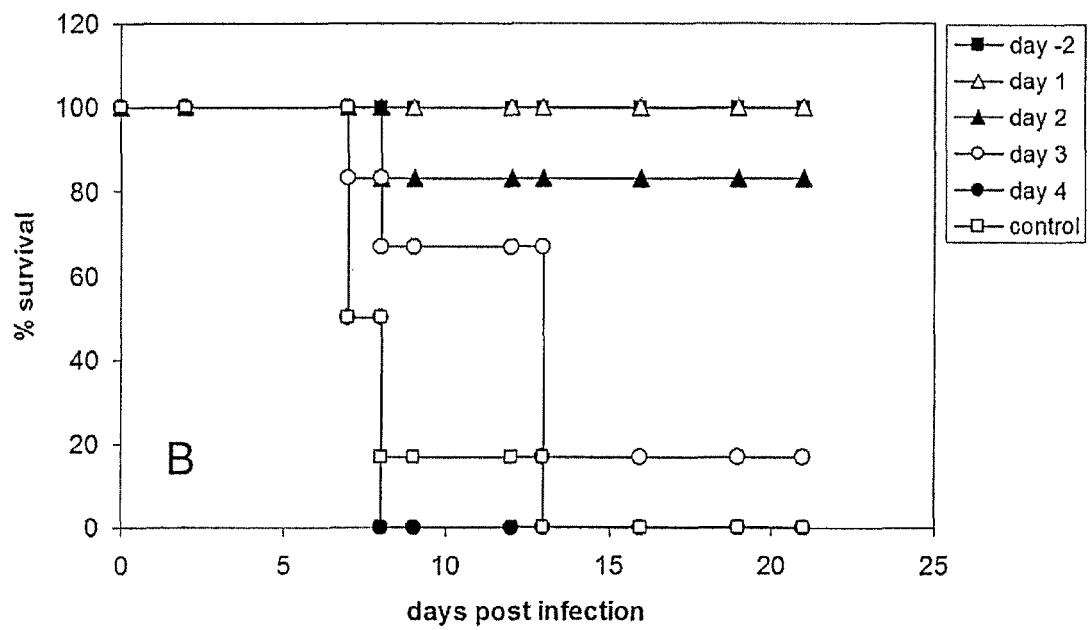

To determine the minimal amount of antibody required to achieve full protection of mice in a prophylactic setting, scFv-msFc-γ2c D005 was titrated. To this end, six week old female C57BL/6 mice were injected intraperitoneally with decreasing amounts of the antibody (200, 60, 20, or 6 μg per mouse) or, as a control, with 200 μg of mouse IgG (6 mice per group). One day later, mice were bled in order to verify the presence of the antibodies in the blood by ELISA. Antibodies were readily detectable in the sera of all mice, except for one mouse receiving the 60 μg dose, which was subsequently removed from the analysis (not shown). Another day later (day 0), animals were infected intranasally with a lethal dose of influenza A virus strain PR/8/34 (4×LD50) and monitored for 21 days (FIG. 4A). As expected, control mice quickly succumbed to the disease and were dead in less than two weeks. In contrast, antibody D005 showed protective activity at all doses tested. In groups of mice receiving 200, 60 or 20 μg antibody, all animals survived the lethal challenge. Even at the lowest dose of 6 μg D005, half of the mice recovered and survived infection, indicating that the M2-specific antibody is a potent prophylactic agent.

EXAMPLE 7

Therapeutic Activity of a M2-Specific scFv-msFcγ2c Fusion Protein in a Mouse Model of Influenza A Infection In view of the similarities of clones D005, E040 and F052 in sequence, affinity and prophylactic activity, only scFv-D005-msFcγ2c was tested in a therapeutic setting. Thus, six weeks old female C57BL/6 mice were infected intranasally with a lethal dose of mouse-adapted Influenza A virus PR8 ($4 \times LD_{50}$). 1, 2, or 3 days later, groups of mice were injected intraperitoneally with 200 μg of scFv-D005-msFcγ2c in PBS (6 mice per group). As controls, one group of mice each was injected with scFv-D005-msFcγ2c or mouse IgG two days prior to infection. Each mouse was bled one day after receiving antibody in order to verify the presence of the antibodies in the blood (not shown). The mice were observed closely to monitor signs of morbidity as well as mortality for a total of 21 days (FIG. 4B and not shown). All mice receiving the control antibody eventually died, whereas all mice receiving a prophylactic injection of scFv-D005-msFcγ2c two days prior to infection survived for at least 3 weeks. Significantly, therapeutic efficacy of the antibody could be shown in groups of mice treated as much as 3 days after infection. Survival rates of mice treated 1, 2 and 3 days after infection were 100, 83 and 17%, respectively. The measurement of survival rates generally corresponds to mortality (the proportion of deaths to a specified population), whereas morbidity general corresponds to the incidence of disease or the rate of sickness (in a specified population).

EXAMPLE 8

Construction, Expression, and Purification of Fully Human M2-Specific IgG1

Expression vectors allowing for expression of the clones D005, E040 and F052 as fully human IgG1κ were generated. Thus, DNA sequences encoding a human γ1 heavy chain shared by clones D005, E040 and F052, as well as each of the unique κ light chains were produced by total gene synthesis (SEQ ID NOs 30, 32, 34, and 36, by GeneArt AG, Germany). The heavy chain coding sequence was flanked by a AscI recognition site upstream and a PacI recognition site downstream of the open reading frame (cf. SEQ ID NO:30). The light chain coding sequences were flanked by NheI recognition sites upstream and PmeI recognition sites downstream of the respective open reading frame (cf. SEQ ID NOs 32, 34, and 36). The amino acid sequence of the entire human γ1 heavy chain, including the signal peptide, is depicted in SEQ ID NO:31. The amino acid sequences of the κ light chains of D005, E040 and F052 are depicted in SEQ ID NOs 33, 35 and 37, respectively.

Heavy and light chain coding regions were then combined into the EBNA-based expression vector pCB15 (disclosed as SEQ ID NO:104 of WO 2008/055795 A1). Thus, the heavy chain coding region was digested with the restriction enzymes AscI and PacI, and ligated into AscI-PacI digested pCB15, generating the plasmid pCB15-fh-HC-γ1-D005. This plasmid was then digested with the restriction enzymes NheI and PmeI and ligated to each of the NheI-PmeI digested light chain coding regions, generating the plasmids pCB15-fh-IgG1κ-D005, pCB15-fh-IgG1κ-E040 and pCB15-fh-IgG1κ-F052. Expression of IgG1κ-D005, IgG1κ-E040 and IgG1κ-F052 in HEK-293T cells, as well as purification by protein A-sepharose chromatography, was done as described for the scFv-Fc fusion proteins (Example 2).

EXAMPLE 9

Binding of a M2-Specific Fully Human IgG1 to M2-Expressing 293T Cells

In view of the similarities of clones D005, E040 and F052 in sequence, affinity and prophylactic activity, only IgG1-D005 was analyzed in more detail. The ability of the fully human mAb IgG1-D005 to recognize native, cell surface-expressed M2 was assessed by analyzing its reactivity with 293T cells expressing full-length M2 variants. Thus, 293T cells were transfected with a recombinant expression vector encoding the M2 protein of A/PR/8/34 (M2-PR, SEQ ID NO:84) or the fusion protein M2-VN/PR (SEQ ID NO:85), respectively. M2-VN/PR comprises an extracellular domain derived from H5N1 Influenza A VN1203 (M2e-VN, SEQ ID NO:50) which is fused to the N-terminus of the transmembrane and intercellular regions of M2-PR (cf. Table 7, the part of SEQ ID NO:84 which is shown in italics).

Transfected 293T cells were then brought to a single-cell suspension and incubated with 2-fold serial dilutions of IgG1-D005 in FACS buffer (phosphate-buffered saline containing 1% FCS). After a 1 h incubation on ice, cells were washed in FACS buffer and bound antibodies detected by a half hour incubation on ice with Cy5-labeled goat anti-human antibody in FACS buffer. After a final wash, the fluorescence-intensity of the stained cells was analyzed by flow cytometry using a FACScalibur (Becton Dickinson). The mAb IgG1-D005 bound native, cell surface-expressed M2-PR and M2-VN/PR with identical affinities, with an EC50 of 3.9 nM.

EXAMPLE 10

Figure 5:
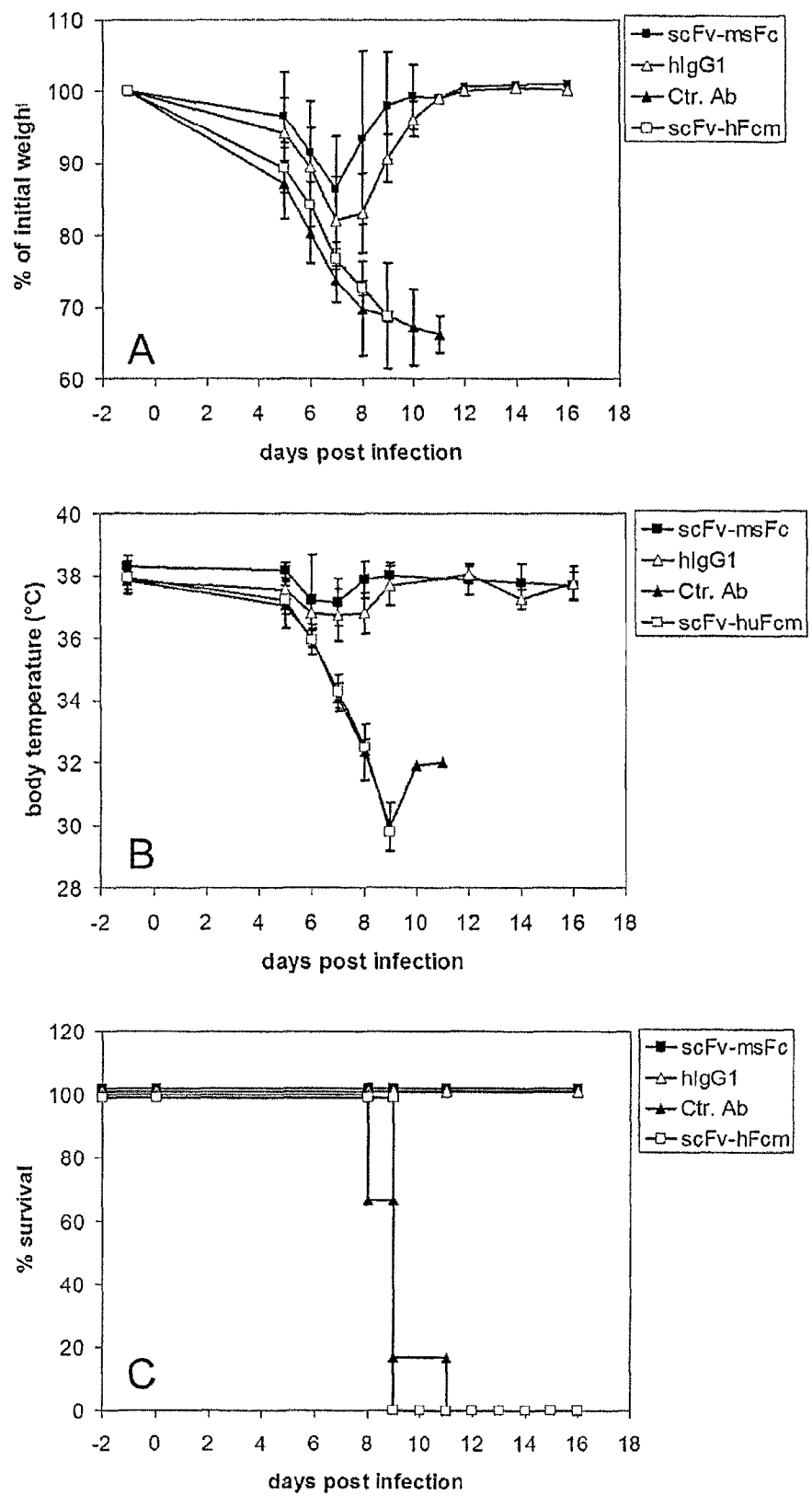
FIG. 5. Effect of M2-specific antibodies on Influenza-induced morbidity and mortality. Mice were treated with the antibody D005 in the indicated format on day -2, infected with Influenza A virus PR8 on day 0, and weight (A), body temperature (B) and survival (C) were monitored on the indicated days.

M2-Specific Fully Human IgG1 is Protective in a Mouse Model of Influenza A Infection and Requires Interaction with Fc Receptor In view of the similarities of clones D005, E040 and F052 in sequence, affinity and prophylactic activity, only antibody D005 was analyzed in more detail in a mouse model of Influenza A infection. On one hand, the prophylactic activity of fully human IgG1κ-D005 was tested and compared to the scFv-D005-msFcγ2c fusion protein. On the other hand, the involvement of antibody-dependent cellular cytotoxicity (ADCC) was investigated, by using a scFv-D005 antibody fused to a mutated human Fcγ1 incapable of binding to Fc receptors (scFv-D005-hFcm). Thus, six week old female C57BL/6 mice were injected intraperitoneally with equimolar amounts of IgG1-D005 (200 μg), scFv-D005-msFcγ2c (144 μg), scFv-D005-hFcm (144 μg), or human IgG (200 μg) in PBS (6 mice per group). One day later, mice were bled in order to verify the presence of the antibodies in the blood by ELISA. Antibodies were readily detectable in the sera of all mice (not shown). Another day later (day 0), mice were infected intranasally with a lethal dose of mouse-adapted Influenza A virus PR8 ($4 \times LD_{50}$) followed by monitoring of weight-loss and fever (temperature drop) for 16 days. Control mice treated with mouse IgG developed severe signs of morbidity, characterized by dramatic temperature drop and weight loss, within 6 to 7 days and died between days 8 and 11 (FIG. 5). In contrast, similar to animals treated with scFv-D005-msFcγ2c, those treated with hIgG1κ-D005 were almost completely protected from any signs of morbidity, developed hardly any signs of fever and lost weight only temporarily (FIG. 5A and B). Thus, fully human IgG1k-D005 has a strong prophylactic activity in mice and is equipotent to scFv-D005-msFcγ2c. Significantly, mice treated with scFv-D005-hFcm were not protected and developed severe signs of morbidity similar to mice treated with the control IgG (FIG. 5A and B). Consequently, all animals treated with scFv-D005-hFcm succumbed to disease and were dead by day 9 (FIG. 5C). Thus, Fc receptor interaction is required for protection, suggesting that ADCC is a major component of the prophylactic activity.

EXAMPLE 11

Determination of Affinities by Friguet-ELISA

The dissociation constants (Kd) of antibody binding to M2e in solution were determined using an ELISA-based method essentially as described (Friguet B. et al., 1985, J. Immunol. Meth. 77, 305-319). Briefly, a 10 ng/ml solution of, respectively, scFv-D005-msFcγ2c, scFv-E040-msFcγ2c or scFv-F052-msFcγ2c, was incubated in the presence of different concentrations of RNAse conjugated to influenza A M2e (SEQ ID NO:48) (3-fold serial dilutions ranging from 10 nM to 0.17 with respect to the content of influenza A M2e) in PBS/1% BSA. After 2 h at room temperature, free antibody was detected by a classical ELISA similar to the one described in Example 4. For this, ELISA plates that had been coated with RNAse-M2e conjugate at a concentration of 20 ng/ml at 4° C. overnight were washed with wash buffer (PBS/0.05% Tween) and blocked for 1 h at 37° C. with 3% BSA in wash buffer. The plates were then washed again and incubated with the solution binding reactions for 30 min at room temperature. After extensive washing with wash buffer, bound scFv-Fcγ2c fusion proteins were detected by a 1 h incubation at room temperature with a HRPO-labeled, Fcγ-specific, goat anti-mouse IgG antibody (Jackson ImmunoResearch Laboratories 115-035-071). After extensive washing with wash buffer, plates were developed with OPD solution (1 OPD tablet, 25 ml OPD buffer and 8 µl 30% $H_2O_2$) for 15 min and the reaction was stopped with 5% $H_2SO_4$ solution. Plates were then read at OD 450 nm on an ELISA reader (Biorad Benchmark). The Kd values were determined as the EC50 of the ELISA signal as a function of the RNAse-M2e concentration present in the solution binding reaction. The antibodies scFv-D005-msFcγ2c, scFv-E040-msFcγ2c and scFv-F052-msFcγ2c were found to bind soluble RNase-M2e with a high affinity. Kd values were found to be 4 pM (D005), 13 pM (E040) and 6 pM (F052).

The same assay was repeated under otherwise identical conditions using free M2e peptide (SEQ ID NO:48) instead of the RNAse-M2e conjugate. The antibodies scFv-D005-msFcγ2c, scFv-E040-msFcγ2c and scFv-F052-msFcγ2c were found to bind soluble M2e peptide with a high affinity. Kd values were found to be 4 nM (D005, E040) and 5 nM (F052).

EXAMPLE 12

Preferential Binding of Antibody D005 to Cell-Associated M2

Figure 6:
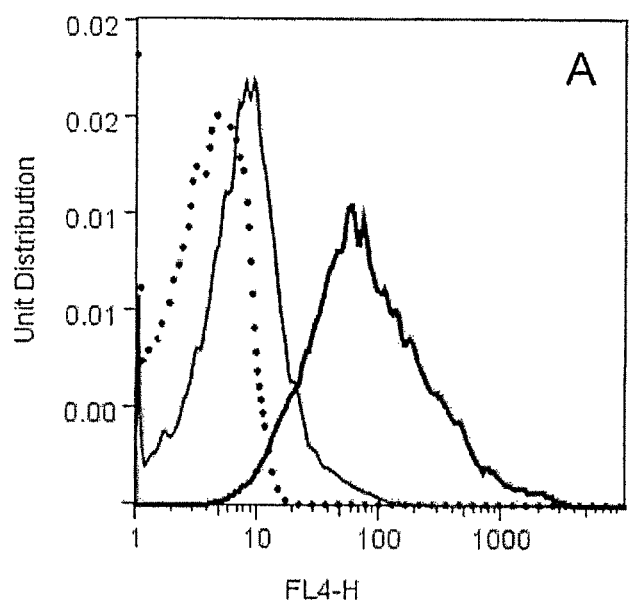
FIG. 6. Binding to cell surface M2 in the presence of soluble M2e peptide. L929/M2#E9 cells were stained with antibody 14C2 (A) or D005 (B) in the presence (solid line) or absence (heavy line) of soluble M2e peptide and analyzed by FACS. Dotted line, staining with fluorescently labelled secondary antibody alone.
Figure 6:
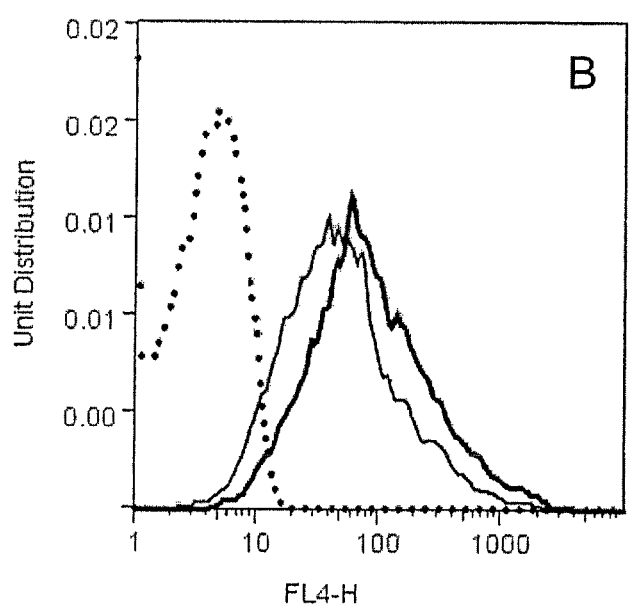

The ability of antibody D005 to distinguish between native, cell-associated M2 and an unstructured, soluble M2e peptide was assessed by flow cytometry. For comparison, mouse monoclonal antibody 14C2 was also analyzed (Zebedee et al., 1988, J. Virol. 62(8): 2762-2772). Thus, scFv-D005-msFcγ2c and mAb 14C2 were incubated in FACS buffer at a concentration of 0.5 µg/ml in the presence or absence of 12 nM soluble M2e peptide for 1 hour on ice. The prebound antibodies were then used for staining of L929-M2#E9 cells. Thus, L929-M2#E9 cells were brought to a single-cell suspension and incubated with the prebound antibodies or, as a control, with FACS buffer. After a 50 min incubation on ice, cells were washed in FACS buffer and bound antibodies detected by a 20 min incubation on ice with Cy5-labeled goat anti-mouse antibody (Jackson Immuno, Cat No 115-176-071) in FACS buffer. After a final wash, the fluorescence intensity of the stained cells was analyzed by flow cytometry using a FACScalibur® (Becton Dickinson) (FIG. 6). Both antibodies were found to bind native, cell surface-expressed M2 with similar efficiency in the absence of peptide. However, in the presence of peptide, mouse mAb 14C2 did not efficiently recognize L292/M2#E9 cells. In contrast, antibody scFv-D005-msFcγ2c efficiently stained the cells despite the presence of an excess of competing peptide. This indicates that antibody D005, but not mAb 14C2, may bind a conformational epitope only present in native, cell-surface M2.

EXAMPLE 13

Direct Recognition of Virus Particles by Antibody D005

Figure 7:
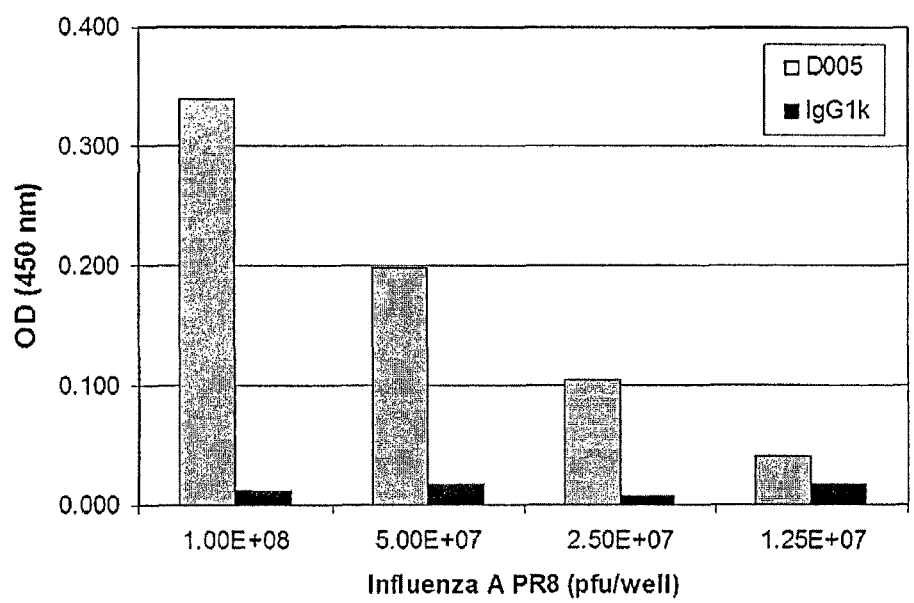
FIG. 7. Direct binding of antibody D005 to Influenza A PR8 virus particles. The indicated amount of virus was captured on wells of an ELISA plate previously coated with anti-HA antibody. Virus was detected with hIgG1k-D005 or an irrelevant isotype control.

To investigate the ability of antibody D005 to directly bind to Influenza A virus particles, a capture ELISA was carried out. Thus, wells of an ELISA plate were coated overnight at 4° C. with HA-specific mouse mAb H37-80 at a concentration of 10 µg/ml in coating buffer. The plate was then washed with wash buffer (PBS/0.05% Tween) and blocked for 3 h at 37° C. with 5% BSA in wash buffer. The plate was then washed again and incubated with $10^8$, $5 \times 10^7$, $2.5 \times 10^7$, or $1.25 \times 10^7$ pfu Influenza A PR8 per well in wash buffer/1% BSA. After 1 hour incubation at room temperature, the plate was washed again and incubated with 1 µg/ml fully-human IgG1k-D005 or an isotype-matched control antibody (human IgG1k, Sigma, Cat. No. 15154) in wash buffer/1% BSA. After 1 hour incubation at room temperature, the plate was washed again and incubated with a 1:1000 dilution of HRPO-conjugated goat anti-human IgG (Jackson Immuno, Cat No 109-035-098) in wash buffer/1% BSA. After 1 hour incubation at room temperature, the plate was washed extensively with wash buffer, developed with OPD solution and read on an ELISA reader as described above. Whereas no detectable ELISA signal was obtained with the control antibody, hIgG1k-D005 readily detected captured Influenza A particles in a dose-dependent manner (FIG. 7).

EXAMPLE 14

Analysis of Crossreactivity and Fine Mapping of Epitope Recognized by Antibody D005

Figure 8:
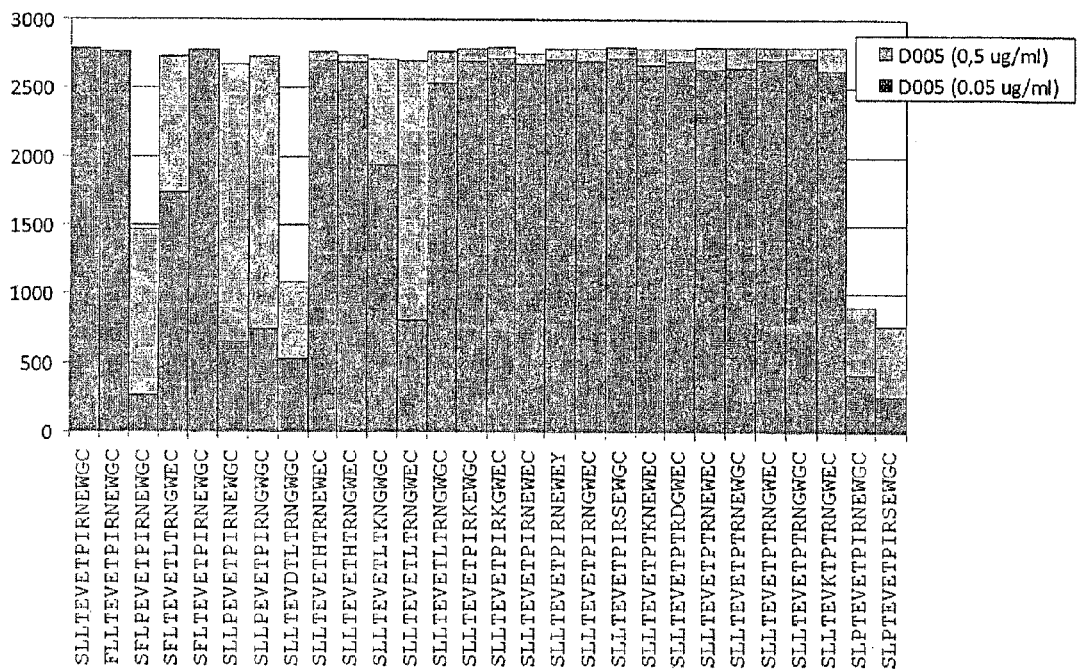
FIG. 8. Characterization of binding specificity of antibody D005. (A) Reactivity of IgG1k-D005 with M2e-derived peptides from different strains of Influenza A. (B) Epitope mapping.

Crossreactivity of antibody D005 with M2 sequences derived from different Influenza A strains was analyzed by testing the binding of IgG1k-D005 to solid phase bound peptide variants (analysis performed by Pepscan Presto BV, Lelystad, the Netherlands). Since it was previously found that the epitope recognized by D005 is comprised within the 16 amino acid peptide M2e-short (SEQ ID NO:49) (Example 4), only peptides spanning this region were synthesized. In doing so, 35 of the 23-mer peptides listed in Table 4 (SEQ IDs NO:48, 50-59, 61-83, and 90-92) were covered by 28 different 16-mer peptides. Binding was assayed at two antibody concentrations, 0.5 µg/ml and 0.05 µg/ml, revealing that antibody D005 is broadly cross-reactive. Significantly, all peptides tested were recognized, and 19 of the peptides were recognized as well as the one corresponding to the M2e consensus sequence (FIG. 8A).

The minimal epitope was determined in a similar manner, by testing the binding of IgG1k-D005 to solid phase bound variants of a peptide corresponding to peptide M2e-short (SEQ ID NO:49) (analysis performed by Pepscan Presto BV, Lelystad, the Netherlands). Three types of analyses were done: first, N- and C-terminal deletions; second, epitope scanning by synthesizing all 105 different 3 to 16 mer variants; and third, point mutations by synthesiszing all 304 possible single positional variants. The 3 analyses yielded comparable results (FIG. 8B). N-/C-terminal deletion and epitope scanning analyses narrowed down the region recognized by D005 to the 8-mer peptide LLTEVETP.

---

The invention claimed is:

1. An isolated monoclonal antibody, wherein said monoclonal antibody is specifically binding influenza M2e antigen, and wherein said monoclonal antibody is a human monoclonal antibody, and wherein said antibody comprises at least one antigen binding site, wherein said antigen binding site comprises:
  (a) one light chain variable region (LCVR), wherein said LCVR comprises: (i) one light chain complementarity determining region (LC CDR) 1, wherein said LC CDR1 consists of the peptide of any one of SEQ ID NOs 1, 2, 3, 4, 5, and 6; (ii) one LC CDR2, wherein said LC CDR2 consists of the peptide of SEQ ID NO:7; and (iii) one LC CDR3, wherein said LC CDR3 consists of the peptide of any one of SEQ ID NOs 8, 9, 10, and 11; and
  (b) one heavy chain variable region (HCVR), wherein said HCVR comprises: (i) one heavy chain complementarity determining region (HC CDR) 1, wherein said HC CDR1 consists of the peptide of SEQ ID NO:12; (ii) one HC CDR2, wherein said HC CDR2 consists of the peptide of any one of SEQ ID NOs 13 and 14; and (iii) one HC CDR3, wherein said HC CDR3 consists of the peptide of any one of SEQ ID NOs 15, 16, 17, 18, and 19.

2. The monoclonal antibody of claim 1, wherein said at least one antigen binding site recognizes an epitope comprised by the amino acid sequence LLTEVETP (SEQ ID NO: 93).

3. The monoclonal antibody of claim 1, wherein
  said LC CDR1 consists of the peptide of any one of SEQ ID NOs 1, 4 and 6,
  said LC CDR2 consists of the peptide of SEQ ID NO: 7,
  said LC CDR3 consists of the peptide of SEQ ID NO: 8,
  said HC CDR1 consists of the peptide of SEQ ID NO: 12,
  said HC CDR2 consists of the peptide of SEQ ID NO: 13, and
  said HC CDR3 consists of the peptide of SEQ ID NO: 15.

4. The monoclonal antibody of claim 3, wherein
  said LC CDR1 consists of the peptide of SEQ ID NO: 1,
  said LC CDR2 consists of the peptide of SEQ ID NO: 7,
  said LC CDR3 consists of the peptide of SEQ ID NO: 8,
  said HC CDR1 consists of the peptide of SEQ ID NO: 12,
  said HC CDR2 consists of the peptide of SEQ ID NO: 13, and
  said HC CDR3 consists of the peptide of SEQ ID NO: 15.

5. The monoclonal antibody of claim 1, wherein position 5 to 113 of said LCVR consists of the peptide of any one of SEQ ID NOs 20, 21 and 22, and wherein preferably position 1 to 4 of said LCVR consists of the peptide of SEQ ID NO: 24.

6. The monoclonal antibody of claim 1, wherein position 7 to 121 of said HCVR consists of the peptide of SEQ ID NO: 23, and wherein position 1 to 6 of said LCVR consists of the peptide of SEQ ID NO: 25.

7. The monoclonal antibody of claim 1, wherein position 5 to 113 of said LCVR consists of the peptide of any one of SEQ ID NOs 20, 21 and 22, and wherein position 7 to 121 of said HCVR consists of the peptide of SEQ ID NO: 23.

8. The monoclonal antibody of claim 1, wherein position 5 to 113 of said LCVR consists of the peptide of SEQ ID NO: 20, and wherein position 7 to 121 of said HCVR consists of the peptide of SEQ ID NO: 23, and wherein position 1 to 4 of said LCVR consists of the peptide of SEQ ID NO: 24, and wherein further position 1 to 6 of said HCVR consists of the peptide of SEQ ID NO: 25.

9. The monoclonal antibody of claim 1, wherein said monoclonal antibody comprises at least one light chain, and wherein said monoclonal antibody further comprises at least one heavy chain, wherein said light chain comprises the amino acid sequence of any one of SEQ ID NOs 26, 27, and 28, and wherein said heavy chain comprises the amino acid of SEQ ID NO: 29.

10. The monoclonal antibody of claim 1, wherein said influenza M2e antigen is the extracellular domain of the influenza A M2 protein, and wherein said influenza M2e antigen is the peptide of any one of SEQ ID NOs 48 to 83 and 90 to 92.

11. The monoclonal antibody of claim 10, wherein the dissociation constant (Kd) of said monoclonal antibody and said influenza M2e antigen is at most 100 nM or less and wherein said influenza M2e antigen is SEQ ID NO: 48.

12. A pharmaceutical composition comprising the monoclonal antibody of claim 1, wherein preferably said pharmaceutical composition further comprises a pharmaceutically acceptable carrier, diluent or excipient.

13. A method of treating and/or preventing influenza A virus infection, said method comprising administering to a subject an effective amount of the monoclonal antibody of claim 1, wherein said subject is a human.

14. A method of treating and/or preventing influenza A virus infection, said method comprising administering to a subject an effective amount of the pharmaceutical composition of claim 12.

15. An isolated polynucleotide comprising a nucleic acid encoding the monoclonal antibody of claim 1.

16. An isolated host cell comprising the isolated polynucleotide of claim 15 or at least one expression vector comprising the isolated polynucleotide of claim 15.

17. The monoclonal antibody of claim 1, wherein position 5 to 113 of said LCVR consists of the peptide of any one of SEQ ID NOs 20, 21 and 22.

18. The monoclonal antibody of claim 1, wherein position 7 to 121 of said HCVR consists of the peptide of SEQ ID NO: 23.

19. The monoclonal antibody of claim 1, wherein position 5 to 113 of said LCVR consists of the peptide of SEQ ID NO: 20, and wherein position 7 to 121 of said HCVR consists of the peptide of SEQ ID NO: 23.

20. The monoclonal antibody of claim 1, wherein said monoclonal antibody comprises at least one light chain, and wherein said monoclonal antibody further comprises at least one heavy chain, wherein said light chain consists of the amino acid sequence of any one of SEQ ID NOs 26, 27, and 28, and wherein said heavy chain consists of the amino acid of SEQ ID NO: 29.

21. The monoclonal antibody of claim 10, wherein the dissociation constant (Kd) of said monoclonal antibody and said influenza M2e antigen is at most 10 nM or less, and wherein said influenza M2e antigen is SEQ ID NO: 48.

* * * * *

UNITED STATES PATENT AND TRADEMARK OFFICE
CERTIFICATE OF CORRECTION

PATENT NO. : 8,460,670 B2
APPLICATION NO. : 13/132658
DATED : June 11, 2013
INVENTOR(S) : Martin F. Bachmann et al.

It is certified that error appears in the above-identified patent and that said Letters Patent is hereby corrected as shown below:

In the Claims:

Col. 114, claim 5 should read as follows:

5. The monoclonal antibody of claim 1, wherein position 5 to 113 of said LCVR consists of the peptide of any one of SEQ ID NOs 20, 21 and 22, and wherein position 1 to 4 of said LCVR consists of the peptide of SEQ ID NO: 24.

Col. 115, claim 12 should read as follows:

12. A pharmaceutical composition comprising the monoclonal antibody of claim 1, wherein said pharmaceutical composition further comprises a pharmaceutically acceptable carrier, diluent or excipient.

Signed and Sealed this
Sixteenth Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,460,670 B2  
APPLICATION NO. : 13/132658  
DATED : June 11, 2013  
INVENTOR(S) : Martin F. Bachmann et al.

Page 1 of 1

It is certified that error appears in the above-identified patent and that said Letters Patent is hereby corrected as shown below:

In the Claims:

Col. 114, lines 42 - 45, claim 5 should read as follows:

5. The monoclonal antibody of claim 1, wherein position 5 to 113 of said LCVR consists of the peptide of any one of SEQ ID NOs 20, 21 and 22, and wherein position 1 to 4 of said LCVR consists of the peptide of SEQ ID NO: 24.

Col. 115, lines 9 - 12, claim 12 should read as follows:

12. A pharmaceutical composition comprising the monoclonal antibody of claim 1, wherein said pharmaceutical composition further comprises a pharmaceutically acceptable carrier, diluent or excipient.

This certificate supersedes the Certificate of Correction issued July 16, 2013.

Signed and Sealed this  
Thirteenth Day of August, 2013

Teresa Stanek Rea  
*Acting Director of the United States Patent and Trademark Office*

SEQUENCE LISTING

```
<160> NUMBER OF SEQ ID NOS: 93

<210> SEQ ID NO 1
<211> LENGTH: 12
<212> TYPE: PRT
<213> ORGANISM: Homo sapiens

<400> SEQUENCE: 1

Gln Ser Val Leu Tyr Thr Ser Asn Asn Lys Asn Tyr
1               5                   10

<210> SEQ ID NO 2
<211> LENGTH: 12
<212> TYPE: PRT
<213> ORGANISM: Homo sapiens

<400> SEQUENCE: 2

Gln Ser Val Leu Asn Thr Ser Asn Asn Lys Asn Tyr
1               5                   10

<210> SEQ ID NO 3
<211> LENGTH: 12
<212> TYPE: PRT
<213> ORGANISM: Homo sapiens

<400> SEQUENCE: 3

Gln Ser Val Leu His Thr Ser Asn Asn Lys Asn Tyr
1               5                   10

<210> SEQ ID NO 4
<211> LENGTH: 12
<212> TYPE: PRT
<213> ORGANISM: Homo sapiens

<400> SEQUENCE: 4

Gln Ser Val Leu Tyr Ser Ser Asn Asn Glu Asn Tyr
1               5                   10

<210> SEQ ID NO 5
<211> LENGTH: 12
<212> TYPE: PRT
<213> ORGANISM: Homo sapiens

<400> SEQUENCE: 5

Gln Ser Val Leu Tyr Ser Ser Asn Asn Glu Asp Tyr
1               5                   10

<210> SEQ ID NO 6
<211> LENGTH: 12
<212> TYPE: PRT
<213> ORGANISM: Homo sapiens

<400> SEQUENCE: 6

Gln Ser Leu Leu Tyr Ser Ser Asn Asn Lys Asn Tyr
1               5                   10
```

```
<210> SEQ ID NO 7
<211> LENGTH: 3
<212> TYPE: PRT
<213> ORGANISM: Homo sapiens

<400> SEQUENCE: 7

Trp Ala Ser
1

<210> SEQ ID NO 8
<211> LENGTH: 9
<212> TYPE: PRT
<213> ORGANISM: Homo sapiens

<400> SEQUENCE: 8

Gln Gln Tyr Phe Met Thr Pro Ile Thr
1               5

<210> SEQ ID NO 9
<211> LENGTH: 9
<212> TYPE: PRT
<213> ORGANISM: Homo sapiens

<400> SEQUENCE: 9

Gln Gln Tyr Phe Met Ala Pro Ile Thr
1               5

<210> SEQ ID NO 10
<211> LENGTH: 9
<212> TYPE: PRT
<213> ORGANISM: Homo sapiens

<400> SEQUENCE: 10

Gln Gln Tyr Phe Val Thr Pro Ile Thr
1               5

<210> SEQ ID NO 11
<211> LENGTH: 9
<212> TYPE: PRT
<213> ORGANISM: Homo sapiens

<400> SEQUENCE: 11

Gln Gln Tyr Phe Met Thr Pro Ile Ala
1               5

<210> SEQ ID NO 12
<211> LENGTH: 8
<212> TYPE: PRT
<213> ORGANISM: Homo sapiens

<400> SEQUENCE: 12

Gly Leu Asn Phe Gly Asp Tyr Pro
1               5

<210> SEQ ID NO 13
<211> LENGTH: 10
<212> TYPE: PRT
<213> ORGANISM: Homo sapiens

<400> SEQUENCE: 13

Ile Lys Ser Lys Ser Tyr Gly Val Thr Thr
1               5                   10

<210> SEQ ID NO 14
```

```
<211> LENGTH: 10
<212> TYPE: PRT
<213> ORGANISM: Homo sapiens

<400> SEQUENCE: 14

Ile Lys Ser Lys Pro Tyr Gly Val Thr Thr
1               5                   10

<210> SEQ ID NO 15
<211> LENGTH: 12
<212> TYPE: PRT
<213> ORGANISM: Homo sapiens

<400> SEQUENCE: 15

Thr Ser Ser Ser Gly Phe Leu Tyr Tyr Phe Asp Tyr
1               5                   10

<210> SEQ ID NO 16
<211> LENGTH: 12
<212> TYPE: PRT
<213> ORGANISM: Homo sapiens

<400> SEQUENCE: 16

Thr Ser Ser Ser Gly Phe Leu Tyr Tyr Phe Asp His
1               5                   10

<210> SEQ ID NO 17
<211> LENGTH: 12
<212> TYPE: PRT
<213> ORGANISM: Homo sapiens

<400> SEQUENCE: 17

Thr Ser Ser Ser Ser Phe Leu Tyr Tyr Phe Asp Tyr
1               5                   10

<210> SEQ ID NO 18
<211> LENGTH: 12
<212> TYPE: PRT
<213> ORGANISM: Homo sapiens

<400> SEQUENCE: 18

Thr Ser Asn Ser Gly Phe Leu Tyr Tyr Phe Asp Tyr
1               5                   10

<210> SEQ ID NO 19
<211> LENGTH: 12
<212> TYPE: PRT
<213> ORGANISM: Homo sapiens

<400> SEQUENCE: 19

Thr Ser Ser Ser Gly Phe Ser Tyr Tyr Phe Asp Tyr
1               5                   10

<210> SEQ ID NO 20
<211> LENGTH: 109
<212> TYPE: PRT
<213> ORGANISM: Homo sapiens

<400> SEQUENCE: 20

Thr Gln Ser Pro Asp Ser Leu Ala Val Ser Leu Gly Glu Arg Ala Thr
1               5                   10                  15

Ile Asn Cys Lys Ser Ser Gln Ser Val Leu Tyr Thr Ser Asn Asn Lys
            20                  25                  30

Asn Tyr Leu Gly Trp Tyr Gln Gln Lys Pro Gly Gln Pro Pro Asn Leu
        35                  40                  45
```

```
Leu Ile Tyr Trp Ala Ser Thr Arg Glu Ser Gly Val Pro Asp Arg Phe
    50                  55                  60

Ser Gly Ser Gly Ser Gly Thr Asp Phe Thr Leu Thr Ile Asn Ser Val
65                  70                  75                  80

Gln Ala Glu Asp Val Ala Val Tyr Tyr Cys Gln Gln Tyr Phe Met Thr
                85                  90                  95

Pro Ile Thr Phe Gly Gln Gly Thr Arg Leu Glu Ile Lys
            100                 105

<210> SEQ ID NO 21
<211> LENGTH: 109
<212> TYPE: PRT
<213> ORGANISM: Homo sapiens

<400> SEQUENCE: 21

Thr Gln Ser Pro Asp Ser Leu Ala Val Ser Leu Gly Glu Arg Ala Thr
1               5                   10                  15

Ile Asn Cys Lys Ser Ser Gln Ser Val Leu Tyr Ser Ser Asn Asn Glu
            20                  25                  30

Asn Tyr Leu Ala Trp Tyr Gln Gln Lys Pro Gly Gln Pro Pro Lys Leu
        35                  40                  45

Leu Ile Tyr Trp Ala Ser Thr Arg Glu Ser Gly Val Pro Asp Arg Phe
    50                  55                  60

Ser Gly Ser Gly Ser Gly Thr Asp Phe Thr Leu Thr Ile Asn Ser Val
65                  70                  75                  80

Gln Ala Glu Asp Val Ala Val Tyr Tyr Cys Gln Gln Tyr Phe Met Thr
                85                  90                  95

Pro Ile Thr Phe Gly Gln Gly Thr Arg Leu Glu Ile Lys
            100                 105

<210> SEQ ID NO 22
<211> LENGTH: 109
<212> TYPE: PRT
<213> ORGANISM: Homo sapiens

<400> SEQUENCE: 22

Thr Gln Ser Pro Asp Ala Leu Ala Val Ser Leu Gly Glu Arg Ala Thr
1               5                   10                  15

Ile Asn Cys Lys Ser Ser Gln Ser Leu Leu Tyr Ser Ser Asn Asn Lys
            20                  25                  30

Asn Tyr Leu Ala Trp Tyr Gln Lys Lys Pro Gly Gln Pro Pro Lys Leu
        35                  40                  45

Leu Ile Tyr Trp Ala Ser Thr Arg Glu Ser Gly Val Pro Asp Arg Phe
    50                  55                  60

Ser Gly Ser Gly Ser Gly Thr Glu Phe Thr Leu Thr Ile Asn Ser Val
65                  70                  75                  80

Gln Ala Glu Asp Val Ala Val Tyr Tyr Cys Gln Gln Tyr Phe Met Thr
                85                  90                  95

Pro Ile Thr Phe Gly Gln Gly Thr Arg Leu Glu Ile Lys
            100                 105

<210> SEQ ID NO 23
<211> LENGTH: 115
<212> TYPE: PRT
<213> ORGANISM: Homo sapiens

<400> SEQUENCE: 23

Ser Gly Gly Ala Leu Val Gln Pro Gly Arg Ser Leu Arg Leu Ser Cys
```

```
                            1               5                  10                 15
Arg Thr Ser Gly Leu Asn Phe Gly Asp Tyr Pro Ile Asn Trp Val Arg
                20                  25                 30

Gln Ala Pro Gly Lys Gly Leu Glu Trp Val Gly Phe Ile Lys Ser Lys
            35                  40                 45

Ser Tyr Gly Val Thr Thr Glu Phe Ala Ala Ser Val Glu Gly Arg Phe
    50                  55                 60

Thr Ile Ser Arg Asp Asp Ser Arg Gly Ile Ala Tyr Leu Gln Met Asn
65                  70                 75                  80

Ser Leu Lys Thr Glu Asp Thr Ala Val Tyr Tyr Cys Thr Ser Ser Ser
                85                  90                 95

Gly Phe Leu Tyr Tyr Phe Asp Tyr Trp Gly Gln Gly Thr Leu Val Thr
            100                 105                110

Val Ser Ser
        115
```

<210> SEQ ID NO 24
<211> LENGTH: 4
<212> TYPE: PRT
<213> ORGANISM: Homo sapiens

<400> SEQUENCE: 24

```
Asp Ile Val Met
1
```

<210> SEQ ID NO 25
<211> LENGTH: 6
<212> TYPE: PRT
<213> ORGANISM: Homo sapiens

<400> SEQUENCE: 25

```
Glu Val Gln Leu Val Glu
1               5
```

<210> SEQ ID NO 26
<211> LENGTH: 220
<212> TYPE: PRT
<213> ORGANISM: Homo sapiens

<400> SEQUENCE: 26

```
Asp Ile Val Met Thr Gln Ser Pro Asp Ser Leu Ala Val Ser Leu Gly
1               5                  10                 15

Glu Arg Ala Thr Ile Asn Cys Lys Ser Ser Gln Ser Val Leu Tyr Thr
                20                  25                 30

Ser Asn Asn Lys Asn Tyr Leu Gly Trp Tyr Gln Gln Lys Pro Gly Gln
            35                  40                 45

Pro Pro Asn Leu Leu Ile Tyr Trp Ala Ser Thr Arg Glu Ser Gly Val
    50                  55                 60

Pro Asp Arg Phe Ser Gly Ser Gly Ser Gly Thr Asp Phe Thr Leu Thr
65                  70                 75                  80

Ile Asn Ser Val Gln Ala Glu Asp Val Ala Val Tyr Tyr Cys Gln Gln
                85                  90                 95

Tyr Phe Met Thr Pro Ile Thr Phe Gly Gln Gly Thr Arg Leu Glu Ile
            100                 105                110

Lys Arg Thr Val Ala Ala Pro Ser Val Phe Ile Phe Pro Pro Ser Asp
        115                 120                125

Glu Gln Leu Lys Ser Gly Thr Ala Ser Val Val Cys Leu Leu Asn Asn
    130                 135                140
```

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 27
<211> LENGTH: 220
<212> TYPE: PRT
<213> ORGANISM: Homo sapiens

<400> SEQUENCE: 27

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Glu Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Val Gln Ala Glu Asp Val Ala Val Tyr Tyr Cys Gln Gln
                85                  90                  95

Tyr Phe Met Thr Pro Ile Thr Phe Gly Gln Gly Thr Arg Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 28
<211> LENGTH: 220
<212> TYPE: PRT
<213> ORGANISM: Homo sapiens

<400> SEQUENCE: 28

Asp Ile Val Met Thr Gln Ser Pro Asp Ala Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Asn Lys Asn Tyr Leu Ala Trp Tyr Gln Lys Lys Pro Gly Gln
```

```
                35                  40                  45
Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Glu Phe Thr Leu Thr
65                  70                  75                  80

Ile Asn Ser Val Gln Ala Glu Asp Val Ala Val Tyr Tyr Cys Gln Gln
                85                  90                  95

Tyr Phe Met Thr Pro Ile Thr Phe Gly Gln Gly Thr Arg Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 29
<211> LENGTH: 451
<212> TYPE: PRT
<213> ORGANISM: Homo sapiens

<400> SEQUENCE: 29

Glu Val Gln Leu Val Glu Ser Gly Gly Ala Leu Val Gln Pro Gly Arg
1               5                   10                  15

Ser Leu Arg Leu Ser Cys Arg Thr Ser Gly Leu Asn Phe Gly Asp Tyr
            20                  25                  30

Pro Ile Asn Trp Val Arg Gln Ala Pro Gly Lys Gly Leu Glu Trp Val
        35                  40                  45

Gly Phe Ile Lys Ser Lys Ser Tyr Gly Val Thr Thr Glu Phe Ala Ala
    50                  55                  60

Ser Val Glu Gly Arg Phe Thr Ile Ser Arg Asp Asp Ser Arg Gly Ile
65                  70                  75                  80

Ala Tyr Leu Gln Met Asn Ser Leu Lys Thr Glu Asp Thr Ala Val Tyr
                85                  90                  95

Tyr Cys Thr Ser Ser Gly Phe Leu Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
```

```
                195                 200                 205
Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 30
<211> LENGTH: 1413
<212> TYPE: DNA
<213> ORGANISM: Homo sapiens
<220> FEATURE:
<221> NAME/KEY: sig_peptide
<222> LOCATION: (1)..(57)

<400> SEQUENCE: 30
atggaattcg gcctgagctg ggtgttcctg gtggccatcc tgaagggcgt gcagtgcgag      60
gtgcagctgg tcgagagcgg cggagccctg gtgcagcccg gcagaagcct gagactgagc     120
tgccggacca gcggcctgaa cttcggcgac taccccatca ctgggtgcg gcaggctcca     180 gggaaaggac tcgaatgggt gggcttcatc aagagcaaga gctacggcgt gaccaccgag     240
ttcgccgcca gcgtggaggg ccggttcacc atcagccggg acgacagccg gggcattgcc     300
tacctgcaga tgaacagcct gaaaaccgag gacaccgccg tgtactactg caccagcagc     360
agcggctttc tgtactactt cgactactgg ggacagggca cctggtgac cgtgagcagc     420 gccagcacca agggcccag cgtgttcccc ctggccccca gcagcaagag taccagcgga     480
ggcactgctg ccctcggatg cctggtgaag gactacttcc ccgagcccgt gaccgtgtcc     540
tggaactctg gcgccctgac ctccggcgtg cacaccttcc ccgccgtgct ccagtctagt     600
```

-continued

```
ggcctgtata gcctgagcag cgtggtgaca gtccctagca gttccctggg aacccagacc    660
tacatctgca acgtgaacca caagcccagc aacaccaagg tggacaagaa ggtggagccc    720
aagagctgcg acaagaccca cacctgcccc ccctgccctg ccctgagct gctgggcgga    780
ccctccgtgt tcctgttccc ccccaagccc aaggacaccc tgatgatcag ccggaccccc    840
gaggtgacct gcgtggtggt ggatgtgagt catgaggatc ctgaggtgaa gttcaattgg    900
tacgtggacg gcgtggaggt gcacaacgcc aagaccaagc ccgggagga acagtacaac    960
agcacctacc gggtggtgtc cgtgctgacc gtgctgcacc aggactggct gaacggcaaa   1020
gaatacaagt gcaaggtgtc caacaaggcc ctgcctgccc ccatcgagaa aaccatcagc   1080
aaggccaagg gccagcctag agaacccag gtgtacacac tgcctccatc ccgggacgag   1140
ctgaccaaga accaggtgtc cctgacctgt ctggtgaagg gcttctaccc cagcgatatc   1200
gccgtggagt gggagagcaa cggccagccc gagaacaact acaagaccac ccccctgtg   1260
ctggacagcg acggcagctt cttcctgtac agcaagctga ccgtggacaa gagccggtgg   1320
cagcagggca acgtgttcag ctgcagcgtg atgcacgagg ccctgcacaa ccactacacc   1380
cagaagagcc tgagcctgtc ccccggcaag tga                                1413
```

<210> SEQ ID NO 31
<211> LENGTH: 470
<212> TYPE: PRT
<213> ORGANISM: Homo sapiens
<220> FEATURE:
<221> NAME/KEY: SIGNAL
<222> LOCATION: (1)..(19)

<400> SEQUENCE: 31

```
Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Ala Leu Val Gln
                20                  25                  30

Pro Gly Arg Ser Leu Arg Leu Ser Cys Arg Thr Ser Gly Leu Asn Phe
            35                  40                  45

Gly Asp Tyr Pro Ile Asn Trp Val Arg Gln Ala Pro Gly Lys Gly Leu
        50                  55                  60

Glu Trp Val Gly Phe Ile Lys Ser Lys Ser Tyr Gly Val Thr Thr Glu
65                  70                  75                  80

Phe Ala Ala Ser Val Glu Gly Arg Phe Thr Ile Ser Arg Asp Asp Ser
                85                  90                  95

Arg Gly Ile Ala Tyr Leu Gln Met Asn Ser Leu Lys Thr Glu Asp Thr
            100                 105                 110

Ala Val Tyr Tyr Cys Thr Ser Ser Gly Phe Leu Tyr Tyr Phe Asp
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
```

```
             210                 215                 220
Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 32
<211> LENGTH: 723
<212> TYPE: DNA
<213> ORGANISM: Homo sapiens
<220> FEATURE:
<221> NAME/KEY: sig_peptide
<222> LOCATION: (1)..(60)

<400> SEQUENCE: 32
atggtgctgc agacccaggt gttcatcagc ctgctgctgt ggatcagcgg cgcctacggc    60
gacatcgtga tgacccagag ccccgacagc ctggccgtga gcctgggcga gcgggccacc   120
atcaactgca gagcagcca gagcgtgctg tacaccagca caacaagaa ctacctgggc   180 tggtatcagc agaagcccgg ccagcccccc aacctgctga tctactgggc cagcacccgg   240
gagagcggcg tgcccgaccg gtttagcggc agcggctccg gcaccgactt cacccctgac   300
atcaacagcg tgcaggccga ggacgtggcc gtgtactact gccagcagta cttcatgacc   360
cccatcaccc tcggcagggg caccggctg gaaatcaagc gtacggtggc cgcccctcc   420 gtgttcatct ccccccccag cgacgagcag ctgaagagcg gcaccgccag cgtggtgtgc   480
ctgctgaaca acttctaccc ccgggaggcc aaggtgcagt ggaaggtgga caacgccctg   540
cagagcggca acagccagga aagcgtcacc gagcaggaca gcaaggactc cacctacagc   600
```

-continued ctgagcagca cccctgaccct gagcaaggcc gactacgaga agcacaaggt gtacgcctgc 660
gaggtgaccc accagggcct gtccagcccc gtgaccaaga gcttcaaccg gggcgagtgc 720
tga 723

<210> SEQ ID NO 33
<211> LENGTH: 240
<212> TYPE: PRT
<213> ORGANISM: Homo sapiens
<220> FEATURE:
<221> NAME/KEY: SIGNAL
<222> LOCATION: (1)..(20)

<400> SEQUENCE: 33

Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Val Leu Tyr Thr Ser Asn Asn Lys Asn Tyr Leu Gly Trp Tyr Gln Gln
    50                  55                  60

Lys Pro Gly Gln Pro Pro Asn Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Asn Ser Val Gln Ala Glu Asp Val Ala Val Tyr
            100                 105                 110

Tyr Cys Gln Gln Tyr Phe Met Thr Pro Ile Thr Phe Gly Gln Gly Thr
        115                 120                 125

Arg Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 34
<211> LENGTH: 723
<212> TYPE: DNA
<213> ORGANISM: Homo sapiens
<220> FEATURE:
<221> NAME/KEY: sig_peptide
<222> LOCATION: (1)..(60)

<400> SEQUENCE: 34
atggtgctgc agacccaggt gttcatcagc ctgctgctgt ggatcagcgg cgcctacggc 60
gacatcgtga tgacccagag ccccgacagc ctggccgtga gcctgggcga gcgggccacc 120
atcaactgca agagcagcca gagcgtgctg tacagcagca acaacgagaa ctacctggcc 180

```
tggtatcagc agaagcccgg ccagccccc aagctgctga tctactgggc agcacccgg    240 gagagcggcg tgcccgaccg gtttagcggc agcggctccg gcaccgactt caccctgacc    300
atcaacagcg tgcaggccga ggacgtggcc gtgtactact gccagcagta cttcatgacc    360
cccatcacct tcggcagggg cacccggctg gaaatcaagc gtacggtggc cgccccctcc    420
gtgttcatct ccccccag cgacgagcag ctgaagagcg gcaccgccag cgtggtgtgc    480
ctgctgaaca acttctaccc ccggggaggcc aaggtgcagt ggaaggtgga caacgccctg    540
cagagcggca acagccagga aagcgtcacc gagcaggaca gcaaggactc cacctacagc    600
ctgagcagca ccctgaccct gagcaaggcc gactacgaga agcacaaggt gtacgcctgc    660
gaggtgaccc ccagggcct gtccagcccc gtgaccaaga gcttcaaccg gggcgagtgc    720
tga                                                                  723
```

<210> SEQ ID NO 35
<211> LENGTH: 240
<212> TYPE: PRT
<213> ORGANISM: Homo sapiens
<220> FEATURE:
<221> NAME/KEY: SIGNAL
<222> LOCATION: (1)..(20)

<400> SEQUENCE: 35

```
Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Val Leu Tyr Ser Ser Asn Asn Glu Asn Tyr Leu Ala Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Asn Ser Val Gln Ala Glu Asp Val Ala Val Tyr
            100                 105                 110

Tyr Cys Gln Gln Tyr Phe Met Thr Pro Ile Thr Phe Gly Gln Gly Thr
        115                 120                 125

Arg Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 36
<211> LENGTH: 723
<212> TYPE: DNA

```
<213> ORGANISM: Homo sapiens
<220> FEATURE:
<221> NAME/KEY: sig_peptide
<222> LOCATION: (1)..(60)

<400> SEQUENCE: 36
atggtgctgc agacccaggt gttcatcagc ctgctgctgt ggatcagcgg cgcctacggc    60
gacatcgtga tgacccagag ccccgacgcc ctggccgtga gcctgggcga gcgggccacc   120
atcaactgca gagcagcca gagcctgctg tacagcagca caacaagaa ctacctggcc    180
tggtatcaga aaaagcccgg ccagccccc aagctgctga tctactggc cagcaccgg     240
gagagcggcg tgcccgaccg gtttagcggc agcggctccg gcaccgagtt caccctgacc   300
atcaacagcg tgcaggccga ggacgtggcc gtgtactact gccagcagta cttcatgacc   360
cccatcaccct tcggccaggg cacccggctg gaaatcaagc gtacggtggc cgcccctcc    420
gtgttcatct ccccccag cgacgagcag ctgaagagcg gcaccgccag cgtggtgtgc     480
ctgctgaaca cttctaccc ccgggaggcc aaggtgcagt ggaaggtgga caacgccctg   540
cagagcggca cagccagga aagcgtcacc gagcaggaca gcaaggactc cacctacagc   600
ctgagcagca ccctgaccct gagcaaggcc gactacgaga agcacaaggt gtacgcctgc   660
gaggtgaccc ccagggcct gtccagcccc gtgaccaaga gcttcaaccg ggcgagtgc    720
tga                                                                 723

<210> SEQ ID NO 37
<211> LENGTH: 240
<212> TYPE: PRT
<213> ORGANISM: Homo sapiens
<220> FEATURE:
<221> NAME/KEY: SIGNAL
<222> LOCATION: (1)..(20)

<400> SEQUENCE: 37

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ala Leu Ala
                20                  25                  30

Val Ser Leu Gly Glu Arg Ala Thr Ile Asn Cys Lys Ser Ser Gln Ser
            35                  40                  45

Leu Leu Tyr Ser Ser Asn Asn Lys Asn Tyr Leu Ala Trp Tyr Gln Lys
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Glu
                85                  90                  95

Phe Thr Leu Thr Ile Asn Ser Val Gln Ala Glu Asp Val Ala Val Tyr
            100                 105                 110

Tyr Cys Gln Gln Tyr Phe Met Thr Pro Ile Thr Phe Gly Gln Gly Thr
        115                 120                 125

Arg Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190
```

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240

<210> SEQ ID NO 38
<211> LENGTH: 812
<212> TYPE: DNA
<213> ORGANISM: artificial sequence
<220> FEATURE:
<223> OTHER INFORMATION: synthetic

<400> SEQUENCE: 38

```
ggcccaggcg gccgagctcg tgatgaccca gtctcctgac tccctggctg tgtccctggg      60
cgagagggcc accatcaact gcaagtccag ccagagtgtt ctatacacct ccaacaataa     120
gaactactta ggttggtacc agcagaaacc agggcagccg cctaatttac tcatttattg     180
ggcatctacc cgggaatccg ggtccctga ccgattcagt ggcagcgggt ctgggacaga      240
tttcactctc accatcaaca gcgtgcaggc tgaggatgtg gcagtttatt actgccagca     300
gtattttatg actcccatca ccttcggcca agggacacga ctggagatta aggtggttc     360 ctctagatct tcctcctctg gtggcggtgg ctcgggcgt ggtggggagg tgcagctggt      420
ggagtctggg ggggcttgg tacagccagg gcggtccctg agactctcct gtagaacctc      480
tggactcaat tttggagatt atcctataaa ctgggtccgc caggctccag ggaaggggct     540
ggagtgggta gggttcatca aaagcaagtc ttatggtgtg caacagaat cgccgcgtc      600 tgtggagggc agattcacca tctcgaggga tgattccaga ggcatcgcct atctgcagat     660
gaacagcctg aaaaccgagg acacagccgt ctattactgt acgtccagta gtggtttttt     720
gtactacttt gactactggg gccagggaac cctggtcacc gtctcctcag cctccaccaa     780
gggcccatcg gtcactagtg gccaggccgg cc                                   812
```

<210> SEQ ID NO 39
<211> LENGTH: 812
<212> TYPE: DNA
<213> ORGANISM: artificial sequence
<220> FEATURE:
<223> OTHER INFORMATION: synthetic

<400> SEQUENCE: 39

```
ggcccaggcg gccgagctcg tgatgactca gtctccagac tccctggctg tgtctctggg      60
cgagagggcc accatcaact gcaagtccag ccagagtgtt ttatacagct ccaacaatga     120
gaactactta gcttggtacc agcagaaacc aggacagcct cctaaactgc tcatttactg     180
ggcatctacc cgggaatccg ggtccctga ccgattcagt ggcagcgggt ctgggacaga      240
tttcactctc accatcaaca gcgtgcaggc tgaggatgtg gcagtttatt actgccagca     300
gtattttatg actcccatca ccttcggcca agggacacga ctggagatta aggtggttc     360 ctctagatct tcctcctctg gtggcggtgg ctcgggcgt ggtggggagg tgcagctgtt      420
ggagtctggg ggggcttgg tacagccagg gcggtccctg agactctcct gtagaacctc      480
tggactcaat tttggagatt atcctataaa ctgggtccgc caggctccag ggaaggggct     540
ggagtgggta gggttcatca aaagcaagtc ttatggtgtg caacagaat cgccgcgtc      600 tgtggagggc agattcacca tctcaaggga tgattccaga ggcatcgcct atctgcagat     660
gaacagcctg aaaaccgagg acacagccgt ctattactgt acgtccagta gtggtttttt     720
```

```
gtactacttt gactactggg gccagggaac cctggtcacc gtctcctcag cttccaccaa    780
gggcccatca gtcactagtg gccaggccgg cc                                  812
```

<210> SEQ ID NO 40
<211> LENGTH: 812
<212> TYPE: DNA
<213> ORGANISM: artificial sequence
<220> FEATURE:
<223> OTHER INFORMATION: synthetic

<400> SEQUENCE: 40

```
ggcccaggcg gccgagcgcg tgatgacaca gtctccagac gccctggctg tgtctctggg     60
cgagagggcc accatcaact gcaagtccag ccagagtctt ttatacagct ccaataataa    120
gaactactta gcttggtatc agaagaaacc aggacagcct cctaagctgc tcatttactg    180
ggcatctacc cgggaatccg ggtccctga ccgattcagt ggcagcgggt ctgggacaga     240
gttcactctc accatcaaca gcgtgcaggc tgaggatgtg gcagtttatt actgccagca    300
gtattttatg actcccatca ccttcggcca agggaccaag ctggagatca aggtggttc     360 ctctagatct tcctcctctg gtggcggtgg ctcgggcgt ggtgggcagg tgcagctgca     420
ggagtcgggg ggggccttgg tacagccagg gcggtccctg agactctcct gtagaacctc    480
tggactcaat tttggagatt atcctataaa ctgggtccgc caggctccag gaaggggct     540 ggagtgggta gggttcatca aaagcaagtc ttatggtgtg acaacagaat cgccgcgtc     600 tgtggagggc agattcacca tctcaaggga tgattccaga ggcatcgcct atctgcagat    660
gaacagcctg aaaaccgagg acacagccgt ctattactgt acgtccagta gtggttttt     720 gtactacttt gactactggg gccagggaac cctggtcacc gtctcctcag cttccaccaa    780
gggcccatcg gtcactagtg gccaggccgg cc                                  812
```

<210> SEQ ID NO 41
<211> LENGTH: 10348
<212> TYPE: DNA
<213> ORGANISM: artificial sequence
<220> FEATURE:
<223> OTHER INFORMATION: cloning vector

<400> SEQUENCE: 41

```
ggtaccatgg agacagacac actcctgcta tgggtactgc tgctctgggt tccaggttcc     60
actggtgacg cggatccggc ccaggcggcc ttaattaaag gtttaaacgg ccaggccggc    120
cgcaagcttg agcccagagt gcccataaca cagaacccct gtcctccact caaagagtgt    180
cccccatgcg cagctccaga cctcttgggt ggaccatccg tcttcatctt ccctccaaag    240
atcaaggatg tactcatgat ctccctgagc cccatggtca catgtgtggt ggtggatgtg    300
agcgaggatg acccagacgt ccagatcagc tggtttgtga acaacgtgga agtacacaca    360
gctcagacac aaacccatag agaggattac aacagtactc tccgggtggt cagtgccctc    420
cccatccagc accaggactg gatgagtggc aaggagttca aatgcaaggt caacaacaga    480
gccctcccat cccccatcga gaaaaccatc tcaaaaccca gagggccagt aagagctcca    540
caggtatatg tcttgcctcc accagcagaa gagatgacta gaaagagtt cagtctgacc    600 tgcatgatca caggcttctt acctgccgaa attgctgtgg actggaccag caatgggcgt    660
acagagcaaa actacaagaa caccgcaaca gtcctggact ctgatggttc ttacttcatg    720
tacagcaagc tcagagtaca aaagagcact tgggaaagag aagtcttt cgcctgctca     780 gtggtccacg agggtctgca caatcacctt acgactaaga ccatctcccg gtctctgggt    840
```

```
aaatgactcg aggcccgaac aaaaactcat ctcagaagag gatctgaata gcgccgtcga    900
ccatcatcat catcatcatt gagtttaacg atccagacat gataagatac attgatgagt    960
ttggacaaac cacaactaga atgcagtgaa aaaaatgctt tatttgtgaa atttgtgatg   1020
ctattgcttt atttgtaacc attataagct gcaataaaca agttaacaac aacaattgca   1080
ttcattttat gtttcaggtt caggggggagg tggggaggtt ttttaaagca agtaaaacct   1140
ctacaaatgt ggtatggctg attatgatcc ggctgcctcg cgcgtttcgg tgatgacggt   1200
gaaaacctct gacacatgca gctcccggag acggtcacag cttgtctgta agcggatgcc   1260
gggagcagac aagcccgtca gggcgcgtca gcgggtgttg gcgggtgtcg ggcgcagcc    1320
atgaggtcga ctctagagga tcgatccccg ccgccggacg aactaaacct gactacggca   1380
tctctgcccc ttcttcgcgg ggcagtgcat gtaatcccett cagttggttg gtacaacttg   1440
ccaactgggc cctgttccac atgtgacacg ggggggggacc aaacacaaag gggttctctg   1500
actgtagttg acatccttat aaatggatgt gcacatttgc caacactgag tggctttcat   1560
cctggagcag actttgcagt ctgtggactg caacacaaca ttgcctttat gtgtaactct   1620
tggctgaagc tcttacacca atgctggggg acatgtacct cccaggggcc caggaagact   1680
acgggaggct acaccaacgt caatcagagg ggcctgtgta gctaccgata agcggaccct   1740
caagagggca ttagcaatag tgtttataag gcccccttgt taaccctaaa cgggtagcat   1800
atgcttcccg ggtagtagta tatactatcc agactaaccc taattcaata gcatatgtta   1860
cccaacggga agcatatgct atcgaattag ggttagtaaa agggtcctaa ggaacagcga   1920
tatctcccac cccatgagct gtcacggttt tatttacatg gggtcaggat tccacgaggg   1980
tagtgaacca ttttagtcac aagggcagtg gctgaagatc aaggagcggg cagtgaactc   2040
tcctgaatct tcgcctgctt cttcattctc cttcgtttag ctaatagaat aactgctgag   2100
ttgtgaacag taaggtgtat gtgaggtgct cgaaaacaag gtttcaggtg acgcccccag   2160
aataaaattt ggacgggggg ttcagtggtg gcattgtgct atgacaccaa tataaccctc   2220
acaaacccct tgggcaataa atactagtgt aggaatgaaa cattctgaat atctttaaca   2280
atagaaatcc atggggtggg gacaagccgt aaagactgga tgtccatctc acacgaattt   2340
atggctatgg gcaacacata atcctagtgc aatatgatac tggggttatt aagatgtgtc   2400
ccagcaggg accaagacag gtgaaccatg ttgttacact ctatttgtaa caaggggaaa   2460
gagagtggac gccgacagca gcggactcca ctggttgtct ctaacacccc cgaaaattaa   2520
acggggctcc acgccaatgg ggcccataaa caaagacaag tggccactct tttttttgaa   2580
attgtggagt gggggcacgc gtcagccccc acacgccgcc ctgcggtttt ggactgtaaa   2640
ataagggtgt aataacttgg ctgattgtaa ccccgctaac cactgcggtc aaaccacttg   2700
cccacaaaac cactaatggc accccggggga ataccctgcat aagtaggtgg gcgggccaag   2760
ataggggcgc gattgctgcg atctggagga caaattacac acacttgcgc ctgagcgcca   2820
agcacagggt tgttggtcct catattcacg aggtcgctga gagcacggtg ggctaatgtt   2880
gccatgggta gcatatacta cccaaatatc tggatagcat atgctatcct aatctatatc   2940
tgggtagcat aggctatcct aatctatatc tgggtagcat atgctatcct aatctatatc   3000
tgggtagtat atgctatcct aatttatatc tgggtagcat aggctatcct aatctatatc   3060
tgggtagcat atgctatcct aatctatatc tgggtagtat atgctatcct aatctgtatc   3120
cgggtagcat atgctatcct aatagagatt agggtagtat atgctatcct aatttatatc   3180
tgggtagcat atactaccca aatatctgga tagcatatgc tatcctaatc tatatctggg   3240
```

```
tagcatatgc tatcctaatc tatatctggg tagcataggc tcctaatc tatatctggg    3300 tagcatatgc tatcctaatc tatatctggg tagtatatgc tatcctaatt tatatctggg  3360
tagcataggc tatcctaatc tatatctggg tagcatatgc tatcctaatc tatatctggg  3420
tagtatatgc tatcctaatc tgtatccggg tagcatatgc tatcctcatg catatacagt  3480
cagcatatga tacccagtag tagagtggga gtgctatcct ttgcatatgc cgccacctcc  3540
caagggggcg tgaattttcg ctgcttgtcc ttttcctgca tgctggttgc tcccattctt  3600
aggtgaattt aaggaggcca ggctaaagcc gtcgcatgtc tgattgctca ccaggtaaat  3660
gtcgctaatg ttttccaacg cgagaaggtg ttgagcgcgg agctgagtga cgtgacaaca  3720
tgggtatgcc caattgcccc atgttgggag gacgaaaatg gtgacaagac agatggccag  3780
aaatacacca acagcacgca tgatgtctac tggggattta ttctttagtg cggggggaata 3840 cacggctttt aatacgattg agggcgtctc ctaacaagtt acatcactcc tgcccttcct  3900
caccctcatc tccatcacct ccttcatctc cgtcatctcc gtcatcaccc tccgcggcag  3960 cccctccac cataggtgga accaggggag gcaaatctac tccatcgtca agctgcaca   4020 cagtcaccct gatattgcag gtaggagcgg gctttgtcat aacaaggtcc ttaatcgcat  4080
ccttcaaaac ctcagcaaat atatgagttt gtaaaagac catgaaataa cagacaatgg   4140
actcccttag cgggccaggt tgtgggccgg tccaggggc cattccaaag gggagacgac   4200
tcaatggtgt aagacgacat tgtggaatag caagggcagt tcctcgcctt aggttgtaaa  4260
gggaggtctt actacctcca tatacgaaca caccggcgac ccaagttcct tcgtcggtag  4320
tcctttctac gtgactccta gccaggagag ctcttaaacc ttctgcaatg ttctcaaatt  4380
tcgggttgga acctccttga ccacgatgct ttccaaacca ccctccttt ttgcgcctgc  4440 ctccatcacc ctgaccccgg ggtccagtgc ttgggccttc tcctgggtca tctgcggggc  4500
cctgctctat cgctcccggg ggcacgtcag gctcaccatc tgggccacct tcttggtggt  4560
attcaaaata atcggcttcc cctacagggt ggaaaaatgg ccttctacct ggagggggcc  4620
tgcgcggtgg agacccggat gatgatgact gactactggg actcctgggc ctcttttctc  4680
cacgtccacg acctctcccc ctggctcttt cacgacttcc cccctggct ctttcacgtc    4740 ctctaccccg gcggcctcca ctacctcctc gaccccggcc tccactacct cctcgacccc  4800
ggcctccact gcctcctcga ccccggcctc cacctcctgc tcctgcccct cctgctcctg  4860 ccctcctcc tgctcctgcc cctcctgccc ctcctgctcc tgcccctcct gcccctcctg   4920
ctcctgcccc tcctgcccct cctgctctg cccctctgc cctctcctct gctcctgccc   4980
ctcctgcccc tcctcctgct cctgcccctc ctgcccctcc tgctcctgcc cctcctgccc  5040
ctcctgctcc tgcccctcct gcccctcctg ctcctgcccc tcctgctcct gcccctcctg  5100
ctcctgcccc tcctgctcct gcccctcctg cccctcctgc cctcctcct gctcctgccc   5160 ctcctgctcc tgcccctcct gcccctctg cctgcccct cctctgctc                5220 ctgcccctcc tgcccctcct gctcctgcc cctcctgcc cctcctcctg               5280 ctcctgcccc tcctcctgct cctgcccctc ctgcccctcc tgcccctcct cctgctcctg  5340
cccctcctgc cctcctcct gtcctgcccc tcctcctgc cctgcccct ctgcccctc     5400 ctgcccctcc tcctgctcct gcccctcctg ctcctgcccc tcctgccct cctgctcctg  5460 ctcctgcccc tcctcctgct cctgcccctc ctgctcctgc tgcccctcct gtcctgccc  5520 ctcccgctcc tgcccctgct cctgttccac cgtgggtccc ttgcagcca atgcaacttg   5580 gacgtttttg gggtctccgg acaccatctc tatgtcttgg ccctgatcct gagccgcccg  5640
```

```
gggctcctgg tcttccgcct cctcgtcctc gtcctcttcc ccgtcctcgt ccatggttat   5700
caccccctct tctttgaggt ccactgccgc cggagccttc tggtccagat gtgtctccct   5760
tctctcctag gccatttcca ggtcctgtac ctggcccctc gtcagacatg attcacacta   5820
aaagagatca atagacatct ttattagacg acgctcagtg aatacaggga gtgcagactc   5880 ctgcccctc caacagcccc cccaccctca tccccttcat ggtcgctgtc agacagatcc    5940
aggtctgaaa attccccatc ctccgaacca tcctcgtcct catcaccaat tactcgcagc   6000
ccggaaaact cccgctgaac atcctcaaga tttgcgtcct gagcctcaag ccaggcctca   6060
aattcctcgt cccccttttt gctggacggt agggatgggg attctcggga cccctcctct   6120
tcctcttcaa ggtcaccaga cagagatgct actggggcaa cggaagaaaa gctgggtgcg   6180
gcctgtgagg atcagcttat cgatgataag ctgtcaaaca tgagaattct tgaagacgaa   6240
agggcctcgt gatacgccta tttttatagg ttaatgtcat gataataatg gtttcttaga   6300
cgtcaggtgg cacttttcgg ggaaatgtgc gcggaacccc tatttgttta tttttctaaa   6360
tacattcaaa tatgtatccg ctcatgagac aataaccctg ataaatgctt caataatatt   6420
gaaaaaggaa gagtatgagt attcaacatt tccgtgtcgc ccttattccc ttttttgcgg   6480
cattttgcct tcctgttttt gctcacccag aaacgctggt gaaagtaaaa gatgctgaag   6540
atcagttggg tgcacgagtg ggttacatcg aactggatct caacagcggt aagatccttg   6600
agagttttcg ccccgaagaa cgttttccaa tgatgagcac ttttaaagtt ctgctatgtg   6660
gcgcggtatt atcccgtgtt gacgccgggc aagagcaact cggtcgccgc atacactatt   6720
ctcagaatga cttggttgag tactcaccag tcacagaaaa gcatcttacg gatggcatga   6780
cagtaagaga attatgcagt gctgccataa ccatgagtga taacactgcg gccaacttac   6840
ttctgacaac gatcggagga ccgaaggagc taaccgcttt tttgcacaac atgggggatc   6900
atgtaactcg ccttgatcgt tgggaaccgg agctgaatga agccatacca aacgacgagc   6960
gtgacaccac gatgcctgca gcaatggcaa caacgttgcg caaactatta actggcgaac   7020
tacttactct agcttcccgg caacaattaa tagactggat ggaggcggat aaagttgcag   7080
gaccacttct gcgctcggcc cttccggctg gctggtttat tgctgataaa tctggagccg   7140
gtgagcgtgg gtctcgcggt atcattgcag cactggggcc agatggtaag ccctcccgta   7200
tcgtagttat ctacacgacg gggagtcagg caactatgga tgaacgaaat agacagatcg   7260
ctgagatagg tgcctcactg attaagcatt ggtaactgtc agaccaagtt tactcatata   7320
tactttagat tgatttaaaa cttcattttt aatttaaaag gatctaggtg aagatccttt   7380
ttgataatct catgaccaaa atcccttaac gtgagttttc gttccactga gcgtcagacc   7440
ccgtagaaaa gatcaaagga tcttcttgag atcctttttt tctgcgcgta atctgctgct   7500
tgcaaacaaa aaaaccaccg ctaccagcgg tggtttgttt gccggatcaa gagctaccaa   7560 ctcttttcc gaaggtaact ggcttcagca gagcgcagat accaaatact gtccttctag    7620
tgtagccgta gttaggccac cacttcaaga actctgtagc accgcctaca tacctcgctc   7680
tgctaatcct gttaccagtg gctgctgcca gtggcgataa gtcgtgtctt accgggttgg   7740
actcaagacg atagttaccg gataaggcgc agcggtcggg ctgaacgggg gttcgtgca    7800 cacagcccag cttggagcga acgacctaca ccgaactgag atacctacag cgtgagctat   7860
gagaaagcgc cacgcttccc gaagggagaa aggcggacag gtatccggta agcggcaggg   7920
tcggaacagg agagcgcacg agggagcttc caggggggaaa cgcctggtat ctttatagtc   7980
ctgtcgggtt tcgccacctc tgacttgagc gtcgattttt gtgatgctcg tcagggggc    8040
```

```
ggagcctatg gaaaaacgcc agcaacgcgg ccttttacg gttcctggcc ttttgctgcg    8100
ccgcgtgcgg ctgctggaga tggcggacgc gatggatatg ttctgccaag ggttggtttg    8160
cgcattcaca gttctccgca agaattgatt ggctccaatt cttggagtgg tgaatccgtt    8220
agcgaggcca tccagcctcg cgtcgaacta gatgatccgc tgtggaatgt gtgtcagtta    8280
gggtgtggaa agtccccagg ctccccagca ggcagaagta tgcaaagcat gcatctcaat    8340
tagtcagcaa ccaggtgtgg aaagtcccca ggctcccag caggcagaag tatgcaaagc    8400
atgcatctca attagtcagc aaccatagtc ccgcccctaa ctccgcccat cccgccccta    8460
actccgccca gttccgccca ttctccgccc catggctgac taatttttt tatttatgca    8520
gaggccgagg ccgcggcctc tgagctattc cagaagtagt gaggaggctt ttttggaggg    8580
tgaccgccac gaggtgccgc caccatcccc tgacccacgc ccctgacccc tcacaaggag    8640
acgaccttcc atgaccgagt acaagcccac ggtgcgcctc gccacccgcg acgacgtccc    8700
ccgggccgta cgcaccctcg ccgccgcgtt cgccgactac cccgccacgc gccacaccgt    8760
cgaccccgac cgccacatcg aacgcgtcac cgagctgcaa gaactcttcc tcacgcgcgt    8820
cgggctcgac atcggcaagg tgtgggtcgc ggacgacggc gccgcggtgg cggtctggac    8880
cacgccggag agcgtcgaag cggggggcggt gttcgccgag atcggcccgc gcatggccga    8940
gttgagcggt tcccgctgg ccgcgcagca acagatggaa ggcctcctgg cgccgcaccg    9000
gcccaaggag cccgcgtggt tcctggccac cgtcggcgtc tcgcccgacc accagggcaa    9060
gggtctgggc agcgccgtcg tgctccccgg agtggaggcg gccgagcgcg ccggggtgcc    9120
cgccttcctg gagacctccg cgccccgcaa cctcccttc tacgagcggc tcggcttcac    9180
cgtcaccgcc gacgtcgagt gcccgaagga ccgcgcgacc tggtgcatga cccgcaagcc    9240
cggtgcctga cgcccgcccc acgacccgca gcgcccgacc gaaaggagcg cacgacccgg    9300
tccgacggcg gcccacgggt cccagggggg tcgacctcga aacttgttta ttgcagctta    9360
taatggttac aaataaagca atagcatcac aaatttcaca aataaagcat ttttttcact    9420
gcattctagt tgtggtttgt ccaaactcat caatgtatct tatcatgtct ggatcgatcc    9480
gaacccttc ctcgaccaat tctcatgttt gacagcttat catcgcagat ccgggcaacg    9540
ttgttgcatt gctgcaggcg cagaactggt aggtatggaa gatctataca ttgaatcaat    9600
attggcaatt agccatatta gtcattggtt atatagcata aatcaatatt ggctattggc    9660
cattgcatac gttgtatcta tatcataata tgtacattta tattggctca tgtccaatat    9720
gaccgccatg ttgacattga ttattgacta gttattaata gtaatcaatt acggggtcat    9780
tagttcatag cccatatatg gagttccgcg ttacataact tacggtaaat ggcccgcctg    9840
gctgaccgcc caacgacccc cgcccattga cgtcaataat gacgtatgtt cccatagtaa    9900
cgccaatagg gactttccat tgacgtcaat gggtggagta tttacggtaa actgcccact    9960
tggcagtaca tcaagtgtat catatgccaa gtccgccccc tattgacgtc aatgacggta   10020
aatggcccgc ctggcattat gcccagtaca tgaccttacg ggactttcct acttggcagt   10080
acatctacgt attagtcatc gctattacca tggtgatgcg gttttggcag tacaccaatg   10140
ggcgtggata gcggtttgac tcacggggat ttccaagtct ccaccccatt gacgtcaatg   10200
ggagtttgtt ttggcaccaa aatcaacggg actttccaaa atgtcgtaat aacccccgccc   10260
cgttgacgca aatgggcggt aggcgtgtac ggtgggaggt ctatataagc agagctcgtt   10320
tagtgaaccg tcagatctct agaagctg                                      10348
```

<210> SEQ ID NO 42
<211> LENGTH: 1608
<212> TYPE: DNA
<213> ORGANISM: artificial sequence
<220> FEATURE:
<223> OTHER INFORMATION: synthetic
<220> FEATURE:
<221> NAME/KEY: sig_peptide
<222> LOCATION: (1)..(60)

<400> SEQUENCE: 42

```
atggagacag acacactcct gctatgggta ctgctgctct gggttccagg ttccactggt      60
gacgcggatc cggcccaggc ggccgagctc gtgatgaccc agtctcctga ctccctggct     120
gtgtccctgg gcgagagggc caccatcaac tgcaagtcca gccagagtgt tctatacacc     180
tccaacaata gaactactt aggttggtac cagcagaaac cagggcagcc gcctaattta      240
ctcatttatt gggcatctac ccgggaatcc ggggtccctg accgattcag tggcagcggg     300
tctgggacag atttcactct caccatcaac agcgtgcagg ctgaggatgt ggcagtttat     360
tactgccagc agtattttat gactcccatc accttcggcc aagggacacg actggagatt     420
aaaggtggtt cctctagatc ttcctcctct ggtggcggtg gctcgggcgg tggtggggag     480
gtgcagctgg tggagtctgg ggggccttg gtacagccag gcggtccct gagactctcc       540
tgtagaacct ctggactcaa ttttggagat tatcctataa actgggtccg ccaggctcca     600
gggaagggc tggagtgggt agggttcatc aaaagcaagt cttatggtgt gacaacagaa      660
ttcgccgcgt ctgtgagggg cagattcacc atctcgaggg atgattccag aggcatcgcc     720
tatctgcaga tgaacagcct gaaaaccgag gacacagccg tctattactg tacgtccagt     780
agtggttttt tgtactactt tgactactgg ggccagggaa ccctggtcac cgtctcctca     840
gcctccacca agggcccatc ggtcactagt ggccaggccg ccgcaagct tgagcccaga     900
gtgcccataa cacagaaccc ctgtcctcca ctcaaagagt gtccccatg cgcagctcca     960
gacctcttgg gtggaccatc cgtcttcatc ttccctccaa agatcaagga tgtactcatg    1020
atctccctga gccccatggt cacatgtgtg gtggtggatg tgagcgagga tgacccagac    1080
gtccagatca gctggtttgt gaacaacgtg aagtacaca cagctcagac acaaaccat      1140
agagaggatt acaacagtac tctccgggtg gtcagtgccc tccccatcca gcaccaggac    1200
tggatgagtg gcaaggagtt caaatgcaag gtcaacaaca gagccctccc atcccccatc    1260
gagaaaacca tctcaaaacc cagagggcca gtaagagctc cacaggtata tgtcttgcct    1320
ccaccagcag aagagatgac taagaaagag ttcagtctga cctgcatgat cacaggcttc    1380
ttacctgccg aaattgctgt ggactggacc agcaatgggc gtacagagca aaactacaag    1440
aacaccgcaa cagtcctgga ctctgatggt tcttacttca tgtacagcaa gctcagagta    1500
caaaagagca cttgggaaag aggaagtctt ttcgcctgct cagtggtcca cgagggtctg    1560
cacaatcacc ttacgactaa gaccatctcc cggtctctgg gtaaatga                 1608
```

<210> SEQ ID NO 43
<211> LENGTH: 535
<212> TYPE: PRT
<213> ORGANISM: artificial sequence
<220> FEATURE:
<223> OTHER INFORMATION: synthetic
<220> FEATURE:
<221> NAME/KEY: SIGNAL
<222> LOCATION: (1)..(20)

<400> SEQUENCE: 43

Met Glu Thr Asp Thr Leu Leu Leu Trp Val Leu Leu Leu Trp Val Pro

-continued

```
1               5                   10                  15
Gly Ser Thr Gly Asp Ala Asp Pro Ala Gln Ala Glu Leu Val Met
                20                  25                  30

Thr Gln Ser Pro Asp Ser Leu Ala Val Ser Leu Gly Glu Arg Ala Thr
                35                  40                  45

Ile Asn Cys Lys Ser Ser Gln Ser Val Leu Tyr Thr Ser Asn Asn Lys
    50                  55                  60

Asn Tyr Leu Gly Trp Tyr Gln Gln Lys Pro Gly Gln Pro Pro Asn Leu
65                  70                  75                  80

Leu Ile Tyr Trp Ala Ser Thr Arg Glu Ser Gly Val Pro Asp Arg Phe
                85                  90                  95

Ser Gly Ser Gly Ser Gly Thr Asp Phe Thr Leu Thr Ile Asn Ser Val
                100                 105                 110

Gln Ala Glu Asp Val Ala Val Tyr Tyr Cys Gln Gln Tyr Phe Met Thr
                115                 120                 125

Pro Ile Thr Phe Gly Gln Gly Thr Arg Leu Glu Ile Lys Gly Gly Ser
                130                 135                 140

Ser Arg Ser Ser Ser Gly Gly Gly Ser Gly Gly Gly Glu
145                 150                 155                 160

Val Gln Leu Val Glu Ser Gly Gly Ala Leu Val Gln Pro Gly Arg Ser
                165                 170                 175

Leu Arg Leu Ser Cys Arg Thr Ser Gly Leu Asn Phe Gly Asp Tyr Pro
                180                 185                 190

Ile Asn Trp Val Arg Gln Ala Pro Gly Lys Gly Leu Glu Trp Val Gly
                195                 200                 205

Phe Ile Lys Ser Lys Ser Tyr Gly Val Thr Thr Glu Phe Ala Ala Ser
    210                 215                 220

Val Glu Gly Arg Phe Thr Ile Ser Arg Asp Asp Ser Arg Gly Ile Ala
225                 230                 235                 240

Tyr Leu Gln Met Asn Ser Leu Lys Thr Glu Asp Thr Ala Val Tyr Tyr
                245                 250                 255

Cys Thr Ser Ser Ser Gly Phe Leu Tyr Tyr Phe Asp Tyr Trp Gly Gln
                260                 265                 270

Gly Thr Leu Val Thr Val Ser Ser Ala Ser Thr Lys Gly Pro Ser Val
                275                 280                 285

Thr Ser Gly Gln Ala Gly Arg Lys Leu Glu Pro Arg Val Pro Ile Thr
                290                 295                 300

Gln Asn Pro Cys Pro Pro Leu Lys Glu Cys Pro Pro Cys Ala Ala Pro
305                 310                 315                 320

Asp Leu Leu Gly Gly Pro Ser Val Phe Ile Phe Pro Pro Lys Ile Lys
                325                 330                 335

Asp Val Leu Met Ile Ser Leu Ser Pro Met Val Thr Cys Val Val Val
                340                 345                 350

Asp Val Ser Glu Asp Asp Pro Asp Val Gln Ile Ser Trp Phe Val Asn
                355                 360                 365

Asn Val Glu Val His Thr Ala Gln Thr Gln Thr His Arg Glu Asp Tyr
                370                 375                 380

Asn Ser Thr Leu Arg Val Val Ser Ala Leu Pro Ile Gln His Gln Asp
385                 390                 395                 400

Trp Met Ser Gly Lys Glu Phe Lys Cys Lys Val Asn Asn Arg Ala Leu
                405                 410                 415

Pro Ser Pro Ile Glu Lys Thr Ile Ser Lys Pro Arg Gly Pro Val Arg
                420                 425                 430
```

```
Ala Pro Gln Val Tyr Val Leu Pro Pro Pro Ala Glu Glu Met Thr Lys
        435                 440                 445
Lys Glu Phe Ser Leu Thr Cys Met Ile Thr Gly Phe Leu Pro Ala Glu
        450                 455                 460
Ile Ala Val Asp Trp Thr Ser Asn Gly Arg Thr Glu Gln Asn Tyr Lys
465                 470                 475                 480
Asn Thr Ala Thr Val Leu Asp Ser Asp Gly Ser Tyr Phe Met Tyr Ser
                485                 490                 495
Lys Leu Arg Val Gln Lys Ser Thr Trp Glu Arg Gly Ser Leu Phe Ala
            500                 505                 510
Cys Ser Val Val His Glu Gly Leu His Asn His Leu Thr Thr Lys Thr
            515                 520                 525
Ile Ser Arg Ser Leu Gly Lys
530                 535

<210> SEQ ID NO 44
<211> LENGTH: 1608
<212> TYPE: DNA
<213> ORGANISM: artificial sequence
<220> FEATURE:
<223> OTHER INFORMATION: synthetic
<220> FEATURE:
<221> NAME/KEY: sig_peptide
<222> LOCATION: (1)..(60)

<400> SEQUENCE: 44
atggagacag acacactcct gctatgggta ctgctgctct gggttccagg ttccactggt     60
gacgcggatc cggcccaggc ggccgagctc gtgatgactc agtctccaga ctccctggct    120
gtgtctctgg gcgagagggc caccatcaac tgcaagtcca gccagagtgt tttatacagc    180
tccaacaatg agaactactt agcttggtac cagcagaaac aggacagcc tcctaaactg     240
ctcatttact gggcatctac ccgggaatcc ggggtccctg accgattcag tggcagcggg    300
tctgggacag atttcactct caccatcaac agcgtgcagg ctgaggatgt ggcagtttat    360
tactgccagc agtatttat gactcccatc accttcggcc aagggacacg actggagatt    420
aaaggtggtt cctctagatc ttcctcctct ggtggcggtg gctcgggcgg tggtggggag    480
gtgcagctgt ggagtctggg ggggccttg gtacagccag gcggtccct gagactctcc     540
tgtagaacct ctggactcaa ttttggagat tatcctataa actgggtccg ccaggctcca    600
gggaaggggc tggagtgggt agggttcatc aaaagcaagt cttatggtgt gacaacagaa    660
ttcgccgcgt ctgtggaggg cagattcacc atctcaaggg atgattccag aggcatcgcc    720
tatctgcaga tgaacagcct gaaaaccgag gacacagccg tctattactg tacgtccagt    780
agtggttttt tgtactactt tgactactgg gccagggaa ccctggtcac cgtctcctca     840
gcttccacca agggcccatc agtcactagt ggccaggccg ccgcaagct gagcccaga      900
gtgcccataa cacagaaccc ctgtcctcca ctcaaagagt gtccccatg cgcagctcca    960
gacctcttgg gtggaccatc cgtcttcatc ttccctccaa agatcaagga tgtactcatg    1020
atctccctga gccccatggt cacatgtgtg gtggtggatg tgagcgagga tgacccagac   1080
gtccagatca gctggtttgt gaacaacgtg aagtacaca cagctcagac acaaacccat    1140
agagaggatt acaacagtac tctccgggtg gtcagtgccc tccccatcca gcaccaggac   1200
tggatgagtg gcaaggagtt caaatgcaag gtcaacaaca gagccctccc atcccccatc   1260
gagaaaacca tctcaaaacc cagagggcca gtaagagctc cacaggtata tgtcttgcct    1320
ccaccagcag aagagatgac taagaaagag ttcagtctga cctgcatgat cacaggcttc   1380
```

```
ttacctgccg aaattgctgt ggactggacc agcaatgggc gtacagagca aaactacaag    1440
aacaccgcaa cagtcctgga ctctgatggt tcttacttca tgtacagcaa gctcagagta    1500
caaaagagca cttgggaaag aggaagtctt ttcgcctgct cagtggtcca cgagggtctg    1560
cacaatcacc ttacgactaa gaccatctcc cggtctctgg gtaaatga               1608
```

```
<210> SEQ ID NO 45
<211> LENGTH: 535
<212> TYPE: PRT
<213> ORGANISM: artificial sequence
<220> FEATURE:
<223> OTHER INFORMATION: synthetic
<220> FEATURE:
<221> NAME/KEY: SIGNAL
<222> LOCATION: (1)..(20)

<400> SEQUENCE: 45
```

| Met | Glu | Thr | Asp | Thr | Leu | Leu | Leu | Trp | Val | Leu | Leu | Trp | Val | Pro |
|---|---|---|---|---|---|---|---|---|---|---|---|---|---|---|
| 1 | | | | 5 | | | | | 10 | | | | | 15 |

| Gly | Ser | Thr | Gly | Asp | Ala | Asp | Pro | Ala | Gln | Ala | Ala | Glu | Leu | Val | Met |
|---|---|---|---|---|---|---|---|---|---|---|---|---|---|---|---|
| | | | 20 | | | | | 25 | | | | | 30 | | |

Thr Gln Ser Pro Asp Ser Leu Ala Val Ser Leu Gly Glu Arg Ala Thr
                35                  40                  45

Ile Asn Cys Lys Ser Ser Gln Ser Val Leu Tyr Ser Ser Asn Asn Glu
 50                  55                  60

Asn Tyr Leu Ala Trp Tyr Gln Gln Lys Pro Gly Gln Pro Pro Lys Leu
65                  70                  75                  80

Leu Ile Tyr Trp Ala Ser Thr Arg Glu Ser Gly Val Pro Asp Arg Phe
                85                  90                  95

Ser Gly Ser Gly Ser Gly Thr Asp Phe Thr Leu Thr Ile Asn Ser Val
            100                 105                 110

Gln Ala Glu Asp Val Ala Val Tyr Tyr Cys Gln Gln Tyr Phe Met Thr
        115                 120                 125

Pro Ile Thr Phe Gly Gln Gly Thr Arg Leu Glu Ile Lys Gly Gly Ser
    130                 135                 140

Ser Arg Ser Ser Ser Gly Gly Gly Ser Gly Gly Gly Glu
145                 150                 155                 160

Val Gln Leu Leu Glu Ser Gly Gly Ala Leu Val Gln Pro Gly Arg Ser
                165                 170                 175

Leu Arg Leu Ser Cys Arg Thr Ser Gly Leu Asn Phe Gly Asp Tyr Pro
            180                 185                 190

Ile Asn Trp Val Arg Gln Ala Pro Gly Lys Gly Leu Glu Trp Val Gly
        195                 200                 205

Phe Ile Lys Ser Lys Ser Tyr Gly Val Thr Thr Glu Phe Ala Ala Ser
    210                 215                 220

Val Glu Gly Arg Phe Thr Ile Ser Arg Asp Asp Ser Arg Gly Ile Ala
225                 230                 235                 240

Tyr Leu Gln Met Asn Ser Leu Lys Thr Glu Asp Thr Ala Val Tyr Tyr
                245                 250                 255

Cys Thr Ser Ser Ser Gly Phe Leu Tyr Tyr Phe Asp Tyr Trp Gly Gln
            260                 265                 270

Gly Thr Leu Val Thr Val Ser Ser Ala Ser Thr Lys Gly Pro Ser Val
        275                 280                 285

Thr Ser Gly Gln Ala Gly Arg Lys Leu Glu Pro Arg Val Pro Ile Thr
    290                 295                 300

Gln Asn Pro Cys Pro Pro Leu Lys Glu Cys Pro Pro Cys Ala Ala Pro
305                 310                 315                 320

```
Asp Leu Leu Gly Gly Pro Ser Val Phe Ile Phe Pro Pro Lys Ile Lys
            325                 330                 335

Asp Val Leu Met Ile Ser Leu Ser Pro Met Val Thr Cys Val Val Val
            340                 345                 350

Asp Val Ser Glu Asp Asp Pro Asp Val Gln Ile Ser Trp Phe Val Asn
            355                 360                 365

Asn Val Glu Val His Thr Ala Gln Thr Gln Thr His Arg Glu Asp Tyr
        370                 375                 380

Asn Ser Thr Leu Arg Val Val Ser Ala Leu Pro Ile Gln His Gln Asp
385                 390                 395                 400

Trp Met Ser Gly Lys Glu Phe Lys Cys Lys Val Asn Asn Arg Ala Leu
                405                 410                 415

Pro Ser Pro Ile Glu Lys Thr Ile Ser Lys Pro Arg Gly Pro Val Arg
            420                 425                 430

Ala Pro Gln Val Tyr Val Leu Pro Pro Ala Glu Glu Met Thr Lys
        435                 440                 445

Lys Glu Phe Ser Leu Thr Cys Met Ile Thr Gly Phe Leu Pro Ala Glu
            450                 455                 460

Ile Ala Val Asp Trp Thr Ser Asn Gly Arg Thr Glu Gln Asn Tyr Lys
465                 470                 475                 480

Asn Thr Ala Thr Val Leu Asp Ser Asp Gly Ser Tyr Phe Met Tyr Ser
                485                 490                 495

Lys Leu Arg Val Gln Lys Ser Thr Trp Glu Arg Gly Ser Leu Phe Ala
            500                 505                 510

Cys Ser Val Val His Glu Gly Leu His Asn His Leu Thr Thr Lys Thr
            515                 520                 525

Ile Ser Arg Ser Leu Gly Lys
        530                 535

<210> SEQ ID NO 46
<211> LENGTH: 1608
<212> TYPE: DNA
<213> ORGANISM: artificial sequence
<220> FEATURE:
<223> OTHER INFORMATION: synthetic
<220> FEATURE:
<221> NAME/KEY: sig_peptide
<222> LOCATION: (1)..(60)

<400> SEQUENCE: 46
atggagacag acacactcct gctatgggta ctgctgctct gggttccagg ttccactggt      60
gacgcggatc cggcccaggc ggccgagcgc gtgatgacac agtctccaga cgccctggct     120
gtgtctctgg gcgagagggc caccatcaac tgcaagtcca gccagagtct tttatacagc     180
tccaataata gaactactt  agcttggtat cagaagaaac aggacagcc  tcctaagctg     240 ctcatttact gggcatctac ccgggaatcc ggggtccctg accgattcag tgcagcggg      300 tctgggacag agttcactct caccatcaac agcgtgcagg ctgaggatgt ggcagtttat     360
tactgccagc agtattttat gactcccatc accttcggcc aagggaccaa gctggagatc     420
aaaggtggtt cctctagatc ttcctcctct ggtggcggtg gctcgggcgg tggtgggcag     480
gtgcagctgc aggagtcggg gggggccttg gtacagccag gcggtccct  gagactctcc     540 tgtagaacct ctggactcaa ttttggagat tatcctataa actgggtccg ccaggctcca     600
gggaaggggc tggagtgggt agggttcatc aaaaagcaagt cttatggtgt gacaacagaa     660
ttcgccgcgt ctgtggaggg cagattcacc atctcaaggg atgattccag aggcatcgcc     720
```

| | |
|---|---|
| tatctgcaga tgaacagcct gaaaaccgag gacacagccg tctattactg tacgtccagt | 780 |
| agtggttttt tgtactactt tgactactgg ggccagggaa ccctggtcac cgtctcctca | 840 |
| gcttccacca agggcccatc ggtcactagt ggccaggccg ccgcaagct tgagcccaga | 900 |
| gtgcccataa cacagaaccc ctgtcctcca ctcaaagagt gtcccccatg cgcagctcca | 960 |
| gacctcttgg gtggaccatc cgtcttcatc ttccctccaa agatcaagga tgtactcatg | 1020 |
| atctccctga gccccatggt cacatgtgtg gtggtggatg tgagcgagga tgacccagac | 1080 |
| gtccagatca gctggtttgt gaacaacgtg aagtacaca cagctcagac acaaacccat | 1140 |
| agagaggatt acaacagtac tctccgggtg gtcagtgccc tccccatcca gcaccaggac | 1200 |
| tggatgagtg gcaaggagtt caaatgcaag gtcaacaaca gagccctccc atcccccatc | 1260 |
| gagaaaacca tctcaaaacc cagagggcca gtaagagctc cacaggtata tgtcttgcct | 1320 |
| ccaccagcag aagagatgac taagaaagag ttcagtctga cctgcatgat cacaggcttc | 1380 |
| ttacctgccg aaattgctgt ggactggacc agcaatgggc gtacagagca aaactacaag | 1440 |
| aacaccgcaa cagtcctgga ctctgatggt tcttacttca tgtacagcaa gctcagagta | 1500 |
| caaaagagca cttgggaaag aggaagtctt ttcgcctgct cagtggtcca cgagggtctg | 1560 |
| cacaatcacc ttacgactaa gaccatctcc cggtctctgg gtaaatga | 1608 |

<210> SEQ ID NO 47
<211> LENGTH: 535
<212> TYPE: PRT
<213> ORGANISM: artificial sequence
<220> FEATURE:
<223> OTHER INFORMATION: synthetic
<220> FEATURE:
<221> NAME/KEY: SIGNAL
<222> LOCATION: (1)..(20)

<400> SEQUENCE: 47

Met Glu Thr Asp Thr Leu Leu Leu Trp Val Leu Leu Leu Trp Val Pro
1               5                   10                  15

Gly Ser Thr Gly Asp Ala Asp Pro Ala Gln Ala Ala Glu Arg Val Met
            20                  25                  30

Thr Gln Ser Pro Asp Ala Leu Ala Val Ser Leu Gly Glu Arg Ala Thr
        35                  40                  45

Ile Asn Cys Lys Ser Ser Gln Ser Leu Leu Tyr Ser Ser Asn Asn Lys
    50                  55                  60

Asn Tyr Leu Ala Trp Tyr Gln Lys Lys Pro Gly Gln Pro Pro Lys Leu
65                  70                  75                  80

Leu Ile Tyr Trp Ala Ser Thr Arg Glu Ser Gly Val Pro Asp Arg Phe
                85                  90                  95

Ser Gly Ser Gly Ser Gly Thr Glu Phe Thr Leu Thr Ile Asn Ser Val
            100                 105                 110

Gln Ala Glu Asp Val Ala Val Tyr Tyr Cys Gln Gln Tyr Phe Met Thr
        115                 120                 125

Pro Ile Thr Phe Gly Gln Gly Thr Lys Leu Glu Ile Lys Gly Gly Ser
    130                 135                 140

Ser Arg Ser Ser Ser Ser Gly Gly Gly Gly Ser Gly Gly Gly Gly Gln
145                 150                 155                 160

Val Gln Leu Gln Glu Ser Gly Gly Ala Leu Val Gln Pro Gly Arg Ser
                165                 170                 175

Leu Arg Leu Ser Cys Arg Thr Ser Gly Leu Asn Phe Gly Asp Tyr Pro
            180                 185                 190

Ile Asn Trp Val Arg Gln Ala Pro Gly Lys Gly Leu Glu Trp Val Gly

```
                  195                 200                 205
Phe Ile Lys Ser Lys Ser Tyr Gly Val Thr Thr Glu Phe Ala Ala Ser
210                 215                 220

Val Glu Gly Arg Phe Thr Ile Ser Arg Asp Asp Ser Arg Gly Ile Ala
225                 230                 235                 240

Tyr Leu Gln Met Asn Ser Leu Lys Thr Glu Asp Thr Ala Val Tyr Tyr
                245                 250                 255

Cys Thr Ser Ser Ser Gly Phe Leu Tyr Tyr Phe Asp Tyr Trp Gly Gln
                260                 265                 270

Gly Thr Leu Val Thr Val Ser Ser Ala Ser Thr Lys Gly Pro Ser Val
            275                 280                 285

Thr Ser Gly Gln Ala Gly Arg Lys Leu Glu Pro Arg Val Pro Ile Thr
290                 295                 300

Gln Asn Pro Cys Pro Pro Leu Lys Glu Cys Pro Pro Cys Ala Ala Pro
305                 310                 315                 320

Asp Leu Leu Gly Gly Pro Ser Val Phe Ile Phe Pro Pro Lys Ile Lys
                325                 330                 335

Asp Val Leu Met Ile Ser Leu Ser Pro Met Val Thr Cys Val Val Val
                340                 345                 350

Asp Val Ser Glu Asp Asp Pro Asp Val Gln Ile Ser Trp Phe Val Asn
                355                 360                 365

Asn Val Glu Val His Thr Ala Gln Thr Gln Thr His Arg Glu Asp Tyr
            370                 375                 380

Asn Ser Thr Leu Arg Val Val Ser Ala Leu Pro Ile Gln His Gln Asp
385                 390                 395                 400

Trp Met Ser Gly Lys Glu Phe Lys Cys Lys Val Asn Asn Arg Ala Leu
                405                 410                 415

Pro Ser Pro Ile Glu Lys Thr Ile Ser Lys Pro Arg Gly Pro Val Arg
                420                 425                 430

Ala Pro Gln Val Tyr Val Leu Pro Pro Ala Glu Glu Met Thr Lys
            435                 440                 445

Lys Glu Phe Ser Leu Thr Cys Met Ile Thr Gly Phe Leu Pro Ala Glu
450                 455                 460

Ile Ala Val Asp Trp Thr Ser Asn Gly Arg Thr Glu Gln Asn Tyr Lys
465                 470                 475                 480

Asn Thr Ala Thr Val Leu Asp Ser Asp Gly Ser Tyr Phe Met Tyr Ser
                485                 490                 495

Lys Leu Arg Val Gln Lys Ser Thr Trp Glu Arg Gly Ser Leu Phe Ala
            500                 505                 510

Cys Ser Val Val His Glu Gly Leu His Asn His Leu Thr Thr Lys Thr
515                 520                 525

Ile Ser Arg Ser Leu Gly Lys
530                 535

<210> SEQ ID NO 48
<211> LENGTH: 23
<212> TYPE: PRT
<213> ORGANISM: Influenza A virus

<400> SEQUENCE: 48

Ser Leu Leu Thr Glu Val Glu Thr Pro Ile Arg Asn Glu Trp Gly Cys
1               5                   10                  15

Arg Cys Asn Asp Ser Ser Asp
                20
```

```
<210> SEQ ID NO 49
<211> LENGTH: 16
<212> TYPE: PRT
<213> ORGANISM: Influenza A virus

<400> SEQUENCE: 49

Ser Leu Leu Thr Glu Val Glu Thr Pro Ile Arg Asn Glu Trp Gly Cys
1               5                   10                  15

<210> SEQ ID NO 50
<211> LENGTH: 23
<212> TYPE: PRT
<213> ORGANISM: Influenza A virus

<400> SEQUENCE: 50

Ser Leu Leu Thr Glu Val Glu Thr Pro Thr Arg Asn Glu Trp Glu Cys
1               5                   10                  15

Arg Cys Ser Asp Ser Ser Asp
            20

<210> SEQ ID NO 51
<211> LENGTH: 23
<212> TYPE: PRT
<213> ORGANISM: Influenza A virus

<400> SEQUENCE: 51

Ser Leu Leu Thr Glu Val Glu Thr Pro Ile Arg Asn Glu Trp Gly Cys
1               5                   10                  15

Arg Cys Asn Gly Ser Ser Asp
            20

<210> SEQ ID NO 52
<211> LENGTH: 23
<212> TYPE: PRT
<213> ORGANISM: Influenza A virus

<400> SEQUENCE: 52

Ser Leu Leu Thr Glu Val Glu Thr Pro Thr Arg Asn Glu Trp Gly Cys
1               5                   10                  15

Arg Cys Asn Asp Ser Ser Asp
            20

<210> SEQ ID NO 53
<211> LENGTH: 23
<212> TYPE: PRT
<213> ORGANISM: Influenza A virus

<400> SEQUENCE: 53

Ser Leu Leu Thr Glu Val Glu Thr Pro Thr Lys Asn Glu Trp Glu Cys
1               5                   10                  15

Arg Cys Asn Asp Ser Ser Asp
            20

<210> SEQ ID NO 54
<211> LENGTH: 23
<212> TYPE: PRT
<213> ORGANISM: Influenza A virus

<400> SEQUENCE: 54

Ser Leu Leu Thr Glu Val Glu Thr Pro Ile Arg Asn Glu Trp Gly Cys
1               5                   10                  15

Lys Cys Asn Asp Ser Ser Asp
            20
```

```
<210> SEQ ID NO 55
<211> LENGTH: 23
<212> TYPE: PRT
<213> ORGANISM: Influenza A virus

<400> SEQUENCE: 55

Ser Leu Leu Thr Glu Val Glu Thr Pro Ile Arg Asn Glu Trp Glu Cys
1               5                   10                  15

Arg Cys Asn Asp Ser Ser Asp
            20

<210> SEQ ID NO 56
<211> LENGTH: 23
<212> TYPE: PRT
<213> ORGANISM: Influenza A virus

<400> SEQUENCE: 56

Ser Leu Leu Thr Glu Val Glu Thr Pro Ile Arg Asn Gly Trp Glu Cys
1               5                   10                  15

Arg Cys Asn Asp Ser Ser Asp
            20

<210> SEQ ID NO 57
<211> LENGTH: 23
<212> TYPE: PRT
<213> ORGANISM: Influenza A virus

<400> SEQUENCE: 57

Ser Leu Leu Thr Glu Val Glu Thr Pro Ile Arg Ser Glu Trp Gly Cys
1               5                   10                  15

Arg Cys Asn Asp Ser Ser Asp
            20

<210> SEQ ID NO 58
<211> LENGTH: 23
<212> TYPE: PRT
<213> ORGANISM: Influenza A virus

<400> SEQUENCE: 58

Ser Phe Leu Pro Glu Val Glu Thr Pro Ile Arg Asn Glu Trp Gly Cys
1               5                   10                  15

Arg Cys Asn Asp Ser Ser Asp
            20

<210> SEQ ID NO 59
<211> LENGTH: 23
<212> TYPE: PRT
<213> ORGANISM: Influenza A virus

<400> SEQUENCE: 59

Ser Leu Leu Thr Glu Val Glu Thr Pro Ile Arg Asn Glu Trp Gly Cys
1               5                   10                  15

Arg Cys Asn Asp Ser Ser Asn
            20

<210> SEQ ID NO 60
<211> LENGTH: 23
<212> TYPE: PRT
<213> ORGANISM: Influenza A virus

<400> SEQUENCE: 60

Ser Leu Leu Thr Glu Val Glu Thr Pro Ile Arg Asn Glu Trp Gly Cys
1               5                   10                  15
```

Arg Cys Asn Asp Ser Ser Asp
            20

<210> SEQ ID NO 61
<211> LENGTH: 23
<212> TYPE: PRT
<213> ORGANISM: Influenza A virus

<400

```
<400> SEQUENCE: 66

Ser Leu Leu Pro Glu Val Glu Thr Pro Ile Arg Asn Gly Trp Gly Cys
1               5                   10                  15

Arg Cys Asn Asp Ser Ser Asp
            20

<210> SEQ ID NO 67
<211> LENGTH: 23
<212> TYPE: PRT
<213> ORGANISM: Influenza A virus

<400> SEQUENCE: 67

Ser Leu Leu Thr Glu Val Glu Thr Pro Thr Arg Asn Gly Trp Glu Cys
1               5                   10                  15

Arg Cys Asn Asp Ser Ser Asp
            20

<210> SEQ ID NO 68
<211> LENGTH: 23
<212> TYPE: PRT
<213> ORGANISM: Influenza A virus

<400> SEQUENCE: 68

Ser Phe Leu Thr Glu Val Glu Thr Pro Ile Arg Asn Glu Trp Gly Cys
1               5                   10                  15

Arg Cys Asn Gly Ser Ser Asp
            20

<210> SEQ ID NO 69
<211> LENGTH: 23
<212> TYPE: PRT
<213> ORGANISM: Influenza A virus

<400> SEQUENCE: 69

Ser Leu Leu Thr Glu Val Glu Thr Pro Ile Arg Asn Glu Trp Glu Tyr
1               5                   10                  15

Arg Cys Ser Asp Ser Ser Asp
            20

<210> SEQ ID NO 70
<211> LENGTH: 23
<212> TYPE: PRT
<213> ORGANISM: Influenza A virus

<400> SEQUENCE: 70

Ser Leu Leu Thr Glu Val Glu Thr Leu Thr Arg Asn Gly Trp Gly Cys
1               5                   10                  15

Arg Cys Ser Asp Ser Ser Asp
            20

<210> SEQ ID NO 71
<211> LENGTH: 23
<212> TYPE: PRT
<213> ORGANISM: Influenza A virus

<400> SEQUENCE: 71

Ser Leu Leu Thr Glu Val Glu Thr Leu Thr Lys Asn Gly Trp Gly Cys
1               5                   10                  15

Arg Cys Ser Asp Ser Ser Asp
            20

<210> SEQ ID NO 72
```

-continued

```
<211> LENGTH: 23
<212> TYPE: PRT
<213> ORGANISM: Influenza A virus

<400> SEQUENCE: 72

Ser Leu Leu Thr Glu Val Glu Thr His Thr Arg Asn Glu Trp Glu Cys
1               5                   10                  15

Arg Cys Asn Asp Ser Ser Asp
            20

<210> SEQ ID NO 73
<211> LENGTH: 23
<212> TYPE: PRT
<213> ORGANISM: Influenza A virus

<400> SEQUENCE: 73

Ser Leu Leu Thr Glu Val Glu Thr Pro Thr Arg Asn Gly Trp Glu Cys
1               5                   10                  15

Lys Cys Asn Asp Ser Ser Asp
            20

<210> SEQ ID NO 74
<211> LENGTH: 23
<212> TYPE: PRT
<213> ORGANISM: Influenza A virus

<400> SEQUENCE: 74

Ser Phe Leu Thr Glu Val Glu Thr Leu Thr Arg Asn Gly Trp Glu Cys
1               5                   10                  15

Arg Cys Ser Asp Ser Ser Asp
            20

<210> SEQ ID NO 75
<211> LENGTH: 23
<212> TYPE: PRT
<213> ORGANISM: Influenza A virus

<400> SEQUENCE: 75

Ser Leu Leu Thr Glu Val Glu Thr Leu Thr Arg Asn Gly Trp Glu Cys
1               5                   10                  15

Lys Cys Ser Asp Ser Ser Asp
            20

<210> SEQ ID NO 76
<211> LENGTH: 23
<212> TYPE: PRT
<213> ORGANISM: Influenza A virus

<400> SEQUENCE: 76

Ser Leu Leu Thr Glu Val Asp Thr Leu Thr Arg Asn Gly Trp Gly Cys
1               5                   10                  15

Arg Cys Ser Asp Ser Ser Asp
            20

<210> SEQ ID NO 77
<211> LENGTH: 23
<212> TYPE: PRT
<213> ORGANISM: Influenza A virus

<400> SEQUENCE: 77

Ser Leu Leu Thr Glu Val Glu Thr Pro Thr Arg Asn Gly Trp Gly Cys
1               5                   10                  15

Arg Cys Ser Asp Ser Ser Asp
```

```
          20

<210> SEQ ID NO 78
<211> LENGTH: 24
<212> TYPE: PRT
<213> ORGANISM: Influenza A virus

<400> SEQUENCE: 78

Met Ser Leu Leu Thr Glu Val Lys Thr Pro Thr Arg Asn Gly Trp Glu
1               5                   10                  15

Cys Lys Cys Ser Asp Ser Ser Asp
          20

<210> SEQ ID NO 79
<211> LENGTH: 23
<212> TYPE: PRT
<213> ORGANISM: Influenza A virus

<400> SEQUENCE: 79

Ser Leu Leu Thr Glu Val Glu Thr Pro Thr Arg Asp Gly Trp Glu Cys
1               5                   10                  15

Lys Cys Ser Asp Ser Ser Asp
          20

<210> SEQ ID NO 80
<211> LENGTH: 24
<212> TYPE: PRT
<213> ORGANISM: Influenza A virus

<400> SEQUENCE: 80

Met Ser Leu Leu Thr Glu Val Glu Thr His Thr Arg Asn Gly Trp Glu
1               5                   10                  15

Cys Lys Cys Ser Asp Ser Ser Asp
          20

<210> SEQ ID NO 81
<211> LENGTH: 23
<212> TYPE: PRT
<213> ORGANISM: Influenza A virus

<400> SEQUENCE: 81

Ser Leu Pro Thr Glu Val Glu Thr Pro Ile Arg Asn Glu Trp Gly Cys
1               5                   10                  15

Arg Cys Asn Asp Ser Ser Asp
          20

<210> SEQ ID NO 82
<211> LENGTH: 23
<212> TYPE: PRT
<213> ORGANISM: Influenza A virus

<400> SEQUENCE: 82

Ser Leu Leu Thr Glu Val Glu Thr Pro Ile Arg Ser Glu Trp Gly Cys
1               5                   10                  15

Arg Cys Asn Asp Ser Gly Asp
          20

<210> SEQ ID NO 83
<211> LENGTH: 23
<212> TYPE: PRT
<213> ORGANISM: Influenza A virus

<400> SEQUENCE: 83
```

```
Ser Leu Leu Thr Glu Val Glu Thr Pro Ile Arg Lys Gly Trp Glu Cys
1               5                   10                  15

Asn Cys Ser Asp Ser Ser Asp
            20
```

<210> SEQ ID NO 84
<211> LENGTH: 97
<212> TYPE: PRT
<213> ORGANISM: Influenza A virus

<400> SEQUENCE: 84

```
Met Ser Leu Leu Thr Glu Val Glu Thr Pro Ile Arg Asn Glu Trp Gly
1               5                   10                  15

Cys Arg Cys Asn Gly Ser Ser Asp Pro Leu Thr Ile Ala Ala Asn Ile
            20                  25                  30

Ile Gly Ile Leu His Leu Thr Leu Trp Ile Leu Asp Arg Leu Phe Phe
        35                  40                  45

Lys Cys Ile Tyr Arg Arg Phe Lys Tyr Gly Leu Lys Gly Gly Pro Ser
    50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu
```

<210> SEQ ID NO 85
<211> LENGTH: 97
<212> TYPE: PRT
<213> ORGANISM: Influenza A virus

<400> SEQUENCE: 85

```
Met Ser Leu Leu Thr Glu Val Glu Thr Pro Thr Arg Asn Glu Trp Glu
1               5                   10                  15

Cys Arg Cys Ser Asp Ser Ser Asp Pro

```
ggccagggca cccggctgga aatcaag                                      327

<210> SEQ ID NO 87
<211> LENGTH: 327
<212> TYPE: DNA
<213> ORGANISM: Homo sapiens

<400> SEQUENCE: 87
acccagagcc ccgacagcct ggccgtgagc ctgggcgagc gggccaccat caactgcaag    60
agcagccaga gcgtgctgta cagcagcaac aacgagaact acctggcctg gtatcagcag   120
aagcccggcc agccccccaa gctgctgatc tactgggcca gcacccggga gagcggcgtg   180
cccgaccggt ttagcggcag cggctccggc accgacttca ccctgaccat caacagcgtg   240
caggccgagg acgtggccgt gtactactgc cagcagtact tcatgacccc catcaccttc   300
ggccagggca cccggctgga aatcaag                                      327

<210> SEQ ID NO 88
<211> LENGTH: 327
<212> TYPE: DNA
<213> ORGANISM: Homo sapiens

<400> SEQUENCE: 88
acccagagcc ccgacgccct ggccgtgagc ctgggcgagc gggccaccat caactgcaag    60
agcagccaga gcctgctgta cagcagcaac aacaagaact acctggcctg gtatcagaaa   120
aagcccggcc agccccccaa gctgctgatc tactgggcca gcacccggga gagcggcgtg   180
cccgaccggt ttagcggcag cggctccggc accgagttca ccctgaccat caacagcgtg   240
caggccgagg acgtggccgt gtactactgc cagcagtact tcatgacccc catcaccttc   300
ggccagggca cccggctgga aatcaag                                      327

<210> SEQ ID NO 89
<211> LENGTH: 345
<212> TYPE: DNA
<213> ORGANISM: Homo sapiens

<400> SEQUENCE: 89
agcggcggag ccctggtgca gcccggcaga agcctgagac tgagctgccg gaccagcggc    60
ctgaacttcg gcgactaccc catcaactgg gtgcggcagg ctccaggaa aggactcgaa   120 tgggtgggct tcatcaagag caagagctac ggcgtgacca ccgagttcgc cgccagcgtg   180
gagggccggt tcaccatcag ccgggacgac agccggggca ttgcctacct gcagatgaac   240
agcctgaaaa ccgaggacac cgccgtgtac tactgcacca gcagcagcgg ctttctgtac   300
tacttcgact actgggggaca gggcaccctg gtgaccgtga gcagc                  345

<210> SEQ ID NO 90
<211> LENGTH: 23
<212> TYPE: PRT
<213> ORGANISM: Influenza A virus

<400> SEQUENCE: 90

Ser Leu Leu Thr Glu Val Glu Thr Pro Thr Arg Asn Gly Trp Glu Cys
1               5                   10                  15

Lys Cys Ser Asp Ser Ser Asp
            20

<210> SEQ ID NO 91
<211> LENGTH: 23
<212> TYPE: PRT
```

-continued

```
<213> ORGANISM: Influenza A virus

<400> SEQUENCE: 91

Ser Leu Leu Thr Gly Val Glu Thr His Thr Arg Asn Gly Trp Gly Cys
1               5                   10                  15

Lys Cys Ser Asp Ser Ser Asp
            20

<210> SEQ ID NO 92
<211> LENGTH: 23
<212> TYPE: PRT
<213> ORGANISM: Influenza A virus

<400> SEQUENCE: 92

Ser Leu Leu Pro Glu Val Glu Thr His Thr Arg Asn Gly Trp Gly Cys
1               5                   10                  15

Arg Cys Ser Asp Ser Ser Asp
            20

<210> SEQ ID NO 93
<211> LENGTH: 8
<212> TYPE: PRT
<213> ORGANISM: Influenza A virus

<400> SEQUENCE: 93

Leu Leu Thr Glu Val Glu Thr Pro
1               5
```